(12) United States Patent
Nagashima et al.

(10) Patent No.: US 7,449,456 B2
(45) Date of Patent: Nov. 11, 2008

(54) DIAMINOPYRIMIDINECARBOXAMIDE DERIVATIVE

(75) Inventors: Shinya Nagashima, Tsukuba (JP); Hiroshi Nagata, Tsukuba (JP); Masahiro Iwata, Tsukuba (JP); Masaki Yokota, Tsukuba (JP); Hiroyuki Moritomo, Tsukuba (JP); Eiichi Nakai, Tsukuba (JP); Sadao Kuromitsu, Tsukuba (JP); Keiko Ohga, Tsukuba (JP); Makoto Takeuchi, Tsukuba (JP)

(73) Assignee: Astellas Pharma, Inc., Tokyo (JP)

( * ) Notice: Subject to any disclaimer, the term of this patent is extended or adjusted under 35 U.S.C. 154(b) by 587 days.

(21) Appl. No.: 10/518,043

(22) PCT Filed: Jun. 26, 2003

(86) PCT No.: PCT/JP03/08129

§ 371 (c)(1),
(2), (4) Date: Dec. 16, 2004

(87) PCT Pub. No.: WO2004/002964

PCT Pub. Date: Jan. 8, 2004

(65) Prior Publication Data

US 2005/0272753 A1 Dec. 8, 2005

(30) Foreign Application Priority Data

Jun. 28, 2002 (JP) .............................. 2002-190959

(51) Int. Cl.
*C07D 239/48* (2006.01)
*A61K 31/506* (2006.01)

(52) U.S. Cl. .................. 514/218; 514/227.8; 514/235.8; 514/252.14; 514/275; 540/575; 544/60; 544/122; 544/295; 544/323

(58) Field of Classification Search ................. 540/575; 544/60, 122, 295, 323; 514/218, 227.8, 235.8, 514/252.14, 275
See application file for complete search history.

(56) References Cited

U.S. PATENT DOCUMENTS 6,200,977 B1 3/2001 Cushing et al.
6,432,963 B1 8/2002 Hisamichi et al.
6,528,513 B2 3/2003 Cushing et al.
2001/0018436 A1 8/2001 Cushing et al.
2004/0006068 A1 1/2004 Cushing et al.

FOREIGN PATENT DOCUMENTS

WO WO 99/31073 A1 6/1999
WO WO 99/41253 A1 8/1999
WO WO 00/39101 A1 7/2000

OTHER PUBLICATIONS

Taylor et al., CAPLUS Abstract 55:33107 (1961).*
International Search Report dated Jul. 28, 2003.
Supplementary European Search Report dated Feb. 12, 2007.
Hautamaki, et al, "Requirement for Macrophage Elastase for Cigarette Smoke-Induced Emphysema in Mice," Science, 277, pp. 2002-2004 (1997).
Kuperman, et al., "Direct effects of interleukin-13 on epithelial cells cause airway hyperreactivity and mucus overproduction in asthma," Nature Medicine, 8:*, pp. 885-889 (Aug. 2002).
March, et al, "Effects of Concurrent Ozone Exposure On The Pathogenesis of Cigarette Smoke-Induced Emphysema in B6C3F$_1$ Mice," Inhalation Toxicology, 14, pp. 1187-1213 (2002).
Ofulue, A.F., et al., "Time course of neutrophil and macrophage elastolytic activities in cigarette smoke-induced emphysema," The American Journal of Physicol. Lung Cell Mol Physiol, 275, pp. L1134-L1144 (1998).
Zheng, et al., "Inducible targeting of IL-13 to the adult lung causes matrix metalloproteinase-and-cathepsin-dependent emphysema," J. of Clinical Investigation, 106, pp. 1081-1093 (Nov. 2000).

* cited by examiner

*Primary Examiner*—Deepak Rao
(74) *Attorney, Agent, or Firm*—Sughrue Mion, PLLC

(57) ABSTRACT

A compound which may be used for the prevention or treatment of respiratory diseases in which STAT 6 is concerned, particularly asthma, chronic obstructive pulmonary disease and the like is provided.

A pyrimidine derivative or a salt thereof, which has an arylamino or arylethylamino group which may be substituted with a specified substituent, at the 2-position, amino group substituted with benzyl group or the like, at the 4-position, and carbamoyl group which may be substituted, at the 5-position, is provided.

18 Claims, No Drawings

DIAMINOPYRIMIDINECARBOXAMIDE DERIVATIVE

This application is a 371 of PCT/JP03/08129 filed Jun. 26, 2003.

TECHNICAL FIELD

The present invention relates to medicaments, particularly STAT 6 (signal transducer and activator of transcription 6) inhibitors and novel diaminopyrimidinecarboxamide derivatives useful as agents for treating respiratory diseases in which STAT 6 is participated.

BACKGROUND OF THE INVENTION

It is known that asthma is a disease characterized by a reversible airway obstruction which is accompanied by chronic inflammation and overreaction of airway and that CD4$^+$ T cells, particularly Th2 cell is taking an important role. It is known that Th2 cell is differentiated from Thp cell by IL-4, and that IL-4 and IL-13 produced from Th2 cell cause airway contraction and chronic inflammation of airway through inducing production of IgE antibody production, activation and infiltration of eosinophil and increase of mucus secretion. In addition, it has been reported that IL-13 is also participated in the airway epithelial hypertrophy and airway sub-epithelial fibrosis (*J. Clin. Invest.*, 103, 6, 779-788, 1999), destruction of alveolus (*J. Clin. Invest.*, 106, 1081-1093, 2000) and the like symptoms which are found in respiratory diseases such as asthma, chronic obstructive pulmonary disease (COPD) and the like.

STAT 6 (signal transducer and activator of transcription 6) is participated in the intracellular signal transduction of IL-4 and IL-13. It has been reported that differentiation of Th2 cell from Thp cell does not occur by the deletion of STAT 6 (*Immunity*, 4, 313-319, 1996) and that production of IgE, acceleration of airway reactivity and infiltration of eosinophil into airway and lung are inhibited in an asthma model of STAT 6 deletion mouse (J. Exp. Med., 187, 9, 1537-1542, 1998). These reports suggest that STAT 6 participates in inflammatory respiratory diseases such as asthma and the like.

Also, It has been reported that STAT 6 and IL-4 mRNA in nasal mucosa increase by administration of antigens to patients of allergic rhinitis (Clin. Exp. Allergy, 30, 86-93, 1709-1716, 2000) and also that dermatitis-like symptoms such as infiltration of inflammatory cells into the skin are induced by effecting over-expression of IL-4 in mice (*J. Tnvest. Dermatol.*, 117, 4, 977-983 (2001)). These reports suggest that STAT 6 participates in allergic rhinitis and dermatitis.

STAT 6 is bonded to GYKXF motif of IL-4 receptor a chain (IL-4Rα) which is a constituting factor of IL-4 receptor and IL-13 receptor (*Science*, 165, 1265-1267, 1994), and a JAK family kinase is also bonded to these receptors. When IL-4 or IL-13 is bonded to a receptor, STAT 6 is dimerized by undergoing tyrosine-phosphorylation by the JAK family kinase and translocated into the nucleus where it exerts a function as the transcription factor (*Science*, 165, 1265-1267, 1994). Accordingly, if any one of these steps, for example, the tyrosine-phosphorylation of STAT 6, can be inhibited, it becomes possible to inhibit the function of STAT 6 as a transcription factor so that its effectiveness is expected in treating the aforementioned various diseases in which IL-4 and IL-13 are participated.

Since Syk tyrosine kinase as a Zap/Syk family kinase classified into a genealogical relation different from the JAK family kinase based on the gene sequence genealogical tree (Genome Biology, 3, research 0043.1-0043.12) mediates signals from antibody receptors (FcεRI, EcγR) and antigen receptors (BCR, TCR) and apoptosis inhibition signal of eosinophil by GM-CSF, it has been reported that an Syk inhibitor is expected as an agent for inflammations including asthma or allergic diseases (e.g., Patent Reference 1). However, there are no reports on the participation of Syk in the signals of IL-4 and IL-13. It is considered that an Syk inhibitor expresses its effect by inhibiting all of the activation via respective antigen receptors of B cell and T cell, inhibiting antibody production in the case of antibodies regardless of their subclasses and inhibiting differentiation of helper T cell nonspecifically. That is, it is predicted that Syk inhibitors always accompany inhibitory action of infection protection, immunological functions and the like. In the case of STAT 6 inhibitors on the other hand, since the function of STAT 6 is specific for IL-4 and IL-13, they specifically inhibit production of IgE in the case of antibodies and differentiation of Th2 in the case of T cell subsets. Accordingly, it is expected that STAT 6 inhibitors are effective as agents for treating allergic or inflammatory respiratory diseases having less influences upon infection protection, immunological function and the like (*J. Clin. Inves.*, 109, 1279-1283, 2002).

Diaminopyrimidine-5-carboxamide derivatives-useful for the treatment of inflammatory and allergic diseases, immune diseases and the like based on the Syk tyrosine kinase inhibition have been reported and, for example, the following compound has been reported in Patent Reference 1.

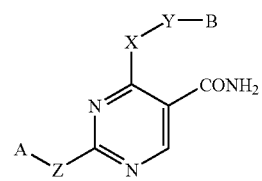

(Z represents O, NR$^2$ or a bond and A represents a lower alkyl, aryl or the like which may have a substituent(s), wherein —NH$_2$, —NH-lower alkyl, —N(lower alkyl)$_2$, —NH-lower alkylene-aryl, —NH-cycloalkyl, —NH-aryl, —NH-heteroaryl and the like are disclosed as substituents of said aryl which may have a substituent(s), but they are not a saturated hetero ring, and there is no illustrative disclosure of the 3-chloro-4-hydroxyphenyl group as a substituent of the lower alkyl which may have a substituent. See said published application for details.)

However, there is no disclosure not only on the action of said compound upon STAT 6 but also on its action upon IL-4 and IL-13. Also, since Syk tyrosine kinase concerns itself in the signal transduction of B cell, T cell, mast cell or the like when these cells are stimulated with an antigen, the effect of its inhibitor as an agent for treating inflammatory diseases can be expected, but its immunosuppressive effects and the like must also be taken into consideration.

In addition, compounds having antiviral activities, including diaminopyrimidine-5-carboxamide derivatives, represented by the following general formula have also been reported (e.g., Patent Reference 2).

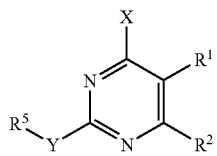

(X represents —NR³R⁴ or the like, Y represents —N(R⁶)— or the like, R¹ represents —C(O)NR⁷R⁸ or the like and R⁵ represents aryl or the like, and said aryl may be substituted with —NR'R", —R' or the like, wherein said R' and R" represent hydrogen, (C1-C8)alkyl, aryl, aryl-(C1-C4)alkyl or aryloxy-(C1-C4)alkyl, but they are not a saturated hetero ring, and there is no disclosure on the illustrative compounds in which the R⁵—Y moiety is 4-hydroxyphenetyl group. See said published application for details.)

Also, other pyrimidine-5-carboxamide derivatives useful as PDE 5 inhibitors (e.g., Patent Reference 3; the 2-position substituent of the pyrimidine ring is a lower alkylamino or indanylamino group which may be substituted), NOS inhibitors (e.g., Patent Reference 4; imidazolylphenyl group and 1,3-benzodioxol-5-yl group are essential), anticancer agents (e.g., Patent Reference 5; the 4-position substituent of the pyrimidine ring is an amino group which is directly bonded to a ring group), anti-fugal agents (e.g., Patent Reference 6; an alkynyl group is essential on the 4-position substituent of the pyrimidine ring) and the like have been reported, but all of them do not disclose or suggest on the inhibitory activity for STAT 6 activation.

In addition, dihydrothiadiazole derivatives (e.g., Patent Reference 7), imidazopyrimidine derivatives (e.g., Patent Reference 8), benzofuran derivatives (e.g., Patent Reference 9), imidazo[2,1-b]thiazole derivatives (e.g., Patent Reference 10), tetrahydroquinoline derivatives (e.g., Patent Reference 11) and the like have been reported as STAT 6 activation inhibitors, but there are no reports on pyrimidine derivatives.

Patent Reference 1
International Publication No. 99/31073 pamphlet
Patent Reference 2
International Publication No. 99/41253 pamphlet
Patent Reference 3
International Publication No. 01/83460 pamphlet
Patent Reference 4
International Publication No. 01/72744 pamphlet
Patent Reference 5
International Publication No. 00/39101 pamphlet
Patent Reference 6
German Patent Application Publication. No. 4029650 specification
Patent Reference 7
JP-A-2000-229959
Patent Reference 8
International Publication No. 02/14321 pamphlet
Patent Reference 9
International Publication No. 02/53550 pamphlet
Patent Reference 10
JP-A-11-106340
Patent Reference 11
International Publication No. 02/79165 pamphlet Since inhibitors of STAT 6 activation are expected as agents for treating respiratory diseases such as asthma, COPD and the like, great demand has been directed toward the development of novel compounds.

DISCLOSURE OF THE INVENTION

The present inventors have found that diaminopyrimidine-5-carboxamide derivatives partly disclosed in Patent Reference 1 have the inhibitory activity for STAT 6 activation. A compound having said inhibitory activity can be expected as an agent for treating respiratory diseases such as asthma, COPD and the like, having less suppressive effect on immunological function, and also is useful as an agent for treating other inflammatory and allergic diseases. Accordingly, intensive studies on the compounds having the inhibitory activity for STAT 6 activation were conducted, with the aim of providing novel compounds which have less side effects and are useful for the treatment of respiratory diseases and the like and further providing medicaments containing them. As a result, a novel diaminopyrimidine-5-carboxamide derivative having an aromatic ring group linked to the 2-position through a specified linking arm and a substituted amino group on the 4-position was found, and it was found that said compound has a potent and selective STAT 6 inhibitory activity, thereby accomplishing the present invention.

That is, the present invention relates to a STAT 6 activation inhibitor which comprises a diaminopyrimidinecarboxamide derivative represented by the following formula (I) or a salt thereof as the active ingredient,

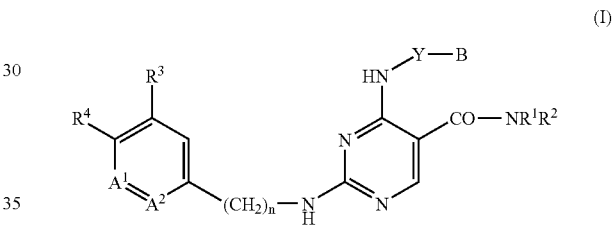

(symbols in the formula have the following meanings:
A¹: CR⁵ or N,
R⁵: —H, -lower alkyl, —O-lower alkyl or -halogen,
A²: CR⁶ or N,
R⁶: —H or -halogen,
R³: —R⁰, -lower alkyl substituted with halogen, -halogen, —OR⁰, —S-lower alkyl, —CO-lower alkyl, —CO₂-lower alkyl, -lower alkylene-OH, -hetero ring, —O-hetero ring, —N(R⁰)-hetero ring, -lower alkylene-hetero ring, —O-lower alkylene-hetero ring, —S-lower alkylene-hetero ring, —SO-lower alkylene-hetero ring, —SO₂-lower alkylene-hetero ring, —N(R⁰)-lower alkylene-hetero ring, -lower alkylene-CO-hetero ring, -lower alkylene-N(R⁰)₂, —SO₂—N(R⁰)-lower alkyl or -lower alkylene-N(R⁰)—CO₂-lower alkylene-phenyl,
R⁰: the same or different from one another, and each is H or a lower alkyl,
n: 0 or 2,
R⁴: (i) when n=2, —R⁰, lower alkyl substituted with halogen, —OR⁰, —N(R⁰)—CHO, —N(R⁰)—CO-lower alkyl or —N(R⁰)—SO₂-lower alkyl,
(ii) when n=0, —H, lower alkyl substituted with halogen, —OH, —NH—CHO, —CON(R⁰)₂, -lower alkylene substituted with halogen-OH, -lower alkylene-NH₂, -lower alkylene-NHCONH₂, -lower alkylene-CO₂H, -lower alkylene-CO₂-lower alkyl, -lower alkylene-CN, or —CH(lower alkylene-OH)₂, or a group represented by a formula —Xᵃ—R⁴ᵃ, X$^a$: single bond, —O—, —CO—, —S—, —SO$_2$—, —N(R$^0$)—, —N(R$^0$)CO—, —N(R$^0$)SO$_2$—, -lower alkylene-O—, -lower alkylene-N(R$^0$)—, -lower alkylene-N(R$^0$)CO—, -lower alkylene-N(R$^0$)SO$_2$—, -lower alkylene-N(R$^0$)CO$_2$—, —N(CO—R$^0$)—, —N(SO$_2$-lower alkyl)-, —CON(R$^0$)—, -lower alkylene-O—CO—, -lower alkenylene-CO—, -lower alkenylene-CON(R$^0$)—, -lower alkenylene-CO$_2$—, —O—(CH$_2$)$_k$-cycloalkylene-(CH$_2$)$_m$—, —N(R$^0$)—(CH$_2$)$_k$-cycloalkylene-(CH$_2$)$_m$—, —CO—(CH$_2$)$_k$-cycloalkylene-(CH$_2$)$_m$—, —CON(R$^0$)—(CH$_2$)$_k$-cycloalkylene-(CH$_2$)$_m$— or —N(R$^0$)CO—(CH$_2$)$_k$-cycloalkylene-(CH$_2$)$_m$—, k and m, the same or different from each other, and each is 0, 1, 2, 3 or 4, R$^{4a}$: lower alkyl, phenyl, hetero ring, cycloalkyl, lower alkylene-phenyl, lower alkylene-hetero ring, lower alkylene-OH, lower alkenyl, lower alkenylene-phenyl or lower alkenylene-hetero ring, wherein the hetero rings in R$^3$ and R$^{4a}$ may be substituted with 1 to 5 of lower alkyl, halogen, —OR$^0$, —S-lower alkyl, —S(O)-lower alkyl, —SO$_2$-lower alkyl, lower alkylene-OR$^0$, —N(R$^0$)$_2$, —CO$_2$R$^0$, —CON(R$^0$)$_2$, —CN, —CHO, —SO$_2$N(R$^0$)$_2$, —N(R$^0$)—SO$_2$-lower alkyl, —N(R$^0$)—CO—N(R$^0$)$_2$, —N(R$^0$)—CO$_2$-lower alkyl, —N(R$^0$)—CO$_2$-cycloalkyl, —NH—C(=NH)—NH-lower alkyl, —NH—C(=N—CN)—NH-lower alkyl, hetero ring (said hetero ring may be substituted with 1 to 5 substituents selected from lower alkyl, OH and lower alkylene-OH), -lower alkylene-NH—C(=NN)—NH$_2$, —O-phenyl, —CO-phenyl, —N(R$^0$)—CO-lower alkyl, —N(R$^0$)—CO-lower alkylene-N(R$^0$)$_2$, -lower alkylene-N(R$^0$)—CO-lower alkylene-N(R$^0$)$_2$, —CO—N(R$^0$)-lower alkylene-N(R$^0$)$_2$, —CO-lower alkylene-N(R$^0$)$_2$, —CO-lower alkylene-CO$_2$R$^0$, -lower alkylene-N(R$^0$)$_2$, -lower alkylene-CO$_2$R$^0$, -lower alkylene-CO—N(R$^0$)$_2$, -lower alkylene-N(R$^0$)—CO-lower alkyl, -lower-alkylene-N(R$^0$)—CO$_2$-lower alkyl, -lower alkylene-N(R$^0$)—SO$_2$-lower alkyl, -lower alkylene-hetero ring (said hetero ring may be substituted with 1 to 5 substituents selected from lower alkyl, OH and lower alkylene-OH), lower alkylene-O-lower alkylene-phenyl, =N—O—R$^0$ or oxo, and phenyl and cycloalkyl may be substituted with 1 to 5 of lower alkyl, OH, O-lower alkyl or N(R$^0$)$_2$, and wherein the lower alkylene in R$^3$, R$^4$, R$^{4a}$ and X$^a$ may be substituted with 1 to 5 of —OR$^0$, —CO$_2$R$^0$, —CON(R$^0$)$_2$, —N(R$^0$)$_2$, —N(R$^0$)COR$^0$ or hetero ring, or R$^3$ and R$^4$ may together form *—N(R$^7$)—(CH$_2$)$_2$—, *—(CH$_2$)$_2$—N(R$^7$)—, *—CH$_2$—N(R$^7$)—CH$_2$—, *—N(R$^7$)—(CH$_2$)$_3$—, *—(CH$_2$)$_3$—N(R$^7$)—, *—CH$_2$—N(R$^7$)—(CH$_2$)$_2$—, *—(CH$_2$)$_2$—N(R$^7$)—CH$_2$—, *—C(O)—N(R$^7$)—(CH$_2$)$_2$—, *—(CH$_2$)$_2$—N(R$^7$)—C(O)—, *—N(R$^7$)—CH=CH—, *—CH=CH—N(R$^7$)—, *—N=CH—CH=CH—, *—CH=N—CH=CH—, *—CH=CH—N=CH—, *—CH=CH—CH=N—, *—N=CH—CH=N—, *—CH=N—N=CH—, *—N(R$^7$)—N=CH—, *—CH=N—N(R$^7$)—, *—O—CH$_2$—O—, *—O—(CH$_2$)$_2$—O—, *—O—(CH$_2$)$_3$—, *—O—(CH$_2$)$_2$—N(R$^7$)—, *—(CH$_2$)$_2$—C(O)—, *—CH=CH—C(O)—O— or *—N=C(CF$_3$)—NH—, wherein * indicates bonding to the position shown by R$^3$, R$^7$: —H, -lower alkyl or —CO-lower alkyl, B: H, lower alkenyl, lower alkynyl, lower alkyl substituted with halogen, CN, S-lower alkyl, aryl which may have a substituent(s), cycloalkyl which may have a substituent(s) or hetero ring which may have a substituent(s), Y: single bond; or lower alkylene which may be substituted with 1 to 5 groups selected from halogen, OH, O-lower alkyl, —NH$^2$, —NH-lower alkyl and —N(lower alkyl)$_2$, and R$^1$ and R$^2$: the same or different from each other, and each represents H, lower alkyl or O-lower alkyl which may have a substituent(s)).

Also, according to the present invention, a Th2 cell differentiation inhibitor which comprises a diaminopyrimidinecarboxamide derivative or a salt thereof as the active ingredient.

Also, the present invention relates to the use of the diaminopyrimidinecarboxamide derivative represented by formula (I) or a salt thereof for the manufacture of a STAT 6 activation inhibitor or a Th2 cell differentiation inhibitor. Also, the present invention relates to a method for inhibiting activation of STAT 6 or a method for inhibiting differentiation of Th2 cell, which comprises administering an effective amount of the diaminopyrimidinecarboxamide derivative represented by formula (I) or a salt thereof to a mammal.

The present invention also relates to a novel diaminopyrimidinecarboxamide derivative represented by the following formula (Ia) or a salt thereof, which is included in the compounds of the aforementioned formula (I), characterized in that it has at least one saturated heterocyclic group in the R$^4$ of formula (I).

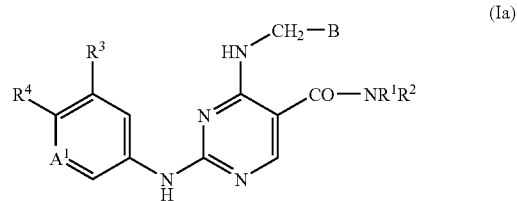

(Ia)

(symbols in the formula have the following meanings:

A$^1$: CR$^5$ or N,

R$^5$: —H, -lower alkyl, —O-lower alkyl or -halogen,

R$^3$: —R$^0$, -lower alkyl substituted with halogen, -halogen, —OR$^0$, —S-lower alkyl, —CO-lower alkyl, —CO$_2$-lower alkyl, -lower alkylene-OH, -saturated hetero ring, —X$^b$-heteroaryl, —X$^b$-saturated hetero ring, —X$^b$-heteroaryl, -lower alkylene-N(R$^0$)$_2$, —SO$_2$—N(R$^0$)-lower alkyl or -lower alkylene-N(R$^0$)—CO$_2$-lower alkylene-phenyl, X$^b$: -lower alkylene-, —O-lower alkylene-, —S-lower alkylene-, —SO-lower alkylene-, —SO$_2$-lower alkylene-, —N(R$^0$)-lower alkylene- or -lower alkylene-CO—, R$^0$: the same or different from one another, and each represents H or a lower alkyl, R$^4$: —X$^a$-saturated hetero ring, -lower alkylene-saturated hetero ring or -lower alkenylene-saturated hetero ring, X$^a$: single bond, —O—, —CO—, —S—, —SO$_2$—, —N(R$^0$)—, —N(R$^0$)CO—, —N(R$^0$)SO$_2$—, -lower alkylene-O—, -lower alkyllene-N(R$^0$)—, -lower alkylene-N(R$^0$)CO— or -lower alkylene-N(R$^0$)SO$_2$—, -lower alkylene-N(R$^0$)CO$_2$—, —N(CO—R$^0$)—, —N(SO$_2$-lower alkyl)-, —CON(R$^0$)—, -lower alkenylene-CO—, -lower alkenylene-CON(R$^0$)—, -lower alkenylene-CO$_2$—, —O—(CH$_2$)$_k$-cycloalkylene-(CH$_2$)$_m$—, —N(R$^0$)—(CH$_2$)$_k$-cycloalkylene-(CH$_2$)$_m$—, —CO—(CH$_2$)$_k$-cycloalkylene-(CH$_2$)$_m$—, —CON(R$^0$)—(CH$_2$)$_k$-cycloalkylene-(CH$_2$)$_m$— or —N(R$^0$)CO—(CH$_2$)$_k$-cycloalkylene-(CH$_2$)$_m$—, k and m: the same or different from each other, and each is 0, 1, 2, 3 or 4, wherein the saturated hetero rings in R$^3$ and R$^4$ may be substituted with 1 to 5 of lower alkyl, halogen, —OR$^0$, —S-lower alkyl, —S(O)-lower alkyl, —SO$_2$-lower alkyl, lower alkylene—OR$^0$, —N(R$^0$)$_2$, —CO$_2$R$^0$, —CON(R⁰)₂, —CN, —CHO, —SO₂N(R⁰)₂, —N(R⁰)—SO₂--lower alkyl, —N(R⁰)—CO—N(R⁰)₂, —N(R⁰)—CO₂-lower alkyl, —N(R⁰)—CO₂-cycloalkyl, —NH—C(=NH)—NH-lower alkyl, —NH—C(=N—CN)—NH-lower alkyl, saturated hetero ring (said hetero ring may be substituted with 1 to 5 substituents selected from lower alkyl, OH and lower alkylene-OH), heteroaryl, -lower alkylene- NH—C(=NN)—NH₂, —O-phenyl, —CO-phenyl, —N(R⁰)—CO-lower alkyl, —N(R⁰)—CO-lower alkylene —N(R⁰)₂, -lower alkylene—N(R⁰)—CO-lower alkylene—N(R⁰)₂, —CO—N(R⁰)-lower alkylene—N(R⁰)₂, —CO-lower alkylene—N(R⁰)₂, —CO-lower alkylene—CO₂R⁰, -lower alkylene—N(R⁰)₂, -lower alkylene—CO₂R⁰, -lower alkylene—CO—N(R⁰)₂, -lower alkylene—N(R⁰)—CO—lower alkyl, -lower alkylene—N(R⁰)—CO₂-lower alkyl, -lower alkylene—N(R⁰)—SO₂-lower alkyl, -lower alkylene-hetero ring (said hetero ring may be substituted with 1 to 5 substituents selected from lower alkyl, OH and lower alikylene—OH), -lower alkylene-O-lower alkylene-phenyl, =N—O—R⁰ or oxo, and phenyl and cycloalkyl may be substituted with 1 to 5 of lower alkyl, OH, O—lower alkyl or N(R⁰)₂, and wherein the lower alkylene in R³, R⁴ and Xᵃ may be substituted with 1 to 5 of —OR⁰, —CO₂R⁰, —CON(R⁰)₂, —N(R⁰)₂, —N(R⁰)COR⁰ or hetero ring, or R³ and R⁴ may together form *—N(R⁷)—(CH₂)₂—, *—(CH₂)₂—N(R⁷)—, *—CH₂—N(R⁷)—CH₂—, *—N(R⁷)—(CH₂)₃—, *—(CH₂)₃—N(R⁷)—, *—CH₂—N(R⁷)—(CH₂)₂—, *—(CH₂)₂—N(R⁷)—CH₂—, *—C(O)—N(R⁷)—(CH₂)₂—, *—(CH₂)₂—N(R⁷)—C(O)—, *—N(R⁷)—CH=CH—, *—CH=CH-7N(R⁷)—, *—N=CH—CH=CH—, *—CH=N—CH=CH—, *—CH=CH—N=CH—, *—CH=CH—CH=N—, *—N=CH—CH=N—, *—CH=N—N=CH—, *—N(R⁷)—N=CH—, *—CH=N—N(R⁷)—, *—O—CH₂—O—, *—O—(CH₂)₂—O—, *—O—(CH₂)₃—O—, *—O—(CH₂)₂—N(R⁷)—, *—(CH₂)₂—C(O)—, *—CH=CH—C(O)—O— or *—N=C(CF₃)—NH—, wherein * indicates bonding to the position shown by R³, R⁷: —H, -lower alkyl or —CO-lower alkyl, B: aryl which may have a substituent(s) or heteroaryl which may have a substituent(s), and R¹ and R²: the same or different from each other, and each represents H, lower alkyl or O-lower alkyl which may have a substituent(s)).

In addition, the present invention also relates to a novel diaminopyrimidinecarboxamide derivative represented by the following formula (Ib) or a pharmaceutically acceptable salt thereof, which is included in the compounds of the aforementioned formula (I), characterized in that it has at least one saturated hetero ring group in the R³ of formula (I).

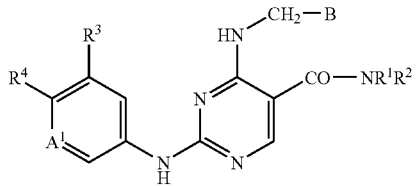

(Ib)

(symbols in the formula have the following meanings:

A¹: CR⁵ or N,

R⁵: —H, -lower alkyl, —O-lower alkyl or -halogen,

R³: -saturated hetero ring or —Xᵇ-saturated hetero ring,

Xᵇ: -lower alkylene-, —O—, —N(R⁰)—, —O-lower alkylene-, —S-lower alkylene-, —SO-lower alkylene-, —SO₂-lower alkylene-, —N(R⁰)-lower alkylene- or -lower alkylene-CO—, R⁰: the same or different from one another, and each represents H or a lower alkyl, R⁴: —H, -lower alkyl substituted with halogen, —OH, —NH—CHO, —CON(R⁰)₂, -lower alkylene substituted with halogen-OH, -lower alkylene-NH₂, -lower alkylene-NH-CONH₂, -lower alkylene-CO₂H, -lower alkylene-CO₂-lower alkyl, -lower alkylene-CN, —CH(lower alkylene-OH)₂ or —Xᵃ—R⁴ᵃ, Xᵃ: single bond, —O—, —CO—, —S—, —SO₂—, —N(R⁰)—, —N(R⁰)CO—, —N(R⁰)SO₂—, -lower alkylene-O—, -lower alkylene-N(R⁰)—, -lower alkylene-N(R⁰)CO— or -lower alkylene-N(R⁰)SO₂—, -lower alkylene-N(R⁰)CO₂—, —N(CO—R⁰)—, —N(SO₂-lower alkyl)-, —CON(R⁰)—, -lower alkylene-O—CO—, -lower alkenylene-CO—, -lower alkenylene-CON(R⁰)—, -lower alkenylene-CO₂—, —O—(CH₂)ₖ-cycloalkylene-(CH₂)ₘ—, —N(R⁰)—(CH₂)ₖ-cycloalkylene-(CH₂)ₘ—, —CO—(CH₂)ₖ-cycloalkylene-(CH₂)ₘ, —CON(R⁰)—(CH₂)ₖ-cycloalkylene-(CH₂)ₘ— or —N(R⁰)CO—(CH₂)ₖ-cycloalkylene-(CH₂)ₘ—, k and m: the same or different from each other, and each is 0, 1, 2, 3 or 4, R⁴ᵃ: lower alkyl, phenyl, heteroaryl, cycloalkyl, lower alkylene-phenyl, lower alkylene-heteroaryl, lower alkylene-OH, lower alkenyl, lower alkenylene-phenyl or lower alkenylene-heteroaryl, wherein the saturated hetero ring and heteroaryl in R³ and R⁴ᵃ may be substituted with 1 to 5 of lower alkyl, halogen, —OR⁰, —S-lower alkyl, —S(O)-lower alkyl, —SO₂-lower alkyl, lower alkylene-OR⁰, —N(R⁰)₂, —CO₂R⁰₁—CON(R⁰)₂, —CN, —CHO, —SO₂N(R⁰)₂, —N(R⁰)—SO₂-lower alkyl, —N(R⁰)—CO—N(R⁰)₂, —N(R⁰)—CO₂-lower alkyl, —N(R⁰)—CO₂-cycloalkyl, —NH—C(=NH)—NH-lower alkyl, —NH—C(=N—CN)—NH-lower alkyl, hetero ring (said hetero ring may be substituted with 1 to 5 substituents selected from lower alkyl, OH and lower alkylene-OH), -lower alkylene-NH—C(=NN)—NH₂, —O-phenyl, —CO-phenyl, —N(R⁰)—CO-lower alkyl, —N(R⁰)—CO-lower alkylene-N(R⁰)₂, -lower alkylene-N(R⁰)—CO-lower alkylene-N(R⁰)₂, —CO—N—(R⁰)—lower alkylene-N(R⁰)₂, —CO-lower alkylene-N(R⁰)₂, —CO-lower alkylene-CO₂R⁰, -lower alkylene-N(R⁰)₂, -lower alkylene-CO₂R⁰, -lower alkylene-CO—N(R⁰)₂, -lower alkylene-N(R⁰)—CO-lower alkyl, -lower alkylene-N(R⁰)—CO₂-lower alkyl, -lower alkylene-N(R⁰)—SO₂-lower alkyl, -lower alkylene-hetero ring (said hetero ring may be substituted with 1 to 5 substituents selected from lower alkyl, OH and lower alkylene-OH), -lower alkylene-O-lower alkylene-phenyl, =N —O—R⁰ or oxo, and phenyl and cycloalkyl may be substituted with 1 to 5 of lower alkyl, OH, O-lower alkyl or N(R⁰)₂, or the lower alkylene in R³, R⁴, R⁴ᵃ and Xᵃ may be substituted with 1 to 5 of —OR⁰, —CO₂R⁰, —CON(R⁰)₂, —N(R⁰)₂, —N(R⁰)COR⁰ or hetero ring, or R³ and R⁴ may together form *—N(R⁷)—(CH₂)₂—, *—(CH₂)₂—N(R⁷)—, *—CH₂—N(R⁷)—CH₂—, *—N(R⁷)—(CH₂)₃—, *—(CH₂)₃—N(R⁷)—, *—CH₂—N(R⁷)—(CH₂)₂—, *—(CH₂)₂—N(R⁷)—CH₂—, *—C(O)—N(R⁷)—(CH₂)₂—, *—(CH₂)₂—N(R⁷)—C(O)—, *—N(R⁷)—CH=CH—, *—CH=CH—N(R⁷)—, *—N=CH—CH=CH—, *—CH=N—CH=CH—, *—CH=CH—N=CH—, *—CH=CH—CH=N—, *—N=CH—CH=N—, *—CH=N—N=CH—, *—N(R⁷)—N=CH—, *—CH=N—N(R⁷)—, *—O—CH₂—

—O—, *—O—(CH₂)₂—, *—(CH₂)₃—O—, *—O—(CH₂)₂—N(R⁷)—, *—(CH₂)₂—C(O)—, *—CH=CH—C(O)—O— or *—N=C(CF₃)—NH—, wherein * indicates bonding to the position shown by R³, R⁷: —H-lower alkyl or —CO-lower alkyl, B: aryl which may have a substituent(s) or heteroaryl which may have a substituent(s), and R¹ and R²: the same or different from each other, and each represents H, lower alkyl or O-lower alkyl which may have a substituent(s)).

Further, the present invention also relates to a novel diaminopyrimidinecarboxamide derivative represented by the following formula (Ic) or a pharmaceutically acceptable salt thereof, which is included in the compounds of the aforementioned formula (I), characterized in that the amino group at 2-position is a (substituted phenyl)ethylamino group.

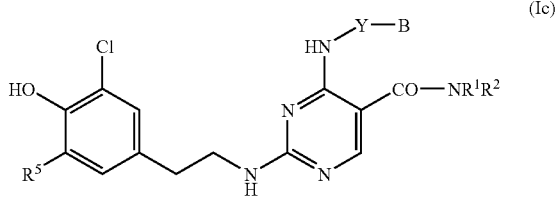

(symbols in the formula have the following meanings:

R⁵: —H or -halogen,

B: phenyl which may have 1 to 3 substituents selected from lower alkyl and halogen, Y: single bond or —CH₂—, and R¹ and R²: the same or different from each other, and each represents H or lower alkyl which may have a substituent(s)).

Furthermore, the present invention also relates to a medicament which comprises a novel diaminopyrimidinecarboxamide derivative represented by the aforementioned formula (Ia), (Ib) or (Ic) or a pharmaceutically acceptable salt thereof as the active ingredient, particularly a pharmaceutical composition which is effective as a preventive or therapeutic agent for respiratory diseases such as asthma, COPD and the like.

The present invention is described in detail in the following.

The terms "alkyl", "alkenyl", "alkynyl", "alkylene" and "alkenylene" as used herein mean straight chain form or branched form hydrocarbon chains. The "lower alkyl" is preferably a $C_{1-6}$ alkyl, more preferably a $C_{1-4}$ alkyl, further preferably $C_{1-3}$ alkyl such as methyl, ethyl, isopropyl or the like. The "lower alkylene" is preferably a $C_{1-6}$ alkylene, more preferably a $C_{1-4}$ alkylene, further preferably a $C_{1-2}$ alkylene. The "lower alkenyl" means that it has one or more double bonds at optional positions of a $C_{2-6}$ alkyl, The "lower alkynyl" means that it has one or more triple bonds at optional positions of a $C_{2-6}$ alkyl chain, and the "lower alkenylene" means that it has one or more double bonds at optional positions of a $C_{2-6}$ alkylene.

The "halogen" represents F, Cl, Br and I, preferably F, Cl and Br.

The "lower alkyl substituted with halogen" is a lower alkyl substituted with one or more halogen, preferably a $C_{1-2}$ alkyl having from 1 to 5 F, and its examples include fluoromethyl, difluoromethyl, trifluoromethyl and trifluoroethyl. The "lower alkylene substituted-with halogen" is a lower alkylene substituted with one or more halogen, preferably a $C_{1-3}$ alkylene having from 1 to 6 F.

Preferred as the "aryl group" is a monocyclic to tricyclic aryl group having from 6 to 14 carbon atoms. More preferred are phenyl and naphthyl groups. In addition, a five- to eight-membered cycloalkyl ring may be fused with phenyl group to form, for example, indanyl, tetrahydronaphthyl or the like. The "cycloalkyl group" is a cycloalkyl group having from 3 to 12 carbon atoms, and it may form a bridged ring or spiro-ring. Preferred are cycloalkyl groups having from 3 to 10 carbon atoms, and more preferred are cyclopropyl, cyclopentyl, cyclohexyl, cycloheptyl, adamantyl and norbornyl.

The "cycloalkylene" means a divalent group formed by removing one hydrogen atom at an optional position of "cycloalkyl group", and its examples include cyclohexane-1,4-diyl, cyclohexane-1,1-diyl, cyclopentane-1,1-diyl and the like.

The "saturated hetero ring" represents a 4- to 8-membered saturated monocyclic hetero ring group containing 1 to 4 hetero atoms selected from O, S and N, and a bicyclic or tricyclic hetero ring group in which said saturated monocyclic hetero rings are fused each other, or a monocyclic hetero ring is fused with a cycloalkyl ring(s). It may form an oxide or dioxide through the oxidation of S or N as a ring atom, or may form a bridged ring or a spiro-ring. Their preferred examples include saturated hetero rings such as piperidyl, morpholinyl, thiomorpholinyl, piperazinyl, pyrazolidinyl, imidazolidinyl, pyrrolidinyl, oxazolidinyl, thiazolidinyl, homopiperazinyl, tetrahydrofuranyl, tetrahydropyranyl, dioxolanyl, homomorpholinyl and the like, or bridged rings such as 2,5-diazabicyclo[2,2,1]heptyl, 2,8-diazaspiro[4,5]decane and the like.

The "heteroaryl" represents a 5- or 6-membered monocyclic heteroaryl containing 1 to 4 hetero atoms selected from O, S and N, and a bicyclic or tricyclic hetero ring group in which (i) heteroaryl groups each other, (ii) heteroaryl and cycloalkyl ring, (iii) heteroaryl and benzene ring, (iv) saturated hetero ring and heteroaryl or (v) saturated hetero ring and benzene ring are fused. It may form an oxide or dioxide through the oxidation of S or N as a ring atom, or may form a bridged ring or spiro-ring. Preferably, pyridyl, pyridazinyl, pyrimidinyl, pyrazinyl, furyl, thienyl, pyrrolyl, oxazolyl, isoxazolyl, oxadiazolyl, thiazolyl, thiadiazolyl, imidazolyl, triazolyl, tetrazolyl, benzofuranyl, benzothienyl, benzoxazolyl, benzoimidazolyl, benzothiazolyl, chromanyl, quinolinyl, quinazolinyl, quinoxalinyl, cinnolinyl, pyrrolidinyl and the like may be exemplified.

The "hetero ring group" includes the aforementioned "saturated hetero ring" and "heteroaryl" and "partially unsaturated hetero ring" such as dihydropyridyl, dihydropyrrolyl, dihydroxazolyl, dihydrothiazolyl, dihydroimidazolyl, tetrahydropyrimidinyl and the like.

The term "which may have a substituent(s)" means "not substituted" or "substituted with the same or different 1 to 5 substituents".

The substituent in the "cycloalkyl which may have a substituent(s)" is a group which may be used as a substituent of these rings, and is preferably a group selected from the following group G.

Group G: -lower alkyl, —OH, —O-lower alkyl, -aryl, -hetero ring and oxo.

The substituent in the "aryl which may have a substituent" and "hetero ring which may have a substituent(s)" is a group which may be used as a substituent(s) of these rings, and is preferably a group selected from the following group P.

Group P: -lower alkyl which may be substituted with a group of group Q, -lower alkyl substituted with halogen, -halogen, —OH, —CN, —O-(lower alkyl which may be substituted with a group of group Q), —O-lower alkyl substituted with halogen, —S-lower alkyl, —NH₂, —NH-(lower alkyl which may be substituted with a group of group Q), —N-(lower alkyl which may be substituted with a group of group Q)$_2$, —CO-lower alkyl, -lower alkylene-OH, -lower alkylene-hetero ring, -lower alkylene-phenyl, -hetero ring, —CO-hetero ring, —CHO, —CO$_2$H, —CO$_2$ lower alkyl, -nitro, —SO-lower alkyl, —SO$_2$ lower alkyl and —NHCO-(lower alkyl which may be substituted with a group of group Q). In this connection, hetero ring and phenyl may be substituted with -lower alkyl, -halogen or —OH.

The substituent in the "lower alkyl which may have a substituent(s)" is a group which may be used as a substituent(s) of these rings, and is preferably a group selected from the following group Q.

Group Q: —OH, —O-lower alkyl, —S-lower alkyl, —NH$_2$, —NH-lower alkyl, —N(lower alkyl)$_2$, —CO$_2$H, —CONH$_2$, -aryl and -hetero ring. In this connection, aryl may be substituted with -lower alkyl, -halogen or —OH, and hetero ring may be substituted with -lower alkyl, —OH or oxo.

Preferred compound among the compound (I) useful as the active ingredient of the present invention is a compound represented by the formula (Ia), formula (Ib) or formula (Ic), and in the other preferred embodiment, R$^3$ and R$^4$ together form *—N(R$^7$)—(CH$_2$)$_2$—, *—(CH$_2$)$_2$—N(R$^7$)—, *I—N(R$^7$)—(CH$_2$)$_3$—, *—(CH$_2$)$_3$—N(R$^7$)—, *—CH$_2$—N(R$^7$)—(CH$_2$)$_2$— or *—(CH$_2$)$_2$—N(R$^7$)—CH$_2$—. In this case, preferred as R$^7$ is H, methyl or acetyl.

Preferred embodiment of the compound (Ia) is shown in the following:

A$^1$ is preferably CH, C-halogen, C—(O-lower alkyl) or N, more preferably CH, C-halogen or C—(O-lower alkyl), further preferably CH or C-halogen, most preferably CH.

R$^3$ is preferably —R$^0$, -lower alkyl substituted with halogen, -halogen, —OR$^0$, -saturated hetero ring, -lower alkylene-heteroaryl or -lower alkylene-saturated hetero ring, more preferably —H, -halogen, —OH, —O—C$_{1-3}$ alkyl or -lower alkylene-saturated hetero ring, further preferably —H, —Cl, —F or —Br, wherein said saturated hetero ring may be substituted with 1 to 5 of lower alkyl, OH, O-lower alkyl or oxo.

R$^4$ is preferably —X$^a$-saturated hetero ring;

wherein X$^a$ is preferably single bond, —O—, —CO—, —S—, —SO$_2$—, —N(R$^0$)—, —N(R$^0$)CO—, -lower alkylene-O—, -lower alkylene-N(R$^0$)— or -lower alkylene-N(R$^0$)CO—, more preferably single bond, —O—, —CO—, —S—, —N(R$^0$)—, —N(R$^0$)CO— or -lower alkylene-N(R$^0$)CO—;

more preferred is —O-piperidyl, —O-pyrrolidyl, —O-quinuclidinyl, —O-tetrahydrofuranyl, —O-tetrahydropyranyl, —CO-morphorinyl, —CO-piperidyl, —CO-piperazinyl, —S-tetrahydrofuranyl, —SO$_2$-piperidyl, —SO$_2$-piperazinyl, —C$_{1-4}$ alkylene-N(Me)-piperidyl, —C$_{1-4}$ alkylene-N(Me)-tetrahydropyranyl, —C$_{1-4}$ alkylene-pyrrolidyl, —C$_{1-4}$ alkylene-piperidyl, —C$_{1-4}$ alkylene-piperazinyl, —C$_{1-4}$ alkylene-morpholinyl, —C$_{1-4}$ alkylene-thiomorpholinyl, —O—C$_{1-4}$ alkylene-pyrrolidyl, —O—C$_{1-4}$ alkylene-piperidyl, —O—C$_{1-4}$ alkylene-piperazinyl, —O—C$_{1-4}$ alkylene-morpholinyl, —O—C$_{1-4}$ alkylene-thiomorpholinyl, -piperidyl, -morpholinyl, -thiomorpholinyl, homomorpholinyl, 2,5-diazabicyclo[2,2,1]heptyl, -piperazinyl or homopiperazinyl. In this case, ethylene or dimethylethylene is particularly desirable as the C$_{1-4}$ alkylene. In addition, the aforementioned hetero ring including piperidyl, piperazinyl, homopiperazinyl, morpholinyl, thiomorpholinyl, pyrrolidyl, tetrahydrofuranyl and tetrahydropyranyl may be substituted with lower alkyl, OH, O-lower alkyl, —CO-lower alkylene-N (lower alkyl)$_2$, lower alkylene-NHCO-lower alkylene-N (lower alkyl)$_2$, -lower alkylene-N(lower alkyl)$_2$, lower alkylene-CO$_2$H, —CO$_2$H, lower alkylene-CO$_2$-lower alkyl, —CO$_2$-lower alkyl, lower alkylene-CONH$_2$, —CONH$_2$, lower alkylene-HNCONH$_2$, lower alkylene-NH—SO$_2$ lower alkyl, lower alkylene-N(lower alkyl)-SO$_2$ lower alkyl, -lower alkylene-OH or oxo.

B is preferably phenyl, indolyl, indazolyl, furyl or thienyl, and said phenyl, indolyl, indazolyl, furyl and thienyl may have a substituent(s) selected from the aforementioned group P.

Regarding R$^1$ and R$^2$, preferred is a case in which R$^1$ is H and R$^2$ is H or lower alkyl which may have a substituent(s) selected from the aforementioned group Q, more preferred is a case in which both of R$^1$ and R$^2$ are H.

Accordingly, as the compound (Ia), a compound consisting of a combination of the aforementioned preferred groups is more desirable.

Preferred embodiment of the compound (Ib) is shown in the following:

A$^1$ is preferably CH, C-halogen, C—(O-lower alkyl) or N. More preferably CH or C-halogen, and most preferably CH.

R$^3$ is preferably -saturated hetero ring, —O-saturated hetero ring, —N(R$^0$)-saturated hetero ring or -lower alkylene-saturated hetero ring, more preferably -lower alkylene-saturated hetero ring including nitrogen atom, wherein said saturated hetero ring including nitrogen atom may be unsubstituted or substituted with 1 to 5 of lower alkyl, OH, O-lower alkyl or oxo.

R$^4$ is preferably —H, —OH, —NH—CHO, —CON(R$^0$)$_2$, -lower alkylene substituted with halogen-OH, -lower alkylene-NH$_2$, -lower alkylene-NHCONH$_2$, -lower alkylene-CO$_2$H, -lower alkylene-CO$_2$-lower alkyl, -lower alkylene-CN, or —CH(lower alkylene-OH)$_2$, or a group represented by a formula —X$^a$—R$^{4a}$, wherein preferred as X$^a$ is single bond, —O—, —CO—, —S—, —SO$_2$—, —N(R$^0$)—, —N(R$^0$)CO—, -lower alkylene-O—, -lower alkylene-N(R$^0$)— or -lower alkylene-N(R$^0$)CO—, and more preferred is single bond, —O—, —CO—, —N(R$^0$)—, —N(R$^0$)CO— or -lower alkylene-N(R$^0$)CO—;

more preferred is —OH, —CON(R$^0$)$_2$, -lower alkylene substituted with halogen-OH, -lower alkylene-CN or —CH (lower alkylene-OH)$_2$, or a group represented by a formula —X$^a$—R$^{4a}$, further preferred is —CH(lower alkylene-OH)$_2$ or a group represented by the formula —X$^a$—R$^{4a}$ and most preferred is —OH, —C$_{1-4}$ alkylene-OH, —CH$_2$N(Me)$_2$, —C$_{1-4}$ alkylene-N(Me)-C$_{5-6}$ cycloalkyl or —CH(CH$_2$OH)$_2$. In this case, ethylene or dimethylethylene is particularly desirable as the C$_{1-4}$ alkylene. In addition, the aforementioned cycloalkyl may be substituted with lower alkyl, OH, O-lower alkyl or —N(lower alkyl)$_2$.

B is preferably phenyl, indolyl, indazolyl, furyl or thienyl, and said phenyl, indolyl, indazolyl, furyl and thienyl may have a substituent selected from the aforementioned group P.

Regarding R$^1$ and R$^2$, preferred is a case in which R$^1$ is H and R$^2$ is H or lower alkyl which may have a substituent selected from the aforementioned group Q, more preferred is a case in which both of R$^1$ and R$^2$ are H.

Accordingly, as the compound (Ib), a compound consisting of a combination of the aforementioned preferred groups is more desirable.

Preferred embodiment of the compound (Ic) is shown in the following:

R$^5$ is preferably —H, —Cl, —F or —Br, more preferably —H or —Cl.

B is preferably H, $C_{1-6}$ alkyl substituted with halogen, aryl which may have a substituent(s), cycloalkyl which may have a substituent(s) or hetero ring which may have a substituent(s), more preferably phenyl, $C_{3-8}$ cycloalkyl, indolyl, indazolyl, furyl, thienyl, adamantyl, norbornyl or tetrahydrofuranyl, and said phenyl, indolyl, indazolyl, furyl and thienyl may have a substituent(s) selected from the aforementioned group P, and the $C_{3-8}$ cycloalkyl may have a substituent(s) selected from the aforementioned group G.

Y is preferably single bond, or a lower alkylene group which may be substituted with OH or O—$C_{1-2}$ alkyl, more preferably single bond or a $C_{1-6}$ alkylene group. Further preferred is single bond, methylene, methylmethylene or ethylene. Alternatively, in case that B is H, preferred as Y—B is 2-propyl, 2-methylpropyl, tert-butyl, 2,2-dimethylpropyl or 3-methylbutyl.

Preferable $R^1$ and $R^2$ include those in which $R^1$ is H and $R^2$ is H or lower alkyl which may have a substituent(s) selected from the aforementioned group Q, more preferably, those in which both of $R^1$ and $R^2$ are H.

Accordingly, as the compound (Ic), a compound consisting of a combination of the aforementioned preferred groups is more desirable.

Particularly desirable compounds regarding the compound (I) are the following compounds: -4-benzylamino-2-[(4-morpholin-4-ylphenyl)amino]pyrimidine-5-carboxamide, 2-[(4-morpholin-4-ylphenyl)amino]-4-[(2,3,6-trifluorobenzyl)amino]pyrimidine-5-carboxamide, 4-[(2,6-difluorobenzyl)amino]-2-[(4-morpholin-4-ylphenyl)amino]pyrimidine-5-carboxamide, 4-[(2,5-difluorobenzyl)amino]-2-[(4-morpholin-4-ylphenyl)amino]pyrimidine-5-carboxamide, 4-[(2-methoxybenzyl)amino]-2-[(4-morpholin-4-ylphenyl)amino]pyrimidine-5-carboxamide, 4-[(2-fluoro-6-methoxybenzyl)amino]-2-[(4-morpholin-4-ylphenyl)amino]pyrimidine-5-carboxamide, 2-({4-[(1-methylpiperidin-3-yl)oxy]phenyl}amino)-4-[(2,3,6-trifluorobenzyl)amino]pyrimidine-5-carboxamide, 2-([4-(1-azabicyclo[2.2.2]oct-3-yloxy)phenyl]amino)-4-[(2,3,6-trifluorobenzyl)amino]pyrimidine-5-carboxamide, 2-[(4-methyl-3,4-dihydro-2H-1,4-benzoxazin-7-yl)amino]-4-[(2,3,6-trifluorobenzyl)amino]pyrimidine-5-carboxamide, 2-({4-[4-(2-amino-2-oxoethyl)piperazin-1-yl]phenyl}amino)-4-[(2,3,6-trifluorobenzyl)amino]pyrimidine-5-carboxamide, 2-{[4-(2-morpholin-4-ylethoxy)phenyl]amino}-4-[(2,3,6-trifluorobenzyl)amino]pyrimidine-5-carboxamide, 2-{[4-(β-D-glucopyranosyloxy)phenyl]amino}-4-[(2,3,6-trifluorobenzyl)amino]pyrimidine-5-carboxamide, 4-benzylamino-2-{[2-(3-chloro-4-hydroxyphenyl)ethyl]-amino}pyrimidine-5-carboxamide, 4-benzylamino-2-{[2-(3,5-dichloro-4-hydroxyphenyl)ethyl]amino}pyrimidine-5-carboxamide, 2-[(4-morpholin-4-ylphenyl)amino]-4-[(2-thienylmethyl)amino]pyrimidine-5-carboxamide, 4-{[(3-chloro-2-thienyl)methyl]amino}-2-[(4-morpholin-4-ylphenyl)amino]pyrimidine-5-carboxamide and 2-{[3-(2-morpholin-4-ylethyl)phenyl]amino}-4-[(2,3,6-trifluorobenzyl)amino]pyrimidine-5-carboxamide.

The compound (I) and novel compounds (Ia), (Ib) and (Ic) ("compound (I)" hereinafter) useful as the active ingredient of the present invention may exist in the form of geometrical isomers and tautomers depending on the kind of substituents, and their separated forms or mixtures are also included in the present invention. Also, since the compound (I) has asymmetric carbon atom in some cases, isomers based on the asymmetric carbon atom may be present. Mixtures and isolated forms of these optical isomers are included in the present invention. In addition, compounds prepared by labeling the compound (I) with radioisotopes are included in the present invention.

In some cases, the compound (I) forms an acid addition salt or, depending on the kind of substituents, a salt with a base, and such salts are included in the present invention with the proviso that they are pharmaceutically acceptable salts. Their illustrative examples include acid addition salts with inorganic acids such as hydrochloric acid, hydrobromic acid, hydroiodic acid, sulfuric acid, nitric acid, phosphoric acid and the like and with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like, salts with inorganic bases such as sodium, potassium, magnesium, calcium, aluminum and the like or with organic bases such as methylamine, ethylamine, ethanolamine, lysine, ornithine and the like, ammonium salts and the like. Further, the present invention also includes various hydrates, solvates and polymorphic substances of the compound (I) and its pharmaceutically acceptable salts.

In addition, a pharmacologically acceptable prodrug is also included in the present invention. The pharmacologically acceptable prodrug is a compound having the group of the present invention which may be converted into $NH_2$, OH, $CO_2H$ or the like by solvolysis or under physiological conditions. As the groups which can form prodrugs, the groups described in *Prog. Med.*, 5, 2157-2161 (1985) and "Iyakuhin-no Kaihatsu (Development of Medicaments)" (written in Japanese, Hirokawa Shoten) vol. 7 Bunshi Sekkei (Molecular Design) 163-198 may be exemplified.

(Production Methods)

The compound (I) or a pharmaceutically acceptable salt thereof may be produced by employing various conventionally known synthesis methods, making use of the characteristics based on its basic skeleton or the kind of substituents. In that case, depending on the kind of functional group, there is a case in which it is effective from a production technical point of view to protect said functional group or replace it by a group which may be easily converted into said functional group at a stage of the material or an intermediate. Examples of such a functional group include amino group, hydroxyl group, carboxyl group and the like, examples of their protecting groups include the protecting groups described in "Protective Groups in Organic Synthesis (3rd edition, 1999)" edited by Greene (T. W. Greene) and Wuts (P. G. M. Wuts), and these may be optionally selected and used in response to the reaction conditions. In such a method, a desired compound may be obtained by introducing said protecting group and carrying out the reaction, and then removing the protecting group as occasion demands, or converting it into a desired group. In addition, a prodrug of the compound (I) may be produced by introducing a specified group at a stage of the material or an intermediate similar to the case of the aforementioned protecting group, or carrying out a reaction using the obtained compound (I). The reaction may be carried out by employing a conventional method known to those skilled in the art such as general esterification, amidation, carbamation, dehydration or the like.

The following describes typical production methods of the compounds of the present invention regarding the compound of formula (I), and the compounds of formulae (Ia), (Ib) and (Ic) can also be produced in the same manner.

Production Method A Substitution Reaction (1)

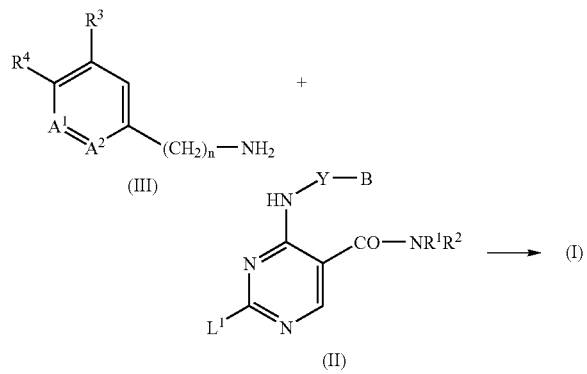

(In the formula, $L^1$ represents a leaving group. The same shall apply hereinafter.)

This production method is a method in which the compound (I) is obtained by allowing a pyrimidine compound (II) to react with an amine compound (III). In this case, examples of the leaving group of $L^1$ include a halogen atom, methylsufanyl, methylsulfinyl, methylsulfonyl, 1H-benzotriazol-1-yloxy, methylsulfonyloxy, p-toluenesulfonyloxyl trifluoromethanesulfonyloxy and the like.

The reaction may be carried out without solvent or in a solvent inert to the reaction such as aromatic hydrocarbon (e.g., benzene, toluene, xylene or the like), ether (e.g., diethyl ether, tetrahydrofuran (THF), dioxane or the like), halogenated hydrocarbon (e.g., dichloromethane, 1,2-dichloroethane, chloroform or the like), N,N-dimethylformamide (DMF), dimethylacetamide (DMA), N-methylpyrrolidone (NMP), ethyl acetate, acetonitrile or the like, using the compounds (II) and (III) in equimolar basis or one of them in an excess amount, and at room temperature to under heat reflux. The reaction temperature may be optionally set in accordance with the compounds. Depending on the compounds, it is sometimes advantageous to carry out the reaction in the presence of an organic base (preferably diisopropylethylamine, N-methylmorpholine, pyridine or 4-(N,N-dimethylamino)pyridine) or a metal base (preferably potassium carbonate or sodium hydroxide). Also, depending on the compounds, it is sometimes advantageous to carry out the reaction under an acidic condition (in the presence of 4 M hydrogen chloride/1,4-dioxane solution, 4 M hydrogen chloride/ethyl acetate solution or the like) or in the presence of a fluoride ion (potassium fluoride, cesium fluoride, tetrabutylammonium fluoride or the like).

In this connection, in case that the compound (I) has a primary or secondary amino group, it may be produced by protecting amino groups of the compound (II) and compound (III) as the material compounds in advance with a protecting group, carrying out said substitution reaction and then removing the protecting group. The protecting group may be optionally selected from the protecting groups described in the aforementioned "Protective Groups in Organic Synthesis".

Production Method B Substitution Reaction (2)

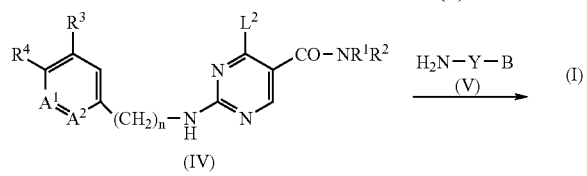

(In the formula, $L^2$ represents a leaving group. The same shall apply hereinafter.)

This production method is a method in which the compound (I) is obtained by allowing a pyrimidine compound (IV) to react with an amine compound (V), and it may be produced in the same manner as the method described in the aforementioned Production Method A. In this case, a group similar to the aforementioned leaving group $L^1$ may be used as the leaving group $L^2$.

Production Method C Amidation Reaction

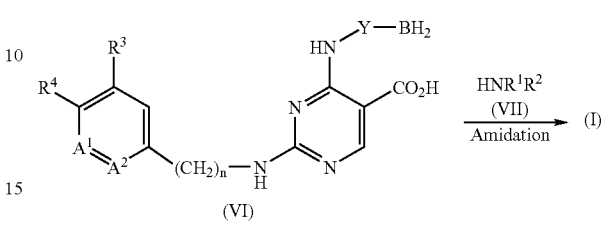

This production method is a method in which the compound (I) is obtained through the amidation of a carboxylic acid derivative (VI).

A free carboxylic acid or a reactive derivative thereof may be used in this reaction as the carboxylic acid derivative (VI), and examples of said reactive derivative include acid halides (acid chloride, acid bromide and the like), acid anhydrides (mixed anhydride obtained by the reaction with ethyl chlorocarbonate, benzyl chlorocarbonate, phenyl chlorocarbonate, p-toluenesulfonic acid, isovaleric acid and the like, or symmetric acid anhydrides), activated esters (esters which may be prepared using phenol, 1-hydroxybenzotriazole (HOBt), N-hydroxysuccinimide (HONSu) or the like that may be substituted with an electron withdrawing group such as a nitro group, a fluorine atom or the like), a lower alkyl ester, an acid azide and the like. These reactive derivatives may be produced in the usual way.

When a free carboxylic acid is used, it is desirable to use a condensing agent (such as (N,N'-dicyclohexylcarbodiimide (DCC), 1-[3-(dimethylamino)propyl]-3-ethylcarbodiimide (WSC), 1,1'-carbonylbisimidazole (CDI), N,N'-disuccinimidyl-carbonate, Bop reagent (Aldrich, USA), 2-(1H-benzotriazol-1-yl) -1,1,3,3-tetramethyluronium tetrafluoroborate (TBTU), diphenyl phosphate azide (DPPA), phosphorus oxychloride, phosphorus trichloride, triphenylphosphine/N-bromosuccinimide or the like), further using an additive agent (e.g., HONSu, HOBt or the like) as occasion demands.

The reaction is carried out using the carboxylic acid derivative (VI) and an amine (VII) in equimolar basis or one of them in an excess amount, in an inert solvent such as an aromatic hydrocarbon, a halogenated hydrocarbon, an ether, DMF, DMA, NMP, ethyl acetate, acetonitrile or the like, under cooling to heating, preferably from −20° C. to 60° C. Depending on the kind of reactive derivatives, it is sometimes advantageous in effecting smooth progress of the reaction to carry out the reaction in the presence of a base (preferably triethylamine, diisopropylethylamine, N-methylmorpholine, pyridine, 4-(N,N-dimethylamino)pyridine or the like). Pyridine can also serve as the solvent.

Production Method D Solid Phase Synthesis

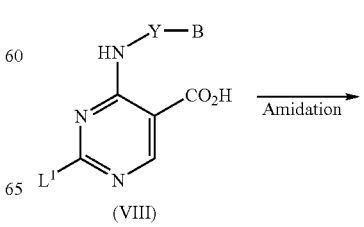

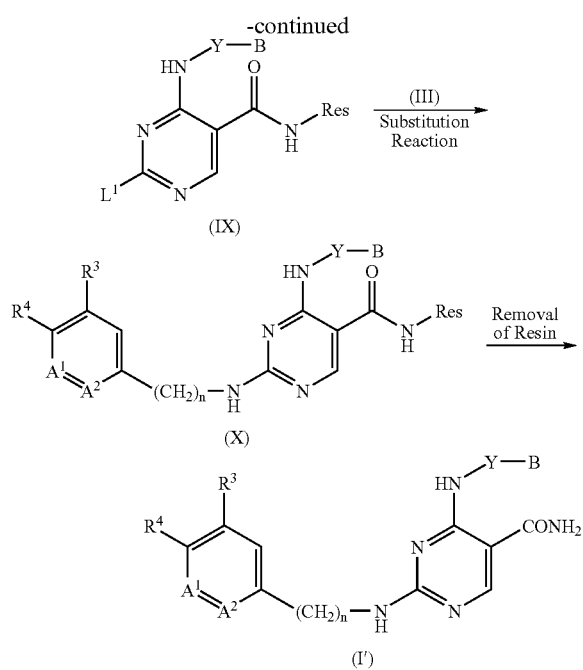

(In the formula, Res represents a resin for solid phase synthesis. The same shall apply hereinafter.)

This production method is a method producing by a solid phase synthesis method which consists of the following three steps.

(1) Fixation to a Resin (Amidation)

A carboxylic acid compound (VIII) and a resin for solid phase synthesis use having amino termini (e.g., an amino (methyl) resin, Rink amide resin or the like) are condensed in the same manner as in the aforementioned Production Method C.

(2) Substitution Reaction

The production is effected by carrying out a substitution reaction in the same manner as in Production Method A using the amine compound (III).

(3) Removal of the Resin

A compound (I') is produced by eliminating the resin from a compound (X). The reaction is carried out without solvent or in a solvent inert to the reaction (e.g., an aromatic hydrocarbon, an ether, a halogenated hydrocarbon, an alcohol, DMF, DMA, NMP, pyridine, dimethyl sulfoxide (DMSO), ethyl acetate, acetonitrile or the like), by treating with a mineral acid (e.g., hydrochloric acid, hydrobromic acid or the like) or an organic acid (e.g., trifluoroacetic acid or the like). It is advantageous in some cases to catty out the reaction in the presence of additive agent (e.g., difluoroethanol, triethylsilane, triisopropylsilane, (thio)anisole or the like).

Production Method E Other Production Methods

The compounds of the present invention having various functional groups such as amido group, ureido group, alkylamino group and the like can also be produced by using the compounds of the present invention having corresponding amino group and the like as the materials and employing a method obvious to those skilled in the art, a conventionally known production method or a modified method thereof. For example, the following reactions may be employed.

E-1: Amidation

Various amide compounds may be produced by allowing various carboxylic acid compounds or reactive derivatives thereof to react with a compound of the present invention having amino group. The aforementioned method Production Method C may be employed in this reaction. In addition, various sulfonamide derivatives may be produced by the use of various sulfonic acid derivatives (reactive derivatives such as sulfonic acid halides, sulfonic acid anhydrides and the like are desirable) instead of the carboxylic acid compounds.

E-2: Ureation

They may be produced by allowing ureation agents such as a cyanic acid derivative (e.g., sodium cyanate, potassium cyanate or the like), an isocyanate derivative, urea, cyanogen bromide and the like to react with the compounds of the present invention having amino group, without solvent or in an solvent inert to the reaction (e.g., an aromatic hydrocarbon, an ether, a halogenated hydrocarbon, an alcohol, water, DMF, DMA, NMP, pyridine, DMSO, ethyl acetate, acetonitrile or the like). These solvents may be used alone or as a mixture of two or more. It is sometimes advantageous in effecting smooth progress of the reaction to carry out the reaction in the presence of an acid (e.g., acetic acid, hydrochloric acid or the like) or a base (e.g., sodium hydroxide, potassium hydroxide or the like). The reaction may be carried out under cooling to heating reflux, and the reaction temperature may be optionally set depending on the compound.

E-3: Alkylation (1)

Alkyl groups may be introduced by allowing compounds having amino group to react with various alkylating agents (e.g., alkyl halides, alkyl sulfonic acid esters and the like) in the usual way. In addition, in case that a secondary amine is produced from a primary amine, a method in which a material is once made into a trifluoroacetylamino form, alkylated and then hydrolyzed (*Tetrahedron Letters*, 1978, 4987 and the like) may be employed.

E-4 Alkylation (2)

Alkylated compounds may be produced by subjecting compounds having amino group to a reductive alkylation with various carbonyl compounds. The reaction may be carried out by employing a method described, for example, in "Jikken Kagaku Koza (Experimental Chemistry Course) (Maruzen)" edited by The Chemical Society of Japan (4th edition, vol. 20, 1992, 300).

E-5: Oxidation

Oxide compounds may be obtained by treating compounds having tertiary amino groups or nitrogen-containing aromatic rings (e.g., pyridine and the like) with various oxidizing agents. The reaction may be carried out by employing a method described, for example, in "Jikken Kagaku Koza (Maruzen)" edited by The Chemical Society of Japan (4th edition, vol. 23, 1991, 271).

E-6: Reduction

A compound having amino group may be produced by subjecting a compound having oxidoamino group to a reductive treatment (e.g., reaction with sodium hydrogen sulfite or the like).

Production Method F Production method of Material Compounds

Material compounds to be used in the production of the compound (I) may be produced in the usual way, for example, using conventionally known reactions shown in the following synthesis pathway.

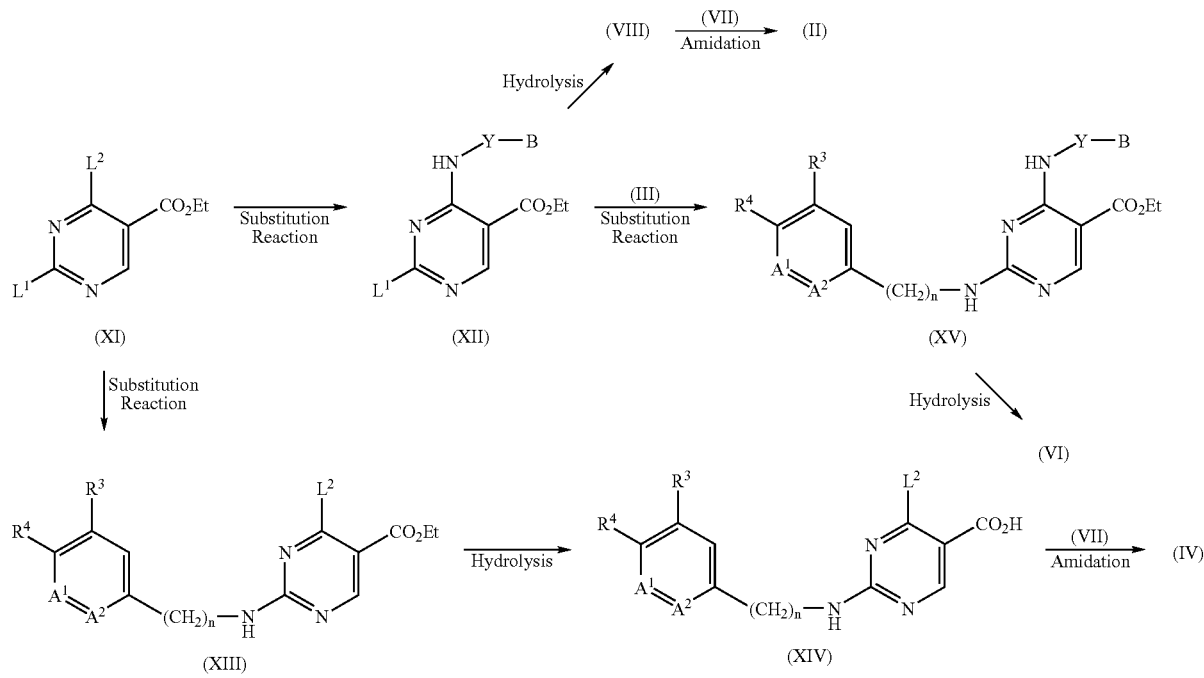

In the above reaction scheme, the substitution reaction may be carried out in the same manner as in the aforementioned Production Method A or B, and the amidation in the same manner as in the aforementioned Production Method C, respectively. The carboxyl group deprotection condition described in the aforementioned "Protective Groups in Organic Synthesis" may be applied to the hydrolysis, and other alkyl ester, benzyl ester and the like can also be used instead of the ethyl ester.

The reaction products obtained by the aforementioned respective production methods may be isolated and purified as free compounds, salts thereof or various solvates such as hydrate and the like. The salts may be produced by subjecting to general salt forming treatments.

Isolation and purification may be carried out by employing general chemical operations such as extraction, concentration, evaporation, crystallization, filtration, recrystallization, various types of chromatography and the like.

Various types of isomers may be isolated in the usual way making use of a physicochemical difference between isomers. For example, optical isomers may be separated by a general optical resolution method such as fractional crystallization or chromatography. In addition, optical isomers can also be produced from an appropriate optically active material compound.

INDUSTRIAL APPLICABILITY

As is also confirmed by the following Examples, the compound (I) useful as the active ingredient of the present invention has superior inhibitory activity for STAT 6 activation and is useful as an agent for preventing or treating respiratory diseases (asthma, CODP and the like) and allergic diseases (rhinitis, dermatitis and the like), in which STAT 6 is concerned.

In addition, since the compound (I) has the potent inhibitory activity for STAT 6 activation in comparison with the inhibitory activity for immunocyte activation by an antigen receptor stimulation and have compounds having a selectivity of 100 times or more, it is useful as the aforementioned preventive or therapeutic agent having less action upon the immunosuppression function. In this connection, the immunocyte activation inhibition by an antigen receptor stimulation may be evaluated, for example, based on the inhibition of intracellular calcium concentration increase in a B cell strain (RAMOS cell) by anti-IgM antibody stimulation and the inhibition of IL-2 production from a mouse spleen-derived T cell by anti-CD3 antibody stimulation.

The pharmaceutical preparation which contains one or two or more of the compounds (I) or salts thereof as the active ingredient is prepared using a carrier, a filler and other additives generally used in preparing medicaments.

Its administration may be in the form of either oral administration through tablets, pills, capsules, granules, powders, solutions and the like, or parenteral administration through injections such as intravenous injections, intramuscular injections or the like, suppositories, percutaneous preparations, transnasal preparations, inhalations and the like. The dose is optionally decided in response to each case, by taking into consideration symptoms, age, sex and the like of each subject to be administered, but is generally from 0.001 mg/kg to 100 mg/kg per day per adult in the case of oral administration, and this is administered once a day or by dividing into 2 to 4 daily doses, or is within the range of from 0.0001 mg/kg to 10 mg/kg per day per adult in the case of intravenous injection and this is administered once a day or dividing into two or more daily doses. In addition, in the case of transnasal administration, this is administered generally within the range of from 0.0001 mg/kg to 10 mg/kg per day per adult, once a day or dividing into two or more daily doses, and in the case of inhalation, this is administered generally within the range of from 0.0001 mg/kg to 1 mg/kg per day per adult, once a day or dividing into two or more daily doses.

As a solid composition of the present invention for oral administration, tablets, powders, granules and the like are used. In such a solid composition, one or more active substances are mixed with at least one inert excipient such as lactose, mannitol, glucose, hydroxypropylcellulose, microcrystalline cellulose, starch, polyvinyl pyrrolidone, aluminum magnesium silicate or the like. In the usual way, this composition may contain inactive additives such as a lubricant (e.g., magnesium stearate or the like), a disintegrating agent (e.g., carboxymethylstarch sodium or the like), and a solubilization assisting agent. As occasion demands, tablets or pills may be coated with a sugar coating or a film of a gastric or enteric coating agent.

The liquid composition for oral administration includes pharmaceutically acceptable emulsions, solutions, suspensions, syrups, elixirs and the like and contains a generally used inert solvent such as purified water or ethanol. In addition to the inert solvent, this composition may contain auxiliary agents such as a solubilizing agent, a moistening agent and a suspending agent, as well as a sweetener, a correctives, an aromatic or an antiseptic.

The injections for parenteral administration includes aseptic aqueous or non-aqueous solutions, suspensions and emulsions. The aqueous solvent includes, for example, distilled water for injection and physiological saline. The non-aqueous solvent includes, for example, propylene glycol, polyethylene glycol, plant oil (e.g., olive oil or the like), alcohol (e.g., ethanol or the like), polysorbate 80 (trade name) and the like. Such a composition may further contain a tonicity agent, an antiseptic, a moistening agent, an emulsifying agent, a dispersing agent, a stabilizing agent, a solubilization assisting agent and the like. These are sterilized, for example, by filtration through a bacteria retaining filter, blending of a germicide or irradiation. Alternatively, a sterile solid composition is produced, which may be used by dissolving or suspending in sterile water or other sterile solvent for injection prior to its use.

In the case of inhalations and transmucosal preparations such as transnasal preparations, those in the solid, liquid or semi-solid state are used, and they may be produced in accordance with conventionally known methods. For example, excipients (e.g., lactose, starch and the like), and also a pH adjusting agent, an antiseptic, a surfactant, a lubricant, a stabilizer, a thickener and the like, may be optionally added. An appropriate device for inhalation and exhalation may be used for the administration. For example, using a conventionally known device or sprayer such as a measuring administration inhalation device, a compound may be administered alone or as a powder of a prescribed mixture, or as a solution or suspension in combination with a pharmaceutically acceptable carrier. A dry powder inhalation device or the like may be for a single or multiple administration use, and a dry powder or powder-containing capsules may be used. Alternatively, it may be a pressure aerosol sprayer type or the like which uses an appropriate propellant such as chlorofluoroalkane, hydrofluoroalkane or carbon dioxide or the like appropriate gas.

BEST MODE FOR CARRYING OUT THE INVENTION

The following illustratively describes the present invention based on Examples, but these do not limit the scope of the present invention. Production methods of the material compounds are shown in Reference Examples. In addition, production methods of compounds which are included in the formula (I) but not included in the formula (Ia), (Ib) or (Ic) are shown in Production Examples.

The following abbreviations are used in the Reference Examples and the tables which are shown later. Rex: reference example number, Pre: production example number, Ex: example number, Cmpd: compound number, Str: structural formula, Syn: production method (the figures show example or production example numbers produced in the same manner), Me: methyl, Et: ethyl, Pr: 1-propyl, iPr: 2-propyl, Bu: butyl, tBu: tert-butyl, Boc: tBu-O—CO—, Ac: acetyl, Ms, Me-SO$_2$—, Ph: phenyl, Bn: benzyl, Bz: benzoyl, cPr: cyclopropyl, cBu: cyclobutyl, cPen: cyclopentyl, cHex: cyclohexyl, cHep: cycloheptyl, cOct: cyclooctyl, 2Ad: 2-adamantyl, 2Py: 2-pyridyl, 3Py: 3-pyridyl, 4Py: 4-pyridyl, 3Qui: 3-quinolyl, Dat: physicochemical date (F: FAB-MS (M+H)$^+$; —FN: FAB-MS (M−H)$^-$; ESI: ESI-MS (M+H)$^+$; EI: EI-MS (M+H)$^+$; NMR1: δ (ppm) of characteristic peak of $^1$H NMR in DMSO-d$_6$; NMR2: δ (ppm) of characteristic peak of $^1$H NMR in CDCl$_3$; MP: melting point (° C.); Sal: salt (no description: free; HCl: hydrochloride; the numeral shows the ratio of acid components, for example, 2HCl means dihydrochloride)). In addition, the number before each substituent indicates the substituting position, and the presence of two or more numbers indicates two or more substitutions. For example, 2-MeO-Ph indicates 2-methoxyphenyl, and 2,4-F$_2$-Ph indicates 2,4-difluorophenyl.

REFERENCE EXAMPLE 1

A Boc compound obtained by allowing 4-(2-aminoethyl) aniline to react with tert-butyl dicarbonate in THF was allowed to react with formic acid in dichloromethane in the presence of WSC hydrochloride, thereby obtaining a formylaminophenyl compound. This was further treated with 4 M hydrogen chloride/ethyl acetate solution in ethyl acetate to obtain 4-(2-aminoethyl)phenylformamide hydrochloride. F: 165.

REFERENCE EXAMPLE 2

3-(2-morpholin-4-ylethyl)aniline was obtained by treating 3-(2-morpholin-4-yl-2-oxoethyl)aniline with lithium aluminum hydride in THF. F: 207.

REFERENCE EXAMPLE 3

A compound obtained by allowing 4-nitrobenzyl bromide and 2-(morpholin-4-yl)ethylamine to undergo the reaction in DMF in the presence of potassium carbonate was allowed to react with di-tert-butyl carbonate in 1,4-dioxane, thereby obtaining a Boc compound. This was further subjected to catalytic hydrogenation in methanol in the presence of 10% palladium/carbon to obtain tert-butyl 4-aminobenzyl-(2-morpholin-4-ylethyl) carbamate. F: 336.

REFERENCE EXAMPLE 4

In the presence of triethylamine, a toluene solution of 2-(4-nitrophenyl)propionic acid was allowed to react with DPPA at room temperature and then under heating, and further allowed to react with tert-butanol under heating, thereby obtaining a Boc compound (F: 366). The resulting compound was subjected to catalytic hydrogenation in the same manner as shown in Reference Example 3 to obtain tert-butyl 1-(4-aminophenyl)ethylcarbamate. NMR1: 1.23 (3H, d, J=8.8 Hz), 1.35 (9H, s), 6.48 (2H, d, J=8.4 Hz)

REFERENCE EXAMPLE 5

4-(4-nitrophenyl)butanoic acid and piperidine were allowed to undergo the reaction in DMF using WSC hydrochloride and HOBt, subjected to catalytic hydrogenation in the same manner as shown in Reference Example 3 to reduce the nitro group, and then reduced in the same manner as in Reference Example 2, and the resulting compound was subjected to salt formation using 4 M hydrogen chloride/ethyl acetate solution to obtain 4-(4-piperidin-1-ylbutyl) aniline dihydrochloride. F: 233.

REFERENCE EXAMPLE 6

N-methylation of N-(4-nitrophenyl)morpholine-4-carboxamide was effected by allowing it to react with sodium hydride and methyl iodide in DMF, and the resulting compound was subjected to catalytic hydrogenation in the same manner as shown in Reference Example 3 to obtain N-(4-aminophenyl)-N-methylmorpholine-4-carboxamide. F: 236.

REFERENCE EXAMPLES 7 and 8

4-Fluoronitrobenzene and 2,6-dimethylmorpholine were allowed to undergo the reaction in DMF in the presence of diisopropylethylamine, and then cis and trans isomers were separated and purified by a silica gel column chromatography and respectively subjected to catalytic hydrogenation in the same manner as shown in Reference Example 3 to obtain cis-4-(2,6-dimethylmorpholin-4-yl)aniline (Reference Example 7; F: 207) and trans-4-(2,6-dimethylmorpholin-4-yl)aniline (Reference Example 8; F: 207).

REFERENCE EXAMPLE 9

2-Fluoro-4-nitrotoluene and p-formaldehyde were allowed to undergo the reaction in DMSO in the presence of sodium methoxide, and then the resulting compound was subjected to catalytic hydrogenation in the same manner as shown in Reference Example 3 to obtain 3-fluoro-4-(2-hydroxyethyl)aniline. F: 156.

REFERENCE EXAMPLE 10

3,4,5-Trifluorobenzoic acid was allowed to react with ethanol in the presence of concentrate sulfuric acid and then allowed to react with morpholine in DMF solution, thereby obtaining 3,5-difluoro-(4-morpholin-4-yl)benzoic acid ethyl ester (EI (M$^+$): 271). This was further hydrolyzed in methanol with 1 M sodium hydroxide aqueous solution, and then allowed to react with DPPA in toluene in the presence of triethylamine at room temperature, heated, and further allowed to react with tert-butanol under heating, thereby obtaining a Boc compound (F: 315). By further treating with 4 M hydrogen chloride/ethyl acetate solution, 3,5-difluoro-4-(morpholin-4-yl)aniline hydrochloride was obtained. F: 215.

REFERENCE EXAMPLE 11

2-Chloro-4-{[3-(1-hydroxyethyl)phenyl]amino}pyrimidine-5-carboxylic acid ethyl ester synthesized in accordance with the method described in WO 99/31073 and 2-(3,5-dichloro-4-hydroxyphenyl)ethylamine hydrochloride were allowed to undergo the reaction at 80 to 90° C. in NMP in the presence of diisopropylethylamine, and the resulting compound was allowed to react with 1 M sodium hydroxide aqueous solution under heating in a mixed methanol-THF solution to obtain 2-{[2-(3,5-dichloro-4-hydroxyphenyl)ethyl]amino}-4-{[3-(1-hydroxyethyl)phenyl]amino}pyrimidine-5-carboxylic acid. F: 463

REFERENCE EXAMPLE 12

2,4-Dichloropyrimidine-5-carboxylic acid ethyl ester was allowed to react with sodium thiomethylate at −10° C. in THF in the presence of benzyl triethylammoniumchloride and then allowed to react with tyramine hydrochloride at 70° C. in NMP in the presence of diisopropylethylamine. The resulting compound was hydrolyzed in methanol using 1 M sodium hydroxide aqueous solution and then treated in NMP with aqueous ammonia in the presence of WSC hydrochloride and HOBt to convert into a carboxamide compound which was further allowed to react with m-chloroperbenzoic acid in NMP, thereby obtaining 2-{[2-(4-hydroxyphenyl)ethyl]amino}-4-(methylsulfinyl)pyrimidine-5-carboxamide. F: 321.

REFERENCE EXAMPLE 13

2-Chloro-4-(methylthio)pyrimidine-5-carboxylic acid ethyl ester was allowed to react with 4-(morpholin-4-yl) aniline at 90° C. in NMP in the presence of 4 M hydrogen chloride/dioxane and further treated in the same manner as in and after the hydrolysis of Reference Example 12 to obtain 4-(methylsulfinyl)-2-{[4-(4-oxidomorpholin-4-yl)phenyl]amino}pyrimidine-5-carboxamide. F: 378.

REFERENCE EXAMPLE 14

4-Chloro-2-methylthiopyrimidine-5-carboxylic acid ethyl ester and benzylamine were allowed to undergo the reaction in acetonitrile in the presence of diisopropylethylamine and further treated in the same manner as in and after the hydrolysis of Reference Example 12 to obtain 4-benzylamino-2-(methylsulfonyl)pyrimidine-5-carboxamide. F: 307.

REFERENCE EXAMPLE 15

2-(Benzotrizol-1-yloxy)-4-{[3-(1-hydroxyethyl)phenyl]amino}pyrimidine-5-carboxamide was synthesized in the same manner as the method of Reference Example 6 in WO 99/31073. F: 392.

REFERENCE EXAMPLE 16

2,4-Dichloropyrimidine-5-carboxylic ethyl ester and m-toluidine were allowed to undergo the reaction in acetonitrile in the presence of diisopropylamine to obtain 2-chloro-4-[(3-methylphenyl)amino]pyrimidine-5-carboxylic ethyl ester. Said ester compound was hydrolyzed in THF with 1 M sodium hydroxide aqueous solution, and the resulting carboxylic acid compound was allowed to react with oxalyl chloride in dichloromethane in the presence of a catalytic amount of DMF and then treated with a mixture of aqueous ammonia and ice to obtain 2-chloro-4-[(3-methylphenyl)amino]pyrimidine-5-carboxamide. F: 263.

REFERENCE EXAMPLE 17

2-{[4-(Aminomethyl)phenyl]amino}-N-methyl-4-[(3-methylphenyl)amino]pyrimidine-5-carboxamide was obtained in the same manner as in Production Example 8 which is described later, using 2-chloro-N-methyl-4-[(3-methylphenyl)amino]pyrimidine-5-carboxamide and tert-butyl (4-aminophenyl)methylcarbamate. F: 363.

REFERENCE EXAMPLE 18

2-Benzyloxy-6-fluorobenzylamine was obtained by reducing 2-benzyloxy-6-fluorobenzamide in the same manner as in Reference Example 2. F: 232.

REFERENCE EXAMPLE 19

4-(2-Morpholin-4-yl-ethoxy)aniline dihydrochloride was obtained by carrying out catalytic hydrogenation of 1-[2-(4-nitrophenoxy)ethyl]morpholine in the same manner as in Reference Example 3 and then treating with 4 M hydrogen chloride/ethyl acetate. F: 223.

REFERENCE EXAMPLE 20

1-(4-Nitrophenyl)pyrroidin-3-ol and methanesulfonyl chloride were allowed to undergo the reaction in THF in the presence of triethylamine. The resulting compound and sodium cyanide were allowed to undergo the reaction in 1-methyl-2-pyrrolidone under heating. The resulting compound was subjected to catalytic hydrogenation in the same manner as shown in Reference Example 3 to obtain 1-(4-aminophenyl)pyrrolidine-3-carbonitrile. NMR2: 1.48 (9H, s), 3.12-3.19 (2H, m), 6.46-6.50 (2H, m).

REFERENCE EXAMPLE 21

1-(4-nitrophenyl)piperazine and N,N-dimethylglycine hydrochloride were allowed to undergo the reaction using WSC hydrochloride and HOBt in 1-methyl-2-pyrrolidone in the presence of triethylamine. The resulting compound was subjected to-catalytic hydrogenation in the same manner as shown in Reference Example 3 to obtain 1-[4-(4-aminophenyl)piperazin-1-yl]-2-dimethylaminoethanone. NMR2: 2.30 (6H, s), 3.74-3.76 (4H, m), 6.64-6.68 (2H, m).

REFERENCE EXAMPLE 22

2-[1-(4-Nitrophenyl)piperidin-4-yl]ethanol and methanesulfonyl chloride were allowed to undergo the reaction in THF in the presence of triethylamine. The resulting compound and morpholine were allowed to undergo the reaction under heating in 1-methyl-2-pyrrolidine. The resulting compound was subjected to catalytic hydrogenation in the same manner as shown in Reference Example 3 to obtain 4-[4-(2-morpholin-4-ylethyl)piperidin-1-yl]aniline. NMR2 ($CDCl_3$): 3.21-3.45 (4H, m), 3.71-3.80 (4H, m) 6.63-6.66 (2H, m).

REFERENCE EXAMPLE 23

6-(4-Nitrophenyl)morpholin-3-one was treated in the same manner as the N-methylation shown in Reference Example 6, and the resulting compound was subjected to catalytic hydrogenation in the same manner as shown in Reference Example 3 to obtain 6-(4-aminophenyl)-N-methylmorpholin-3-one. F: 207.

REFERENCE EXAMPLE 24

6-(4-Aminophenyl)-N-methylmorpholin-3-one was treated in the same manner as the reduction shown in Reference Example 2 and further treated with 4 M hydrogen chloride/ethyl acetate solution in ethyl acetate to obtain 4-(4-methylmorpholin-2-yl)phenylamine dihydrochloride. F: 193.

REFERENCE EXAMPLE 25

(R)-5-phenylmorpholin-3-one was allowed to react with nitric acid in concentrated sulfuric acid, and the resulting (R)-5-(4-nitrophenyl)morpholin-3-one (F: 223) was subjected to catalytic hydrogenation in the same manner as shown in Reference Example 3 to obtain (R)-5-(4-aminophenyl)morpholin-3-one. F: 193.

REFERENCE EXAMPLE 26

4-Fluoronitrobenzene and piperidin-4-one hydrochloride were allowed to undergo the reaction in THF in the presence of potassium carbonate. The resulting compound was allowed to react with sodium hydride and ethyl diethylphosphonoacetate in THF. The resulting compound was subjected to catalytic hydrogenation in the same manner as shown in Reference Example 3 to obtain [1-(4-aminophenyl)piperidin-4-yl]acetic acid ethyl ester. NMR2: 1.27 (3H, t, J=7.2 Hz), 2.33 (2H, d, J=7.2 Hz), 6.66-6.89 (2H, m).

REFERENCE EXAMPLE 27

(R)-5-(4-nitrophenyl)morpholin-3-one was treated with borane-THF in THF, and the resulting compound was allowed to react with di-tert-butyl dicarbonate in dichloromethane to obtain a Boc compound (F: 309) which was subsequently subjected to catalytic hydrogenation in the same manner as shown in Reference Example 3 to obtain (R)-3-(4-aminophenyl)morpholine-4-carboxylic acid tert-butyl ester. F: 279.

REFERENCE EXAMPLE 28

2-[1-(4-Nitrophenyl)piperidin-4-yl]ethanol and methane sulfonyl chloride were allowed to undergo the reaction in THF in the presence of triethylamine. The resulting compound and potassium phthalimide were allowed to undergo the reaction under heating in 1-methyl-2-pyrrolidone in the presence of potassium iodide. The resulting compound was allowed to react with hydrazine monohydrate in chloroform-methanol. The resulting compound and di-tert-butyl dicarbonate were allowed to undergo the reaction under heating in THF. The resulting compound was subjected to catalytic hydrogenation in the same manner as shown in Reference Example 3 to obtain tert-butyl {2-[1-(4-aminophenyl)-piperidin-4-yl]ethyl}-carbamate. FN: 318.

REFERENCE EXAMPLE 29

1-(4-Nitrophenyl)piperazine and N-(3-bromopropyl)phthalimide were allowed to undergo the reaction under heating in 1-methyl-2-pyrrolidone in the presence of potassium carbonate. The resulting compound was allowed to react with hydrazine monohydrate in THF. The resulting compound and di-tert-butyl dicarbonate were allowed to undergo the reaction in THF. The resulting compound was subjected to catalytic hydrogenation in the same manner as shown in Reference Example 3 to obtain tert-butyl{3-[4-(4-aminophenyl)-piperazin-1-yl]propyl}carbamate. F: 335.

REFERENCE EXAMPLE 30

1-(4-Nitrophenyl)piperazine and ethyl 4—bromobutanoate were allowed to undergo the reaction under heating in 1-methyl-2-pyrrolidone in the presence of potassium carbonate. The resulting compound was subjected to catalytic hydrogenation in the same manner as shown in Reference Example 3 to obtain ethyl 4-[4-(4-aminophenyl)-piperazin-1-yl]butanoate. F: 264.

REFERENCE EXAMPLE 31

4-Fluoronitrobenzene and morpholine-3-carboxylic acid ethyl ester were allowed to undergo the reaction at 100° C. in DMSO in the presence of diisopropylethylamine, and then the resulting compound was subjected to catalytic hydrogenation in the same manner as shown in Reference Example 3 to obtain 4-(4-aminophenyl)morpholine-3-carboxylic acid ethyl ester. ESI: 251.

REFERENCE EXAMPLE 32

1-(4-Nitrophenyl)piperazine and 4-bromobutyronitrile were allowed to undergo the reaction under heating in 1-methyl-2-pyrrolidone in the presence of potassium carbonate. The resulting compound was allowed to react with polyphosphoric acid under heating and then subjected to catalytic hydrogenation in the same manner as shown in Reference Example 3 to obtain 4-[4-(4-aminophenyl)piperazin-1-yl]butanamide. F: 263.

REFERENCE EXAMPLE 33

4-Fluoronitrobenzene and 1-methylpyrrolidin-3-ol were allowed to undergo the reaction in 1-methylpyrrolidone in the presence of sodium hydride. The resulting compound was subjected to catalytic hydrogenation in the same manner as shown in Reference Example 3 to obtain 4-(1-methylpyrrolidin-3-yl)oxoaniline. F: 193.

REFERENCE EXAMPLE 34

1-(4-Nitrophenyl)piperazine and N-(3-bromopropyl)phthalimide were allowed to undergo the reaction under heating in 1-methyl-2-pyrrolidone in the presence of potassium carbonate. The resulting compound was allowed to react with hydrazine monohydrate in THF. The resulting compound was allowed to react with trimethylsilyl isocyanate in THF and then subjected to catalytic hydrogenation in the same manner as in Reference Example 3 to obtain {3-[4-(4-aminophenyl)piperazin-1-yl]propyl}urea. F: 276.

REFERENCE EXAMPLE 35

3-Fluoronitrobenzene and 2-morpholin-4-yl ethylamine were added, and the resulting compound was subjected to catalytic hydrogenation in the same manner as shown in Reference Example 3 and then treated with 4 M hydrogen chloride/ethyl acetate solution in ethyl acetate to obtain 3-[N-(2-morpholin-4-ylethyl)amino]aniline hydrochloride. F: 222.

REFERENCE EXAMPLE 36

2-Morpholin-4-yl-5-nitrophenol and 4-(2-chloroethyl)morpholine were allowed to undergo the reaction in DMF in the presence of potassium carbonate, and then the resulting compound was subjected to catalytic hydrogenation in the same manner as shown in Reference Example 3 and further treated with 4 M hydrogen chloride/ethyl acetate solution in ethyl acetate to obtain 4-morpholin-4-yl-3-(2-morpholin-4-ylethoxy)aniline hydrochloride F: 308.

REFERENCE EXAMPLE 37

6-Hydroxy-2-methyl-3,4-dihydro-2H-isoquinolin-1-one was allowed to react with trifluoromethanesulfonic anhydride in dichloromethane in the presence of 2,6-lutidine and dimethylaminopyridine, and the resulting compound was introduced with carbon monoxide gas in a mixture of methanol, DMF, triethylamine, palladium acetate and 1,3-bis(diphenylphosphino)propane to obtain a methyl ester compound (F: 220). Subsequently, this was hydrolyzed in methanol with 1 M sodium hydroxide aqueous solution, allowed to react with DPPA at room temperature in toluene in the presence of triethylamine, heated, and then allowed to react with tert-butanol under heating to obtain a Boc compound (F: 277). This was further treated with 4 M hydrogen chloride/ethyl acetate solution to obtain 6-amino-2-methyl-3,4-dihydro-2H-isoquinolin-1-one hydrochloride. EI: 176.

REFERENCE EXAMPLE 38

2-Methyl-2H-isoquinolin-1-one was subjected to catalytic hydrogenation in a hydrogen atmosphere in ethanol in the presence of palladium/carbon. The resulting compound and concentrated nitric acid were allowed to undergo the reaction in concentrated sulfuric acid. The resulting compound was subjected to catalytic hydrogenation in the same manner as shown in Reference Example 3 to obtain 7-amino-2-methyl-3,4-dihydro-2H-isoquinolin-1-one. NMR2: 2.88 (2H, t, J=6.8 Hz), 3.13 (3H, s), 6.95 (1H, d, J=8.0 Hz).

REFERENCE EXAMPLE 39

2-Methoxy-5-methylbenzamide was treated in the same manner as the reduction shown in Reference Example 2 and further treated with 4 M hydrogen chloride/ethyl acetate solution to obtain 2-methoxy-5-methylbenzylamine. F: 152.

REFERENCE EXAMPLE 40

2-Fluoro-5-formylbenzonitrile was treated with sodium borohydride and dimethyl sulfate in THF to obtain 5-hydroxymethyl-2-fluorobenzylamine. F: 156.

REFERENCE EXAMPLE 41

2,6-Dimethoxybenzylamine was treated with 48% hydrobromic acid to obtain 2,6-dihydroxybenzylamine hydrobromide. F: 140.

REFERENCE EXAMPLE 42

By treating 3-fluorobenzonitrile with N-methylethanolamine under heating, 3-(N-2-hydroxyethyl-N-methylamino)benzonitrile was obtained (F: 177). This benzonitrile was treated in the same manner as in Reference Example 2 to obtain 3-(N-2-hydroxyethyl-N-methylamino)benzylamine. F: 181.

REFERENCE EXAMPLE 43

4-Nitrocinnamic acid and 1-methylpiperidine were condensed in the same manner as the amidation shown in Reference Example 5, and then the nitro group was reduced in ethanol using zinc powder and calcium chloride to obtain 4-[(1E)-3-(4-methylpiperazin-1-yl)-3-propen-1-ylaniline. ESI: 246.

REFERENCE EXAMPLE 44

1-Boc-piperazine and 4-nitrobenzoyl chloride were allowed to undergo the reaction in DMF in the presence of triethylamine, and then the nitro group was reduced in the sama manner as the catalytic hydrogenation shown in Reference Example 3 to obtain tert-butyl 4-(4-aminobenzoyl)piperazine-1-carboxylate. ESI: 307.

REFERENCE EXAMPLE 45

1-Boc-piperazine and 4-nitrobenzenesulfonyl chloride were allowed to undergo the reaction in DMF in the presence of triethylamine, and then the nitro group was reduced in the sama manner as the catalytic hydrogenation shown in Reference Example 3 to obtain tert-butyl 4-[(4-aminophenyl)sulfonyl]piperazine-1-carboxylate. FN: 340.

REFERENCE EXAMPLE 46

4-Iodonitrobenzene and tert-butyl 5-oxo-[1,4]diazepan-1-carboxylate were allowed to undergo the reaction in 1,2-dichlorobenzene in the presence of copper powder and potassium carbonate, and then the nitro group was reduced in ethanol using zinc powder and calcium chloride to obtain benzyl 4-(4-aminophenyl)-5-oxo-1,4-diazepan-1-carboxylate. ESI: 340.

REFERENCE EXAMPLE 47

After allowing tert-butyl 4-[(4-nitrophenyl)acetyl]piperazine-1-carboxylate and methyl bromoacetate to undergo the reaction in DMF in the presence of sodium hydride, the nitro group was reduced in the same manner as the catalytic hydrogenation shown in Reference Example 3, and then this was treated with lithium aluminum hydride and subjected to salt formation in the same manner as in Reference Example 1 to obtain 3-(4-aminophenyl)-4-(4-methylpiperazin-1-yl)butan-1-ol trihydrochloride. ESI: 264.

REFERENCE EXAMPLE 48

1-[(4-Nitrophenyl)acetyl]piperidine was alkylated with methyl -bromoacetate in the same manner as in Reference Example 47, hydrolyzed with 1 M sodium hydroxide aqueous solution in methanol, and then condensed with 1-methylpiperazine in the same manner as in Reference Example 5 to obtain 1-methyl-4-[3-(4-nitrophenyl)-4-oxo-4-piperidin-1-ylbutanoyl]piperazine (ESI: 389). This piperazine compound was subjected to the reduction of nitro group in the same manner as the catalytic hydrogenation shown in Reference Example 3 and then treated with lithium aluminum hydride to obtain 4-[3-(4-methylpiperazin-1-yl)-1-(piperidin-1-ylmethyl)propyl]aniline. ESI: 331.

In addition, the compounds of Reference Examples 49 to 51 were obtained in the same manner as in Reference Example 2, and the compounds of Reference Examples 52 and 53 in the same manner as in Reference Example 3, the compounds of Reference Examples 54 and 55 in the same manner as the catalytic hydrogenation shown in Reference Example 3, the compounds of Reference Examples 56 to 77 in the same manner as in Reference Example 7, the compound of Reference Example 78 in the same manner as in Reference Example 9, the compounds of Reference Examples 79 to 86 in the same manner as in Reference Example 11, the compound of Reference Example 87 in the same manner as in Reference Example 12, the compound of Reference Example 88 in the same manner as in Reference Example 13, the compound of Reference Example 89 in the same manner as in Reference Example 14, the compounds of Reference Examples 90 to 103 in the same manner as in Reference Example 16, the compounds of Reference Examples 104 and 105 in the same manner as in Reference Example 19, the compounds of Reference Examples 106 and 107 in the same manner as in Reference Example 23, the compound of Reference Example 108 in the same manner as in Reference Example 25, the compound of Reference Example 109 in the same manner as in Reference Example 27, the compound of Reference Example 110 in the same manner as in Reference Example 32, the compound of Reference Example 111 in the same manner as in Reference Example 33, the compound of Reference Example 112 in the same manner as in Reference Example 35, the compounds of Reference Examples 113 and 114 in the same manner as in Reference Example 39, the compounds of Reference Examples 115 to 118 in the same manner as in Reference Example 40, and the compound of Reference Example 119 in the same manner as in Reference Example 42. Structures and physicochemical data of the compounds of Reference Examples 49 to 119 are shown in Tables 1 to 5.

EXAMPLE 1

To 8 ml NMP solution of 750 mg of 4-benzylamino-2-methylsulfonylpyrimidine-5-carboxamide were added 765 mg of 2-(3-chloro-4-hydroxyphenyl)ethylamine hydrochloride and 1.07 ml of diisopropylethylamine, followed by stirring at 110° C. for 1 hour. The reaction mixture was cooled down to room temperature, and then mixed with water and extracted with ethyl acetate. The organic layer was washed with saturated brine, and then the solvent was evaporated. The resulting residue was purified by a silica gel column chromatography (chloroform:methanol:aqueous ammonia) and the resulting crude crystals were recrystallized (methanol-ethyl acetate) to obtain, 280 mg of 4-benzylamino-2-{[2-(3-chloro-4-hydroxyphenyl)ethyl]amino}pyrimidine-5-carboxamide as colorless crystals.

EXAMPLE 2

A 30 ml dichloromethane solution of 4.0 g of 2-chloro-4-[(3-methylphenyl)amino]pyrimidine-5-carbonyl chloride was added at −50° C. to a mixture of 1.32 g of 40% methylamine aqueous solution, 2.53 ml of diisopropylethylamine and 10 ml of THF, followed by stirring for 30 minutes. This reaction mixture was poured into a mixture of 30 ml 1 M hydrochloric acid and ice and extracted with chloroform. After washing the organic layer with saturated brine and subsequently evaporating the solvent, an 800 mg portion of 3.30 g the resulting 5-carboxamide compound was made into 8 ml of NMP solution, mixed with 1.05 g of 4-(2-aminoethyl)-2,6-dichlorophenol and 1.26 ml of diisopropylethylamine, followed by stirring overnight at 80° C. The reaction mixture was cooled down to room temperature, and then mixed with water and extracted with ethyl acetate. The organic layer was washed with saturated brine, and then the solvent was evaporated. The resulting residue was purified by a silica gel column chromatography (chloroform:methanol) and then recrystallized (methanol-THF) to obtain 265 mg of 2-{[2-(3,5-dichloro-4-hydroxyphenyl)ethyl]amino}-N-methyl-4-[(3-methylphenyl)amino]pyrimidine-5-carboxamide as colorless crystals.

EXAMPLE 3

A 5 ml NMP solution of 352 mg of 4-morpholinoaniline was mixed with 0.95 ml of 4 M hydrogen chloride/1,4-dioxane solution and 400 mg of 4-benzylamino-2-chloropyrimidine-5-carboxamide, followed by stirring at 90° C. for 3 hours. The reaction mixture was cooled down to room temperature, and then the precipitate was collected by filtration. The collected solid was mixed with saturated sodium bicarbonate aqueous solution and extracted with a mixed solution of THF-ethyl acetate. The organic layer was washed with saturated brine, and then the solvent was evaporated. The resulting residue was crystallized by adding methanol and then recrystallized (methanol-THF) to obtain 264 mg of 4-benzylamino-2-{[4-(morpholin-4-yl)phenyl]amino}pyrimidine -5-carboxamide as colorless crystals.

EXAMPLE 4

At −7° C., 429 mg of mCPBA was gradually added to a 5 ml DMA solution of 397 mg of 4-benzylamino-2-{[4-(piperidin-1-ylmethyl)phenyl]amino}pyrimidine-5-carboxamide, followed by stirring for 30 minutes. After concentration of the reaction mixture, the resulting residue was purified by a silica gel column chromatography (chloroform:methanol:aqueous ammonia) and then recrystallized (methanol-ethyl acetate) to obtain 228 mg of 4-benzylamino-2-({4-[(1-oxidopiperidyl-1-yl)methyl]phenyl}amino)pyrimidine-5-carboxamide as colorless crystals.

EXAMPLE 5

A 10 ml 1,4-dioxane solution of 738 mg of tert-butyl 4-(4-{[5-(aminocarbonyl)-4- (benzylamino)pyrimidin-2-yl]amino }phenyl)piperazin- 1 -carboxylate was mixed with 2.77 ml of 4 M hydrogen chloride/1,4-dioxane solution and 3 ml of water, followed by stirring at 90° C. for 2 hours. The reaction mixture was cooled down to room temperature, diluted with water, mixed with saturated sodium bicarbonate aqueous solution and then extracted with an ethyl acetate-THF mixed solution. After washing of the organic layer with saturated brine and subsequent evaporation of the solvent, the resulting solid was recrystallized (THF-ethanol) to obtain 413 mg of 4-benzylamino-2- {[4-(piperazin- 1 -yl)phenyl]amino}pyrimidine-5- carboxamide as ivory-colored crystals.

EXAMPLE 6

A 7 ml DMF solution of 564 mg of 4-benzylamino-2-{[4-(piperidin-4-yloxo)phenyl]amino}pyrimidine-5-carboxamide was mixed with 175 mg of 35% aqueous formalin and 452 mg of sodium triacetoxy borohydride, followed by stirring at room temperature for 2 hours. The reaction mixture was mixed with water and concentrated, and the resulting residue was purified by a silica gel column chromatography (chloroform:methanol:aqueous ammonia) and then recrystallized (THF-methanol) to obtain 273 mg of 4-benzylamino-2-{[4-(1-methylpiperidin-4-yloxo)phenyl]amino)pyrimidine-5-carboxamide as colorless crystals.

EXAMPLE 7

A 20 ml portion of THF-methanol (2:1) mixed solution of 290 mg of 4-[(2-benzyloxy-6-fluorobenzyl)amino]-2-[(4-morpholin-4-ylphenyl)amino]pyrimidine-5-carboxamide synthesized in the same manner as in Production Example 13 was mixed with 50 mg of 10% palladium-carbon, followed by stirring for 1 hour in a hydrogen atmosphere. The reaction mixture was filtered and then mixed with 100 mg of 10% palladium-carbon, followed by stirring for 6 hours in a hydrogen atmosphere. After filtration of the reaction mixture and subsequent evaporation of the solvent, the resulting residue was purified by a silica gel column chromatography (chloroform-methanol). By recrystallizing the resulting crude crystals (THF-methanol), 117 mg of 4-[(2-hydroxy-6-fluorobenzyl)amino]-2-[(4-morpholin-4-ylphenyl)amino]pyrimidine-5-carboxamide was obtained as colorless crystals.

EXAMPLE 8

A 5 ml pyridine solution of 304 mg of 4-(2-aminobenzyl)amino-2-{[4-morpholin-4-yl]phenyl}amino}pyrimidine-5-carboxamide was mixed with 0.1 ml of acetic anhydride under ice-cooling and then followed by stirring at room temperature for 30 minutes. The reaction mixture was diluted with water, and then the precipitate was collected by filtration. By washing the collected solid (methanol-THF), 285 mg of 4-(2-acetylaminobenzyl)amino-2-{[4-morpholin-4-yl] phenyl}amino}pyrimidine-5-carboxamide was obtained as a colorless solid.

EXAMPLE 9

A 15 ml THF-methanol (1:1) solution of 750 mg of ethyl 1-(4-{[5-(aminocarbonyl)-4-(benzylamino)pyrimidin-2-yl] amino}phenyl)piperidine-4-carboxylate was mixed with 1 M sodium hydroxide aqueous solution, followed by stirring under heating at 60° C. for 1 hour. The reaction mixture was cooled down to room temperature and mixed with 1 M sodium hydroxide aqueous solution, and the precipitated solid was collected by filtration and washed with water and methanol. By recrystallizing the resulting solid from a THF-methanol mixed solvent, 361 mg of 1-(4-{[5-(aminocarbonyl)-4-(benzylamino)pyrimidin-2-yl]amino}phenyl)piperidine-4-carboxylic acid was obtained as a colorless solid.

EXAMPLE 10

Under ice-cooling, 0.05 ml of methanesulfonyl chloride was added to a mixture of 300 mg of 4-benzylamino -2-{[4-(2-aminomethylmorpholin-4-yl)phenyl]aminolpyrimidine -5-carboxamide, 0.25 ml of triethylamine and 5 ml of DMF, followed by stirring at room temperature. After concentration of the reaction mixture, the resulting residue was purified by a silica gel column chromatography (chloroform-methanol). The resulting crude crystals were dissolved in a methanol-THF mixed solution and mixed with 0.5 ml of 4 M hydrogen chloride/ethyl acetate solution, and the thus precipitated crystals were collected by filtration and further recrystallized (ethanol-water) to-obtain-285 mg of 4-benzylamino-2-{[4-(2-([(methylsulfonyl)amino]methyl}morpholin-4-yl)phenyl]amino}pyrimidine-5-carboxamide hydrochloride as a colorless solid.

EXAMPLE 11

A 5 ml portion of 1-methyl-2-pyrrolidone solution of 400 mg of 4-benzylamino-2-[(4-piperazin-1-ylphenyl)amino]pyrimidine-5-carboxamide was mixed with 0.12 ml of ethyl bromoacetate and 200 mg of potassium carbonate, followed by stirring at room temperature for 30 minutes. The reaction mixture was mixed with water, and the organic layer was extracted with ethyl acetate-THF mixed solvent. The organic layer was washed with water and saturated brine and dried over anhydrous magnesium sulfate, and then the residue obtained by evaporating the solvent was washed with methanol to obtain ethyl[4-(4-{[5-(aminocarbonyl)-4-(benzylamino)pyrimidin-2-yl]amino}phenyl)piperazin-1-yl]acetate as a pale brown solid.

EXAMPLE 12

A 5 ml THF-5 ml methanol solution of 680 mg of 4-benzylamino-2-{[4-(2-N-methyl-N-trifluoroacetylaminomethylmorpholin -4-yl)phenyl]amino}pyrimidine-5-carboxamide was mixed with 518 mg of potassium carbonate and 4 ml of water, followed by stirring at room temperature. The reaction mixture was mixed with ethyl acetate, washed with water and then concentrated. The resulting residue was purified by a silica gel column chromatography (chloroform-methanol-aqueous ammonia) to obtain 500 mg of crude crystals. A 120 mg portion of the crude crystals were dissolved in a methanol-THF mixed solution and mixed with 0.3 ml of 4 M hydrogen chloride/ethyl acetate solution, and the thus precipitated crystals were collected by filtration and then recrystallized (ethanol-water) to obtain 110 mg of 4-benzylamino-2-[(4-{2-[(methylamino)methyl]morpholin-4-yl}phenyl)amino]pyrimidine-5-carboxamide dihydrochloride as a pale green solid.

EXAMPLE 13

A 780 mg portion of tert-butyl(2-{1-[4-(4-benzylamino-5-carbonylpyrimidin-2-ylamino)phenyl]piperidin -4-yl}ethyl)carbamate was mixed with 10 ml of trifluoroacetic acid, followed by stirring at room temperature for 1 hour. The solvent was evaporated, the resulting residue was mixed with 1 M sodium hydroxide, and the thus formed solid was collected by filtration. The solid was dissolved in chloroform-methanol, washed with saturated brine and then dried with anhydrous magnesium sulfate. The solvent was evaporated, and the resulting residue was dissolved in chloroform-methanol and mixed with 4 M hydrogen chloride/dioxane solution. The solvent was evaporated, and the resulting residue was recrystallized from THF-methanol-water to obtain 215 mg of 2-({4-[4-(2-aminoethyl)piperidin-1-yl]phenyl)amino)-4-(benzylamino)pyrimidine-5-carboxamide trihydrochloride as a colorless solid.

EXAMPLE 14

A 5 ml methanol solution containing 80 mg of 4-(benzylamino)-2-{[4-(β-D-acetylglucopyranosyloxy)phenyl] amino}pyrimidine-5-carboxamide was mixed with sodium methoxide, followed by stirring overnight at room temperature. The reaction mixture was filtered by adding an ion exchange resin (Dowex 50WX8-100) and then concentrated, and the resulting crystals were washed with methanol to obtain 22 mg of 4-(benzylamino)-2-{[4-(β-D-glucopyranosyloxy)phenyl]amino}pyrimidine-5-carboxamide as pale brown crystals.

EXAMPLE 15

A 10 ml portion of 1-methyl-2-pyrrolidone solution containing 800 mg of 2-({4-(piperidin-4-yloxy)phenyl]amino}-4-4[(2,3,6-trifluorobenzyl)amino]pyrimidine-5-carboxamide was mixed with 0.12 ml of methyl iodide and 300 mg of potassium carbonate, followed by stirring at room temperature for 1 hour and then at 60° C. for 30 minutes. A 0.1 ml portion of methyl iodide was further added thereto, followed by stirring for 30 minutes. The reaction mixture was cooled down to room temperature, mixed with water and then extracted with an ethyl acetate-THF mixed solvent. The organic layer was washed with water and saturated brine and then dried over anhydrous magnesium sulfate. The solvent was evaporated, and the resulting residue was purified by a silica gel column chromatography (chloroform-methanol-aqueous ammonia) and further recrystallized from ethanol to obtain 197 mg of 2-({4-[(1-methylpiperidin-4-yl)oxy]phenyl}amino)-4-[(2,3,6-trifluorobenzyl)amino]pyrimidine-5-carboxamide as colorless crystals.

PRODUCTION EXAMPLE 1

A 6 ml portion of NMP solution containing 600 mg of 2-(benzotriazol-1-yloxy)-4-[(3-methylphenyl)amino]pyrimidine-5-carboxamide was mixed with 538 mg of 2-(3-bromo-4-hydroxyphenyl)ethylamine and 0.72 ml of diisopropylethylamine, followed by stirring at 80° C. for 2 hours. The reaction mixture was cooled down to room temperature, and then mixed with water and extracted with ethyl aceatate. The organic layer was washed with saturated brine, the solvent was evaporated, and then the resulting residue was recrystallized (ethanol-THF) to obtain 200 mg of 2-{[2-(3-bromo-4-hydroxyphenyl)ethyl]amino}-4-[(3-methylphenyl)amino]pyrimidine-5-carboxamide as colorless crystals.

PRODUCTION EXAMPLE 2

A 6 ml portion of NMP solution containing 533 mg of 2-chloro-4-[(3-ethylphenyl)amino]pyrimidine-5-carboxamide was mixed with 0.624 mg of 2-(3-chloro-4-hydroxyphenyl)ethylamine hydrochloride and 0.87 ml of diisopropylethylamine, followed by stirring at 80° C. for 4 hours. The reaction mixture was cooled down to room temperature, and then mixed with water and extracted with ethyl acetate. The organic layer was washed with saturated brine, the solvent was evaporated, and then the resulting residue was recrystallized (methanol-THF) to obtain 460 mg of 2-{[2-(3-chloro-4-hydroxyphenyl)ethyl]amino}-4-[(3-ethylphenyl)amino] pyrimidine-5-carboxamide as colorless crystals.

PRODUCTION EXAMPLE 3

A 8 ml portion of NMP solution containing 800 mg of 2-{[2-(4-hydroxyphenyl)ethyl]amino}-4-(methylsulfinyl) pyrimidine-5-carboxamide was mixed with 373 mg of cyclohexylamine and 0.87 ml of diisopropylethylamine, followed by stirring at 100° C. for 1 hour. The reaction mixture was cooled down to room temperature, and then mixed with water and extracted with ethyl acetate. The organic layer was washed with saturated brine, and then the solvent was evaporated. The resulting residue was purified by a silica gel column chromatography (chloroform:methanol), and the resulting crude crystals were recrystallized (methanol-ethyl acetate) to obtain 547 mg of 2-{[2-(4-hydroxyphenyl)ethyl] amino}-4-cyclohexylaminopyrimidine-5-carboxamide as colorless crystals.

PRODUCTION EXAMPLE 4

A 4 ml portion of DMF solution containing 352 mg of 2-{[2-(4-hydroxyphenyl)ethyl]amino}-4-[(3-methylphenyl)amino]pyrimidine-5-carboxylic acid was mixed with 223 mg of WSC hydrochloride, 157 mg of HOBt and 103 mg of 2-dimethylaminoethylamine, followed by stirring overnight at room temperature. The reaction mixture was diluted with water and then extracted with ethyl acetate. The organic layer was washed with saturated brine and then the solvent was evaporated. The resulting residue was purified by a silica gel column chromatography (chloroform:methanol:aqueous ammonia) and then recrystallized (hexane-ethyl acetate) to obtain 291 mg of N-(2-dimethylaminoethyl)-2-{[2-(4-hydroxyphenyl)ethyl]amino}-4-[(3-methylphenyl)amino]pyrimidine-5-carboxamide as colorless crystals.

PRODUCTION EXAMPLE 5

A 10 ml portion of NMP solution containing 500 mg of 2-{[4-(aminomethyl)phenyl]amino}-4-[(3-methylphenyl)amino]pyrimidine-5-carboxamide dihydrochloride synthesized by the method described in Example 8 of WO 99/31073 was mixed with 0.53 ml of triethylamine and 0.12 ml of acetic anhydride, followed by stirring overnight at room temperature. The reaction mixture was mixed with water and extracted with ethyl acetate, the organic layer was washed with saturated brine and then the solvent was evaporated. The resulting residue was triturated with methanol, and washed to obtain 270 mg of 2-({4-[(acetylamino)methyl]phenyl}amino)-4-[(3-methylphenyl)amino]pyrimidine-5-carboxamide as a pale yellow solid.

PRODUCTION EXAMPLE 6

A 20 ml acetic acid-10 ml THF mixed solution containing 500 mg of 2-{[4-(aminomethyl)phenyl]amino}-4-[(3-methylphenyl)-amino]pyrimidine-5-carboxamide dihydrochloride was mixed with 5.76 g of potassium cyanate, which was added by dividing into 6 portions, at room temperature, followed by stirring for 6 hours. The reaction mixture was concentrated and then poured into water, and the precipitated solid was collected by filtration and washed with acetonitrile. The resulting solid was purified by a silica gel column chromatography (chloroform:methanol) to obtain 150 mg of 4-[(3-methylphenyl)amino]-2-[(4-ureidomethylphenyl)amino]pyrimidine-5-carboxamide as a pale yellow solid.

PRODUCTION EXAMPLE 7

A 10 ml portion of NMP solution containing 1.0 g of 2-{[4-(aminomethyl)phenyl]amino}-4-[(3-methylphenyl)amino]pyrimidine-5-carboxamide dihydrochloride was mixed with 0.83 ml of triethylamine and, under ice-cooling, with 0.4 ml of trifluoroacetic anhydride, followed by stirring at room temperature for 2 hours. The reaction mixture was diluted with water and extracted with ethyl acetate. After washing the organic layer with saturated brine, the solvent was evaporated, and the residue was crystallized from chloroform-hexane to obtain 660 mg of a trifluoroacetylamino compound. A 7 ml portion of DMF solution containing 640 mg of the trifluoroacetylamino compound was mixed with 400 mg of potassium carbonate and 0.11 ml of iodomethane, followed by stirring overnight at room temperature. The reaction mixture was diluted with water and extracted with ethyl acetate, the organic layer was washed with saturated brine, and then the solvent was evaporated. The resulting residue was purified by a silica gel column chromatography (chloroform:methanol) to obtain 280 mg of an N-methyl compound. A 5 ml methanol-5 ml THF mixed solution containing 160 mg of the N-methyl compound was mixed with 2 ml of concentrated aqueous ammonia, followed by stirring overnight at room temperature. The reaction mixture was diluted with water and extracted with ethyl acetate, the organic layer was washed with saturated brine, and then the solvent was evaporated. The resulting solid was recrystallized (methanol-water) to obtain 100 mg of 2-({4-[(methylamino)methyl]phenyl}amino)-4-[(3-methylphenyl)amino]pyrimidine-5-carboxamide as colorless crystals.

PRODUCTION EXAMPLE 8

A mixture of 1.0 g of 2-chloro-4-(3-methylanilino)pyrimidine-5-carboxamide, 1.6 g of tert-butyl 4-aminobenzyl(2-morpholin-4-ylethyl)carbamate, 1.33 ml of diisopropylethylamine and 10 ml of NMP was stirred overnight at 130° C. The reaction mixture was cooled down to room temperature, and then mixed with water and extracted with ethyl acetate. The organic layer was washed with saturated brine, the solvent was evaporated, and the resulting residue was purified by a silica gel column chromatography (chloroform:methanol). Then, a 750 mg portion of 780 mg of the resulting compound was stirred overnight at room temperature in a mixed solution of 75 ml methanol and 30 ml 6 M hydrochloric acid. The reaction mixture was concentrated, and then the resulting crystals were washed with methanol to obtain 510 mg of 4-[(3-methylphenyl)amino]-2-[(4-{[(2-morpholin-4-ylethyl)amino]methyl}phenyl)amino]pyrimidine-5-carboxamide trihydrochloride as colorless crystals.

PRODUCTION EXAMPLE 9

A 7 ml portion of DMF solution containing 685 mg of 2-{[4-(aminomethyl)phenyl]amino}-4-[(3-methylphenyl)amino]pyrimidine-5-carboxamide dihydrochloride was mixed with 0.45 ml of triethylamine, 420 mg of 35% aqueous formalin and 1.09 g of sodium triacetoxy borohydride, followed by stirring overnight at room temperature. The reaction mixture was mixed with water, concentrated and then purified by a silica gel column chromatography (chloroform:methanol:aqueous ammonia) to obtain crude crystals. This was dissolved in a methanol-ethyl acetate mixed solution and mixed with 1 ml of 4 M hydrogen chloride/ethyl acetate solution, and the thus precipitated crystals were collected by filtration and further recrystallized (methanol-water) to obtain 164 mg of 2-({4-[(dimethylamino)methyl]phenyl}amino)-4-[(3-methylphenyl)amino]pyrimidine-5-carboxamide dihydrochloride as colorless crystals.

PRODUCTION EXAMPLE 10

A mixture of 2.0 g of 2-chloro-4-{(3-methylphenyl)amino}pyrimidine-5-carboxamide, 1.25 g of 4-aminophenetyl alcohol, 1.99 ml of diisopropylethylamine and 10 ml of NMP was stirred overnight at 110° C. The reaction mixture was cooled down to room temperature and mixed with water and ethyl acetate, and the thus precipitated solid was collected by filtration and recrystallized (methanol) to obtain 560 mg of 2-{[4-(2-hydroxyethyl)phenyl]amino}-4-[(3-methylphenyl)amino]pyrimidine-5-carboxamide as pale yellow crystals.

PRODUCTION EXAMPLE 11

A 5 ml portion of NMP solution containing 300 mg of 4-benzylamino-2-(methylsulfonyl)pyrimidine-5-carboxamide was mixed with 122 mg of p-anisidine and 58 mg of potassium fluoride, followed by stirring at 90 to 100° C. for 21 hours. During this period, 58 mg of potassium fluoride was added three times. The reaction mixture was cooled down to room temperature, diluted with water, mixed with saturated sodium bicarbonate aqueous solution and then extracted with ethyl acetate. The organic layer was washed with saturated brine, and then the solvent was evaporated. The resulting residue was purified by a silica gel column chromatography (chloroform:methanol) and then recrystallized (methanol-THF) to obtain 82 mg of 4-benzylamino-2-[(4-methoxyphenyl)amino]pyrimidine-5-carboxamide as colorless crystals.

PRODUCTION EXAMPLE 12

A 6 ml portion of NMP solution containing 303 mg of 4-cyclohexylamino-2-(methylsulfonyl)pyrimidine-5-carboxamide was mixed with 1.05 ml of 1 M n-tetrabutylammonium fluoride/THF solution, followed by stirring at 90° C. for 1 hour. Next, this was mixed with 200 mg of 4-morpholinoaniline and 2.77 ml of 4 M hydrogen chloride/1,4-dioxane solution, followed by stirring at 90° C. for 3 hours. The reaction mixture was cooled down to room temperature, diluted with water, mixed with saturated sodium bicarbonate aqueous solution and then extracted with ethyl acetate-THF mixed solution. The organic layer was washed with saturated brine, and then the solvent was evaporated and the resulting residue was purified by a silica gel column chromatography (chloroform:methanol) to obtain 54 mg of 4-cyclohexylamino-2-[(4-morpholinophenyl)amino]pyrimidine-5-carboxamide as a pale brown solid.

PRODUCTION EXAMPLE 13

A mixture of 450 mg of 4-methylsulfinyl-2-({4-[(N-oxidomorpholin-4-yl)methyl]phenyl}amino)pyrimidine-5-carboxamide, 0.29 ml of isopropylamine, 0.24 ml of diisopropylethylamine and 5 ml of DMA was stirred at 80° C. for 3 hours. The reaction mixture was cooled down to room temperature, mixed with 8 ml of 5% sodium hydrogen sulfite, followed by stirring for 1 hour. The reaction mixture was once adjusted to pH 9 by adding 0.5 ml of concentrated aqueous ammonia, diluted with water and then extracted with chloroform. The organic layer was washed with saturated brine, and then the solvent was evaporated. The resulting residue was purified by a silica gel column chromatography (chloroform: methanol:aqueous ammonia), and the resulting pale brown oil was crystallized from ethyl acetate to obtain 50 mg of 2-{[4-(morpholinomethyl)phenyl]amino}-4-(2-propylamino)pyrimidine-5-carboxamide as colorless crystals.

PRODUCTION EXAMPLE 14

A 1 ml portion of chloroform solution containing 11.7 mg of 4-methylsulfinyl-2-({4-[(N-oxidomorpholin-4-yl)methyl]phenyl}amino)pyrimidine-5-carboxamide was mixed with 5.1 mg of cyclopropylamine and 5.8 mg of diisopropylethylamine, followed by stirring at 90° C. for 15 hours. A 1 ml portion of aqueous solution containing 50 mg of sodium hydrogen sulfite was added to the reaction mixture, followed by stirring at room temperature for 4 hours. This was mixed with 0.1 ml of aqueous ammonia and extracted with 2 ml of chloroform. By evaporating the solvent under a reduced pressure and fractionating the residue by an HPLC (Wakosil-II 5C18AR, 0.1% HCOOH—H$_2$O/MeOH=7/3–0/10), 2.6 mg of 4-cyclopropylamino-2-(4-morpholin-4-ylmethylphenylamino)-pyrimidine-5-carboxamide was obtained.

PRODUCTION EXAMPLE 15

A 1 ml portion of THF solution containing 7.9 mg of 4-benzylamino-2-chloropyrimidine-5-carboxamide and 3.7 mg of aniline, followed by stirring at 90° C. for 20 hours, which was then mixed with 60 mg of PS-tosyl chloride (mfd. by Argonaut Technologies, 2.44 mmol/g), followed by stirring at room temperature for 3 hours. The reaction mixture was mixed with 2 ml of saturated sodium bicarbonate aqueous solution and extracted with 2 ml of chloroform. By evaporating the solvent under a reduced pressure, 6.6 mg of 4-benzylamino-2-phenylaminopyrimidine-5-carboxamide was obtained.

PRODUCTION EXAMPLES 16 TO 57

A 960 mg portion of 2-{[2-(4-hydroxyphenyl)ethyl]amino}-4-(methylsulfinyl)pyrimidine-5-carboxamide was dissolved in 100 ml of n-butanol and dispensed in 1.0 ml portions into 96 test tubes. DMF 1.0 M solutions of corresponding amine compounds were added in 50 μl portions, followed by stirring at 100° C. for 10 hours. The solvent was evaporated under a reduced pressure, and each of the resulting crude products was dissolved in 500 μl of methanol and purified by HPLC fractionation using the molecular weight as the trigger by simultaneous measurement of MS, thereby obtaining the compounds of Production Examples 16 to 57.

PRODUCTION EXAMPLES 58 TO 73

Each of 2-chloro-4-(substituted amino)pyrimidine-5-carboxylic acids having various substituting amino groups on the 4-position of pyrimidine was mixed with Rink Amide AM resin, which is prepared as an amine form by removal of Fmoc protecting group by piperazine treatment, and with a mixed solvent of dichloromethane and DMF, further mixed with diisopropyl carbodiimide, followed by stirring at room temperature for 5 hours. The resin was collected by filtration and washed with dichloromethane, DMF, THF and methanol in that order. The same series of washing was repeated once again, and finally washed with diethyl ether. By drying the resin under a reduced pressure, various types of 2-chloro-4-(substituted amino)pyrimidine-5-carboxamide (resin) adhered to the resin via the nitrogen atom of amido moiety were obtained. The resulting resins were respectively added in 100 mg (equivalent to 40 μM) portions to two wells of the reaction vessel of a synthesizer (SY-2000, Shimadzu Corp.). A 1.0 ml portion of 0.5 M NMP solution of tyramine hydrochloride or 2-(3-chloro-4-hydroxyphenyl)ethylamine hydrochloride and 200 μl of 2.5 M NMP solution of diisopropylethylamine were added to each well and shaken at 100° C. for 12 hours. After discarding the reaction mixture by filtration, each resin was washed with DMF (twice), dichloromethane, DMF, THF, methanol and THF in that order. The resin was mixed with 4 ml of dichloromethane solution of 40% trifluoroacetic acid and shaken at room temperature for 5 minutes. Each resin was removed by filtration to collect the reaction mixture. By evaporating the solvent under a reduced pressure, each of the compounds of Production Examples 58 to 73 was obtained. Samples of compounds having a purity of 50% or less were purified by HPLC fractionation using the molecular weight as the trigger by simultaneous measurement of MS.

PRODUCTION EXAMPLES 74 TO 93

A 1.09 g portion of 2-[2-(4-hydroxyphenyl)ethylamino]-4-[(3-methylphenyl)amino]pyrimidine-5-carboxylic acid was dissolved in 200 ml of DMF and dispensed in 2.0 ml portions into 96 test tubes. A 35 μl portion of 1.0 M HOBt/DMF solution and 70 mg of a PS-carbodiimide resin (mfd. by Argonaut Technologies) (1.0-1.5 mmol/g) were added to each test tube. Subsequently, 1.0 M DMF solutions of amine compounds corresponding to the target compounds were added in 25 μl portions and shaken overnight at room temperature. By adding 70 mg of PS-tris amine resin (3-5 mmol/g) and stirring at room temperature for 3 hours, unreacted 2-{2-[(4-hydroxyphenyl)ethyl]amino}-4-[(3-methylphenyl)amino]pyrimidine-5-carboxylic acid and HOBt were bonded to the PS-tris amine resin. By removing the resin by filtration and evaporating the solvent under a reduced pressure, the compounds of Production Examples 74 to 93 were obtained.

The compounds of Examples 16 to 258 and Production Examples 94 to 275 shown in the following Tables 6 to 20 were respectively obtained in the same manner as the methods of the aforementioned Examples or Production Examples. Structures and physicochemical data of the compounds of Examples 1 to 258 and Production Examples 1 to 275 are shown in the following Tables 6 to 20.

In addition, structures of other compounds of the present invention are shown in Tables 21 to 25. These may be easily synthesized by using the methods described in the aforementioned production methods and examples and the methods obvious to those skilled in the art, or modified methods thereof.

TABLE 1

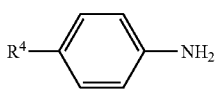

| Rex | R⁴ | Dat |
|---|---|---|
| 52 | 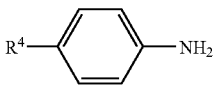 | F: 267 |
| 53 | 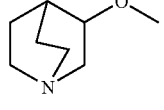 | F: 219 |
| 54 | 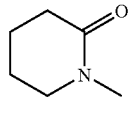 | F: 191 |
| 55 | 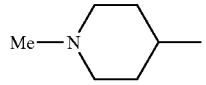 | F: 191 |
| 56 | 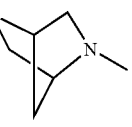 | F: 290 |
| 57 | 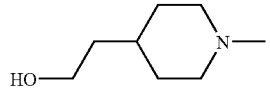 | NMR2: 2.55-2.61(2H, m), 3.72-3.75(2H, m) 6.62-6.66(2H, m) |

TABLE 1-continued

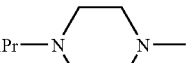

| Rex | R⁴ | Dat |
|---|---|---|
| 58 | 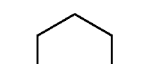 | F: 220 |
| 59 | 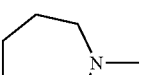 | F: 213  Sal: HCl |
| 60 | 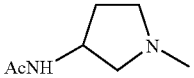 | F: 193  Sal: 2HCl |
| 61 | 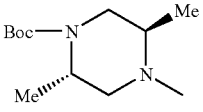 | F: 220 |
| 62 | 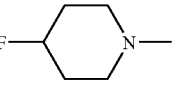 | F: 306 |
| 63 | 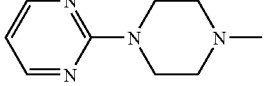 | F: 195  Sal: HCl |
| 64 | 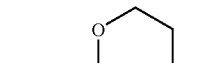 | F: 256  Sal: HCl |
| 65 | 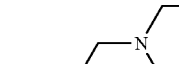 | ESI: 299 |
| 66 | 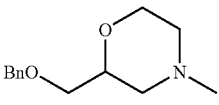 | NMR2: 2.27(6H, s), 3.05-3.08(4H, m), 3.63-6.67(2H, m) |
| 67 | 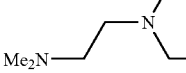 | NMR2: 1.48(9H, s), 3.12-3.19(2H, m), 6.46-6.50(2H, m) |
| 68 |  | F: 338 |
| 69 |  | F: 269  Sal: HCl |

TABLE 1-continued

R⁴—C₆H₄—NH₂ (para-substituted aniline)

| Rex | R⁴ | Dat |
|---|---|---|
| 70 | morpholine-2-CO₂Et, N-methyl | F: 250 |
| 71 | 1-methylpiperidine-4-CO₂Et | NMR2: 1.26(3H, t, J = 7.2 Hz), 3.40-3.48(4H, m), 6.62-6.66(2H, m) |
| 72 | MeO(CH₂)₂N-piperazine-N-Me | F: 236 |
| 73 | 3-(hydroxymethyl)-[1,4'-bipiperidine], 1'-methyl | ESI: 290 |
| 74 | [1,4'-bipiperidine], 1'-methyl | ESI: 260 |
| 75 | N-Boc-3-methoxyazetidine | EI: 265 |
| 76 | Boc-piperazine-CO-piperazine-N-Me | ESI: 390 |
| 77 | trans-4-hydroxy-N-methylcyclohexylamine | ESI: 207 |
| 104 | 6-methyl-morpholin-3-one | EI: 193; Sal: HCl |
| 106 | (S)-4,5-dimethylmorpholin-3-one | F: 207 |
| 107 | (R)-4,5-dimethylmorpholin-3-one | F: 207 |
| 108 | (S)-5-methylmorpholin-3-one | F: 193 |
| 109 | N-Boc-3-methylmorpholine | F: 279 |
| 110 | H₂NOC-CH₂-piperazine-N-Me | NMR1: 2.89(2H, s), 2.92-2.95(4H, m), 6.47-6.50(2H, m) |
| 111 | N-Boc-3-methoxypiperidine | NMR2: 1.46(9H, s), 4.05-4.08(1H, m), 6.67-6.79(2H, m) |

TABLE 2

Pyrimidine scaffold: R³, R⁴, R⁵ substituted phenyl—(CH₂)ₙ—NH—pyrimidine(4-SOMe, 5-CONH₂)

| Rex | R³ | R⁴ | R⁵ | n | Dat |
|---|---|---|---|---|---|
| 87 | Cl | HO | Cl | 2 | F: 389 |
| 88 | H | 4-morpholino-N-oxide-CH₂— | H | 0 | F: 392 |

TABLE 3

| Rex | Str | Dat |
|---|---|---|
| 49 | 2-[(2-hydroxyethyl)amino]benzylamine | F: 167 |
| 50 | 2-[N-methyl-N-(2-hydroxyethyl)amino]benzylamine | F: 181 |

TABLE 3-continued

| Rex | Str | Dat |
|---|---|---|
| 51 | 2-(OCF₃)-benzylamine | F: 192 Sal HCl |
| 78 | 4-amino-3-fluoro-phenethyl alcohol | F: 156 |
| 105 | 2-morpholino-3-(hydroxymethyl)-aniline (5-amino) | F: 209 Sal HCl |
| 112 | 3-amino-N-methyl-N-(2-morpholinoethyl)aniline | EI: 236 Sal HCl |
| 113 | (3-chlorothiophen-2-yl)methanamine | F: 148 Sal HCl |
| 114 | 3-(aminomethyl)-4-chlorophenol | F: 158 |
| 115 | 2-CF₃-5-F-benzylamine | F: 194 Sal HCl |
| 116 | 2,3-diF-5-F-benzylamine | F: 162 Sal HCl |
| 117 | 2-CF₃-6-F-benzylamine | F: 194 Sal HCl |
| 118 | 5-F-2-OMe-benzylamine | F: 156 Sal HCl |
| 119 | 3-((2-hydroxyethyl)amino)benzylamine | F: 167 |

TABLE 4

(Structure: R⁴-phenyl-(CH₂)ₙ-NH-pyrimidine(CO₂H)-NH-Y-B)

| Rex | R⁴ | n | Y—B | Dat |
|---|---|---|---|---|
| 79 | HO | 2 | 3-Me—Ph | F: 365 |
| 80 | HOCH₂CH₂ | 0 | 1-(3-methylphenyl)-1-hydroxyethyl | F: 395 |
| 81 | HOCH₂CH₂ | 0 | 5-methyl-1H-indol-3-yl | FN: 388 |
| 82 | HOCH₂CH₂ | 0 | 2,6-F₂—Ph | F: 387 |
| 83 | HOCH₂CH₂ | 0 | 3,5-F₂—Ph | F: 387 |
| 84 | HOCH₂CH₂ | 0 | 2,5-F₂—Ph | F: 387 |
| 85 | HOCH₂CH₂ | 0 | 3,4-F₂—Ph | NMR: 2.69(2H, t, J = 7.1 Hz), 7.32-7.44(2H, m), 8.70(1H, s) |
| 86 | HOCH₂CH₂ | 0 | 2,4-F₂—Ph | NMR: 2.67(2H, t, J = 7.1 Hz), 7.07-7.09(4H, m), 8.69(1H, s) |

TABLE 5

(Structure: X-pyrimidine(CONH₂)-NH-Y-B)

| Rex | Y—B | X | Dat |
|---|---|---|---|
| 89 | cHex | MeSO₂ | F: 299 |
| 90 | 3-CN—Ph | Cl | F: 274 |
| 91 | 6-methyl-benzo[d][1,3]dioxol-5-yl | Cl | F: 293 |
| 92 | Bn | Cl | F: 263 |
| 93 | —CH₂—(2,6-F₂—Ph) | Cl | F: 299 |
| 94 | 2-phenyl-2-hydroxypropyl | Cl | F: 293 |
| 95 | —CH₂—(2-F₃C—Ph) | Cl | FN: 329 |
| 96 | —CH₂—(2,3,6-F₃—Ph) | Cl | F: 317 |
| 97 | 3-Et—Ph | Cl | F: 277 |
| 98 | 3-F₃C—Ph | Cl | F: 317 |

TABLE 5-continued

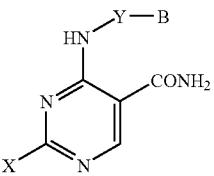

| Rex | Y—B | X | Dat |
|---|---|---|---|
| 99 | (7-methyl-2,3-dihydro-1,4-benzodioxine) | Cl | FN: 305 |
| 100 | —CH₂—(2-F—Ph) | Cl | F: 281 |
| 101 | —CH₂—(2,5-F₂—Ph) | Cl | F: 299 |
| 102 | Ph-CH(Me)- | Cl | F: 277 |
| 103 | —CH₂—(2-O₂N—Ph) | Cl | F: 308 |

TABLE 6

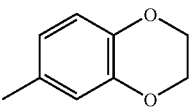

| Ex | Syn | $R^5$ | $R^1$ | $R^2$ | —Y—B | Dat |
|---|---|---|---|---|---|---|
| 1 | Ex 1 | H | H | H | Bn | F: 398; NMR1: 4.60-4.66 (2H, br m), 8.38(0.7H, s), 8.45(0.3H, s), 9.87 (1H, s) |
| 2 | Ex 2 | Cl | Me | H | 3-Me—Ph | F: 446; NMR1: 2.75-2.79 (5H, m), 8.49(0.7H, s), 8.54(0.3H, s), 9.88(1H, s) |
| 16 | Ex 1 | Cl | H | H | Bn | F: 432; NMR1: 4.60-4.66 (2H, br m), 8.38(0.7H, s), 8.45(0.3H, s), 9.85 (1H, s) |
| 17 | Pre 3 | Cl | H | H | CH₂—(2,5-F₂—Ph) | F: 468 |

TABLE 7

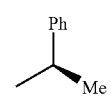

| Ex | Syn | —Y—B | Dat |
|---|---|---|---|
| 18 | Ex 3 | Bn | F: 419 |
| 19 | Pre 14 | CH₂(3-Cl—Ph) | F: 453 |
| 20 | Pre 14 | (2-ethylfuran) | F: 409 |
| 21 | Pre 14 | (2-ethylthiophene) | F: 425 |
| 22 | Pre 14 | CH₂-2Py | F: 420 |
| 23 | Pre 14 | CH₂-3Py | F: 420 |
| 24 | Pre 14 | CH₂-4Py | F: 420 |
| 25 | Pre 14 | CH₂(2-Cl—Ph) | F: 453 |
| 26 | Pre 14 | CH₂(2-F₃C—Ph) | F: 487 |
| 27 | Pre 14 | CH₂(2-MeO—Ph) | F: 449 |
| 28 | Pre 14 | CH₂(3-F₃C—Ph) | F: 487 |
| 29 | Pre 14 | CH₂(3-MeO—Ph) | F: 449 |
| 30 | Pre 14 | CH₂(4-Cl—Ph) | F: 453 |
| 31 | Pre 14 | CH₂(4-F₃C—Ph) | F: 487 |
| 32 | Pre 14 | CH₂(4-MeO—Ph) | F: 449 |

TABLE 8

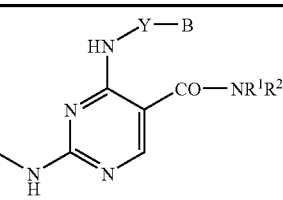

| Ex | Syn | —Y—B | Dat |
|---|---|---|---|
| 3 | Ex 3 | Bn | F: 405; NMR1: 3.71-3.74(4H, m), 4.66(2H, d, J = 6.3 Hz), 7.33-7.35(4H, m); 8.51(1H, s) |
| 7 | Ex 7 | CH₂-(2-F-6-HO—Ph) | F: 439; NMR1: 3.70-3.73(4H, m), 7.13-7.19 (1H, m), 8.47(1H, s), 10.25(1H, s) |
| 8 | Ex 8 | CH₂-(2-AcHN—Ph) | F: 462 |

TABLE 8-continued

| Ex | Syn | —Y—B | Dat |
|---|---|---|---|
| 33 | Pre 13 | CH$_2$-(2-Me—Ph) | F: 419 |
| 34 | Pre 13 | CH$_2$-(2-Cl—Ph) | F: 439; NMR1: 2.95-3.03(m, 4H), 4.72(d, 2H, J = 5.9 Hz), 7.48-7.53(m, 1H), 8.53(s, 1H) |
| 35 | Pre 13 | CH$_2$-(2-MeO—Ph) | F: 435; NMR1: 2.97-3.05(m, 4H), 3.85(s, 3H), 4.61(d, 2H, J = 5.8 Hz), 8.50(s, 1H) |
| 36 | Pre 13 | CH$_2$-(2,4-F$_2$—Ph) | F: 441 |
| 37 | Pre 13 | CH$_2$-(2,3,6-F$_3$—Ph) | F: 459; NMR1: 3.00-3.08(m, 4H), 4.83(d, 2H, J = 5.9 Hz), 7.43-7.52(1H, m), 8.52(s, 1H) |
| 38 | Pre 13 | CH$_2$-(3,5-F$_2$—Ph) | F: 441; NMR1: 2.98-3.03(m, 4H), 4.66(d, 2H, J = 5.8 Hz), 7.04-7.12(m, 1H), 8.52(s, 1H) |
| 39 | Pre 13 | CH$_2$-(2-F-5-Cl—Ph) | FN:455; NMR1: 2.98-3.04(4H, m), 4.67(d, 2H, J = 5.8 Hz), 7.34-7.39(m, 1H), 8.53(1H, s) |
| 40 | Pre 13 | CH$_2$-(2-HO—Ph) | F: 421 |
| 41 | Pre 13 | CH$_2$-(3-MeO—Ph) | F: 435; NMR1: 2.97-3.05(4H, m), 3.70(s, 3H), 4.62(2H, d, J = 5.4 Hz), 8.51(1H, s) |
| 42 | Pre 13 | CH$_2$-(2,5-(MeO)$_2$—Ph) | F: 465; NMR1: 2.96-3.04(4H, m), 3.80(s, 3H), 4.58(2H, d, J = 4.7 Hz), 8.50(1H, s) |
| 43 | Pre 13 | CH$_2$-(3-F—Ph) | F: 423; NMR1: 2.97-3.04(4H, m), 4.67(2H, d, J = 5:9 Hz), 7.34-7.41(m, 1H), 8.52(1H, s) |
| 44 | Pre 13 | CH$_2$-(3-F$_3$C—Ph) | F: 473; NMR1: 2.96-3.03(4H, m), 4.75(2H, d, J = 5.8 Hz), 6.95-7.04(m, 2H), 8.52(1H, s) |
| 45 | Pre 13 | CH$_2$-(2,3-(MeO)$_2$—Ph) | F: 465; NMR1: 2.97-3.03(4H, m), 3.82(s, 3H), 4.64(2H, d, J = 5.9 Hz), 8.50(1H, s) |
| 46 | Pre 13 | (2-ethylpyrazinyl) | F: 407 |
| 47 | Pre 13 | CH$_2$-(3-HOCH$_2$—Ph) | F: 433; NMR1: 2.95-3.04(4H, m), 4.60(2H, d, J = 5.3 Hz), 4.68(2H, d, J = 5.9 Hz), 8.51(1H, s) |
| 48 | Pre 13 | CH$_2$-(2,3-F$_2$—Ph) | F: 441; NMR1: 2.97-3.03(4H, m), 4.74(2H, d, J = 5.9 Hz), 7.28-7.36(m, 1H), 8.53(1H, s) |
| 49 | Pre 13 | CH$_2$-(4-F—Ph) | F: 423 |
| 50 | Pre 13 | CH$_2$-(2-EtO—Ph) | F: 449 |
| 51 | Pre 13 | CH$_2$-(2,4-(MeO)$_2$—Ph) | F: 465 |
| 52 | Pre 13 | CH$_2$-(2,6-Me$_2$—Ph) | F: 433 |
| 53 | Pre 13 | CH$_2$-(2-F-5-Me—Ph) | F: 437; NMR1: 2.20(3H, s), 4.66(2H, d, J = 4.5 Hz), 7.08-7.11(3H, m), 8.51(1H, s) |
| 54 | Pre 13 | CH$_2$-(2-(Et$_2$NCH$_2$)—Ph) | F: 490 |
| 55 | Pre 13 | CH$_2$-(3-HO—Ph) | F: 421; NMR1: 2.96-3.05(4H, m), 4.58(2H, d, J = 5.9 Hz), 8.51(1H, s) |
| 56 | Pre 13 | CH$_2$-(3,5-(MeO)$_2$—Ph) | F: 465 |
| 57 | Pre 13 | CH$_2$-(2-Me-3-Cl—Ph) | FN:451 |
| 58 | Pre 13 | CH$_2$-(2-Cl-6-F—Ph) | F: 457; NMR1: 3.00-3.06(4H, m), 4.84(2H, d, J = 4.4 Hz), 8.52(1H, s) |
| 59 | Pre 13 | CH$_2$-(2,6-F$_2$-3-Cl—Ph) | FN:473; NMR1: 3.01-3.07(4H, m), 4.82(2H, d, J = 5.4 Hz), 7.18-7.26(m, 1H), 8.52(1H, s) |
| 60 | Pre 13 | CH$_2$-(2-F-6-MeO—Ph) | F: 453; NMR1: 3.01-3.06(4H, m), 3.86(3H, s), 4.70(2H, d, J = 4.9 Hz); 8.48(1H, s) |
| 61 | Pre 13 | CH$_2$-(2,6-Cl$_2$—Ph) | F: 473; NMR1: 3.01-3.06(4H, m), 4.92(2H, d, J = 4.9 Hz), 7.39-7.45(m, 1H), 8.53(1H, s) |
| 62 | Ex 3 | CH$_2$-(2-F—Ph) | F: 423; NMR1: 3.01-3.03(4H, m), 4.71(2H, d, J = 5.9 Hz), 7.12-7.16(1H, m), 8.52(1H, s) |
| 63 | Ex 3 | CH$_2$-(2,6-F$_2$—Ph) | F: 441; NMR1: 4.79(2H, d, J = 5.8 Hz), 7.40-7.47(1H, m), 8.52(1H, s) |
| 64 | Ex 3 | CH$_2$-(2,5-F$_2$—Ph) | F: 441; NMR1: 2.97-3.05(4H, m), 4.68(2H, d, J = 5.9 Hz), 7.28-7.33 (1H, m), 8.53(1H, s) |
| 65 | Ex 3 | CH$_2$-(2-F$_3$C—Ph) | F: 473 |
| 66 | Pre 13 | CH$_2$-(2-HOCH$_2$—Ph) | F: 434; NMR1: 3.69-3.75(4H, m), 4.47(2H, d, J = 5.3 Hz), 4.65(2H, d, J = 5.8 Hz), 8.51(1H, s) |
| 67 | Pre 13 | CH$_2$-(2-OMe-6-Me—Ph) | F: 449; NMR1: 3.70-3.75(4H, m), 3.81(3H, s), 4.65(2H, d, J = 5.3 Hz), 8.47(1H, s) |
| 68 | Pre 13 | CH$_2$-[2-HO(CH$_2$)$_2$O—Ph] | F: 465; NMR1: 3.69-3.75(4H, m), 4.05(2H, t, J = 4.9 Hz), 4.65(2H, d, J = 5.9 Hz), 8.49(1H, s) |

TABLE 8-continued

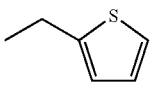

| Ex | Syn | —Y—B | Dat |
|---|---|---|---|
| 69 | Pre 13 | $CH_2$-(2-OH-5-Cl—Ph) | F: 455; NMR1: 3.71-3.76(4H, m), 4.56(2H, d, J = 5.9 Hz) 7.07-7.13(m, 1H), 8.50(1H, s) |
| 70 | Pre 13 | $CH_2$-(2-F-5-$HOCH_2$—Ph) | F: 453; NMR1: 3.71-3.74(4H, m), 4.40(2H, d, J = 5.9 Hz), 4.70(2H, d, J = 5.9 Hz), 8.52(1H, s) |
| 71 | Pre 13 | $CH_2$-[2-$HO(CH_2)_2$HN—Ph] | F: 464 Sal: 3HCl |
| 72 | Pre 13 | $CH_2$[2-$HO(CH_2)_2$N(Me)—Ph] | F: 478; NMR1: 2.70(3H, s) 3.52-3.57(2H, m) 3.70-3.73(4H, m), 4.74(2H, d, J = 5.8 Hz), 8.52 (1H, s) |
| 73 | Pre 13 | $CH_2$-(3-$Et_2NCH_2$—Ph) | F: 490 |
| 74 | Pre 13 | $CH_2$-[2,6-$(MeO)_2$O—Ph] | F: 465; NMR1: 3.71-3.75(4H, m), 3.79(6H, s), 4.66(2H, d, J = 4.9 Hz), 8.46(1H, s) |
| 75 | Pre 13 | $CH_2$-[3-$HO(CH_2)_2$O—Ph] | F: 465; NMR1: 3.70-3.75(4H, m), 3.91(2H, t, J = 4.9 Hz), 4.63(2H, d, J = 6.4 Hz), 8.51(1H, s) |
| 76 | Pre 13 | $CH_2$-(2-$CF_3$O—Ph) | F: 489 |
| 77 | Pre 13 | $CH_2$-(2-F-6-$CF_3$—Ph) | F: 491; NMR1: 3.70-3.75(4H, m), 4.85(2H, d, J = 4.0 Hz), 7.62-7.71(m, 5H), 8.53(1H, s) |
| 78 | Pre 13 | $CH_2$-(3-F-6-$CF_3$—Ph) | F: 491; NMR1: 3.69-3.74(4H, m), 4.86(2H, d, J = 5.9 Hz), 7.85-7.91(m, 1H), 8.56(1H, s) |
| 79 | Pre 13 | $CH_2$-(2-F-3-$CF_3$—Ph) | F: 491 |
| 80 | Pre 13 | $CH_2$-[2-$HO(CH_2)_3$—Ph] | F: 463; NMR1: 1.68-1.75(2H, m), 4.70(2H, d, J = 5.3 Hz), 8.53(1H, s) |
| 81 | Pre 13 | $CH_2$-[3-$HO(CH_2)_3$—Ph] | F: 463; NMR1: 1.65-1.72(2H, m), 4.63(2H, d, J = 5.9 Hz), 8.51(1H, s) |
| 82 | Pre 13 | $CH_2$-[2-$HO(CH_2)_2$—Ph] | F: 449; NMR1: 2.82(2H, t, J = 7.3 Hz), 6.80(2H, d, J = 8.8 Hz), 8.52(1H, s) |
| 83 | Pre 13 | $CH_2$-[3-$HO(CH_2)_2$—Ph] | F: 449; NMR1: 2.70(2H, t, J = 7.0 Hz), 6.82(2H, d, J = 9.3 Hz), 8.51(1H, s) |
| 84 | Pre 13 | $CH_2$-(2-MeS—Ph) | F: 451; NMR1: 3.73-3.78(4H, m), 4.67(2H, d, J = 5.3 Hz), 7.26-7.39(m, 4H), 8.52(1H, s) Sal HCl |
| 85 | Pre 13 | $CH_2$-(2,6-$(HO)_2$—Ph) | F: 437 |
| 86 | Ex 3 | $CH_2$-(2-$MeSO_2$—Ph) | F: 483 |
| 87 | Pre 13 | $CH_2$[3-$HO(CH_2)_2$N(Me)—Ph] | F: 478; NMR1: 2.87(3H, s), 3.70-3.75(4H, m), 4.57(2H, d, J = 5.8 Hz), 8.50(1H, s) Sal HCl |
| 88 | Pre 13 | $CH_2$-(3-MeO-6-F—Ph) | F: 453; NMR1: 3.75-3.78(4H, m), 3.64(3H, s), 4.70(2H, d, J = 5.4 Hz), 8.55(1H, s) |
| 89 | Phe 13 | $CH_2$-(3-$EtO_2$C—Ph) | F: 477 |
| 90 | Pre 13 | $CH_2$-[3-$HO(CH_2)_2$NH—Ph] | FN:462; NMR1: 3.70-3.75(4H, m), 4.54(2H, d, J = 5.9 Hz), 8.55(1H, s) |
| 91 | Pre 13 | $CH_2$-(2-MeO-5-F—Ph) | F: 453 NMR1: 3.71-3.75(4H, m), 3.85(3H, s), 4.60(2H, d, J = 5.9 Hz), 8.52(1H, s) |
| 92 | Pre 13 | $CH_2$-(2,3,5-$F_3$—Ph) | F: 459; NMR1: 3.71-3.76(4H, m), 4.73(2H, d, J = 5.9 Hz), 7.35-7.47(m, 3H), 8.54(1H, s) |
| 93 | Ex 3 | $CH_2$-(2-$O_2$N—Ph) | F: 450; NMR1: 3.72-3.75(4H, m), 4.95(2H, d, J = 5.9 Hz), 8.14(1H, d, J = 7.8 Hz), 8.51(1H, s) |
| 94 | Ex 7 | $CH_2$-(2-$H_2$N—Ph) | F: 420 |
| 95 | Pre 13 | $CH_2$-(3-Cl—Ph) | F: 439; NMR1: 3.70-3.75(4H, m), 4.65(2H, d, J = 5.8 Hz), 7.33-7.39(m, 2H), 8.52(1H, s) |
| 96 | Pre 13 | 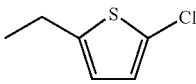 | F: 411; NMR1: 3.69-3.74(4H, m), 4.84(2H, d, J = 5.9 Hz), 7.36-7.40(m, 1H), 8.52(1H, s) |
| 97 | Pre 13 | 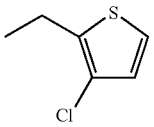 | F: 445; NMR1: 3.70-3.75(4H, m), 4.74(2H, d, J = 6.4 Hz), 8.52(1H, s) |
| 98 | Pre 13 |  | F: 445; NMR1: 3.70-3.75(4H, m), 4.79(2H, d, J = 5.8 Hz), 7.47-7.54(m, 3H), 8.54(1H, s) |

TABLE 8-continued

[Structure: morpholine-phenyl-NH-pyrimidine with CONH2 and HN-Y-B substituent]

| Ex | Syn | —Y—B | Dat |
|---|---|---|---|
| 99 | Pre 13 | 2-ethyl-thiazole | F: 412 |

TABLE 9

[Structure: R4-phenyl-NH-pyrimidine with CONH2 and HN-Y-B substituent]

| Ex | Syn | R⁴ | —Y—B | Dat |
|---|---|---|---|---|
| 4 | Ex 4 | N-ethyl piperidine N-oxide | Bn | F: 433 |
| 5 | Ex 5 | 4-methylpiperazin-1-yl (HN) | Bn | F: 404 |
| 6 | Ex 6 | 1-methyl-4-methoxypiperidine | Bn | F: 433; NMR1: 4.20-4.26(1H, m), 4.66(2H, d, J = 5.8 Hz), 8.53(1H, s) |
| 9 | Ex 9 | 1-methyl-piperidine-4-carboxylic acid | Bn | F: 447 |
| 10 | Ex 10 | MsHN-CH2-(4-methylmorpholin-2-yl) | Bn | F: 512; NMR1: 2:94(3H, s), 4.67(2H, d, J = 5.8 Hz), 8.55 (1H, s) Sal:HCl |
| 11 | Ex 11 | EtO2C-CH2-(4-methylpiperazin-1-yl) | Bn | NMR1: 1.18(3H, t, J = 7.2 Hz), 4.66 (2H, d, J = 6.0 Hz), 8.51(1H, s) |
| 12 | Ex 12 | MeHN-CH2-(4-methylmorpholin-2-yl) | Bn | F: 448; NMR1: 2.70-2.75(1H, m), 4.68(2H, d, J = 5.8 Hz), 8.61(1H, s) Sal: 2HCl |
| 13 | Ex 13 | H2N-CH2CH2-(1-methylpiperidin-4-yl) | Bn | F: 446; NMR1: 2.80-2.88(2H, m), 4.71(2H, d, J = 5.9 Hz), 8.68(1H, s) Sal: 3HCl |

TABLE 9-continued

| Ex | Syn | R⁴ | —Y—B | Dat |
|---|---|---|---|---|
| 14 | Ex 14 | methyl glucopyranoside (HO, OH, OH, OH) | Bn | F: 498 |
| 100 | Ex 3 | 1-ethyl-4-hydroxypiperidine | Bn | F: 433 |
| 101 | Ex 3 | 4-ethylthiomorpholine | Bn | F: 435 |
| 102 | Ex 3 | 1-ethylpiperidine | Bn | F: 417 |
| 103 | Ex 3 | 1-ethyl-4-methylpiperazine | Bn | F: 432; Sal: 3HCl |
| 104 | Ex 3 | 4-ethylthiomorpholine 1,1-dioxide | Bn | F: 467 |
| 105 | Ex 3 | 1-methylpiperidine | Bn | F: 403; NMR1: 3.00-3.03(4H, m), 4.66(2H, d, J = 5.9 Hz), 8.51(1H, s) |
| 106 | Ex 3 | piperidin-1-yl-(CH₂)— | Bn | F: 431 |
| 107 | Ex 3 | 4-(N-ethyl-N-methylamino)tetrahydropyran | Bn | F: 447; NMR1: 2.08(3H, s), 4.69(2H, d, J = 5.8 Hz), 8.55(1H, s) |
| 108 | Ex 3 | piperidine-1-carbonyl | Bn | F: 431; NMR1: 1.50(4H, br), 4.71 (2H, d, J = 5.9 Hz), 8.58(1H, s) |
| 109 | Ex 3 | piperidine-1-sulfonyl | Bn | F: 467 |
| 110 | Ex 3 | 1-methyl-4-(N-ethyl-N-methylamino)piperidine | Bn | F: 460 |
| 111 | Ex 3 | piperidin-1-yl-(CH₂)₃— | Bn | F: 445 |

TABLE 9-continued

| Ex | Syn | R⁴ | —Y—B | Dat |
|---|---|---|---|---|
| 112 | Ex 3 | piperidinyl-N(CH₂)₄— | Bn | F: 459 |
| 113 | Ex 3 | O₂S-thiomorpholinyl-N— | Bn | F: 453; NMR1: 3.66-3.68(4H, m), 4.67(2H, d, J = 5.9 Hz), 8.52(1H, s) |
| 114 | Ex 3 | N-methyl-2-oxopiperidinyl | Bn | F: 417; NMR1: 2.36(2H, t, J = 6.3 Hz), 4.69(2H, d, J = 5.9 Hz), 8.56(1H, s) |
| 115 | Ex 3 | MeN-4-methylpiperidinyl | Bn | F: 417 |
| 116 | Ex 3 | MeN-piperazinyl-N— | Bn | F: 418; NMR1: 2.24(3H, s), 4.66(2H, d, J = 5.8 Hz), 8.51(1H, s) |
| 117 | Ex 3 | cis-2,6-dimethyl-N-methylmorpholinyl | Bn | F: 433; NMR1: 3.65-3.72 2H, m), 4.67(2H, d, J = 6.3 Hz), 8.52(1H, s) |
| 118 | Ex 3 | trans-2,6-dimethyl-N-methylmorpholinyl | Bn | F: 433; NMR1: 4.00-4.07(2H, m), 4.66(2H, d, J = 5.8 Hz), 8.51(1H, s) |
| 119 | Ex 3 | morpholinyl-N—CO— | Bn | F: 433; NMR1: 3.49(4H, br), 4.71 (2H, d, J = 5.8 Hz), 8.58(1H, s) |
| 120 | Ex 3 | morpholinyl-N—CONH— | Bn | F: 448 |
| 121 | Ex 3 | morpholinyl-N—CON(Me)— | Bn | F: 462 |
| 122 | Ex 3 | 1,4-dimethyl-diazepanyl | Bn | F: 432 |
| 123 | Ex 3 | HO-4-hydroxy-N-methylpiperidinyl | Bn | F: 419 |

TABLE 9-continued

| Ex | Syn | R⁴ | —Y—B | Dat |
|---|---|---|---|---|
| 124 | Ex 3 | HCO—N(piperazine)N—Me | Bn | F: 432 |
| 125 | Ex 3 | iPr—N(piperazine)N—Me | Bn | F: 446; NMR1: 0.996(6H, d, J = 6.4 Hz), 4.66(2H, d, J = 5.9 Hz), 8.50(1H, s) |
| 126 | Ex 3 | MeO-CH₂CH₂-N(piperazine)N—Me | Bn | F: 462 |
| 127 | Ex 3 | (1,4-oxazepane)N—Me | Bn | F: 419; NMR1: 1.88(2H, quint, J = 5.8 Hz), 4.65(2H, d, J = 5.9 Hz), 8.56(1H, s) |
| 128 | Ex 5 | HN(piperidine)-OMe | Bn | F: 419; NMR1: 4.34-4.40(1H, m), 4.66 (2H, d, J = 5.9 Hz), 8.53(1H, s) |
| 129 | Ex 5 | HN-(2,5-diazabicyclic)-N | Bn | FN:414 |
| 130 | Ex 5 | HN(piperazine, 2,5-diMe)N—Me | Bn | F: 432 |
| 131 | Ex 6 | Me—N-(diazabicyclic)-N | Bn | F: 430 |
| 132 | Ex 6 | Me—N(piperazine, 2,5-diMe)N—Me | Bn | F: 446 |
| 133 | Pre 15 | (pyrrolidine)N—CO— | Bn | F: 417 |
| 134 | Ex 3 | (pyrrolidine)N—Me | Bn | F: 389 Sal HCl |
| 135 | Ex 3 | HO-(pyrrolidine)N—Me | Bn | F: 405; NMR1: 2.00-2.07(1H, m), 6.39(2H, d, J = 8.8 Hz), 8.48(1H, s) |

TABLE 9-continued

| Ex | Syn | R⁴ | —Y—B | Dat |
|---|---|---|---|---|
| 136 | Ex 3 | AcHN-pyrrolidine-N-Me | Bn | F: 446; NMR1: 1.81(3H, s), 4.30-4.40 (1H, m), 6.53(2H, d, J = 7.8 Hz)<br>Sal: 2HCl |
| 137 | Ex 3 | MeHN-pyrrolidine-N-Me | Bn | F: 418; NMR1: 3.84-3.87(1H, m), 4.67 (2H, d, J = 5.6 Hz), 6.57(2H, d, J = 8.3 Hz)<br>Sal: 2HCl |
| 138 | Ex 3 | morpholine-CH₂CH₂-OMe | Bn | F: 449; NMR1: 3.70-3.75(4H, m), 4.68(2H, d, J = 5.9 Hz), 8.64(1H, s)<br>Sal: 2HCl |
| 139 | Ex 3 | NC-pyrrolidine-N-Me | Bn | F: 414; NMR1: 2.17-2.15(1H, m), 4.65(2H, d, J = 5.9 Hz), 8.50(1H, s) |
| 140 | Ex 3 | Me₂N-piperidine-N-Me | Bn | F: 446; NMR1: 3.75-3.80(4H, m), 4.80(2H, d, J = 5.3 Hz), 8.56(1H, s)<br>Sal: 2HCl |
| 141 | Ex 3 | Bz-N-piperazine-N-Me | Bn | F: 508; NMR1: 3.40-3.85(4H, m), 4.66(2H, d, J = 6.3 Hz), 8.52(1H, s) |
| 142 | Ex 3 | PhO-piperidine-N-Me | Bn | F: 495<br>Sal: HCl |
| 142 | Ex 3 | Me₂N(CH₂)₂-N-piperazine-N-Me | Bn | F: 475; NMR1: 2.15(6H, s), 4.66(2H, d, J = 5.9 Hz), 8.51(1H, s) |
| 144 | Ex 3 | F-piperidine-N-Me | Bn | F: 421; NMR1: 4.66(2H, d, J = 5.4 Hz), 4.70-4.90(1H, m), 8.51(1H, s) |
| 145 | Ex 3 | F₂-piperidine-N-Me | Bn | F: 439; NMR1: 3.29-3.39(2H, m), 4.67(2H, d, J = 5.8 Hz), 8.51(1H, s) |
| 146 | Ex 3 | pyrimidine-piperazine-N-Me | Bn | F: 482; NMR1: 3.29-3.39(2H, m), 4.67(2H, d, J = 5.8 Hz), 8.51(1H, s)<br>Sal: HCl |
| 147 | Ex 3 | Me-tetrahydroisoquinoline-spiro-piperidine-N-Me | Bn | F: 534; NMR1: 3.64-3.72(2H, m), 4.71(2H, d, J = 6.3 Hz), 8.61(1H, s)<br>Sal: 3HCl |

TABLE 9-continued

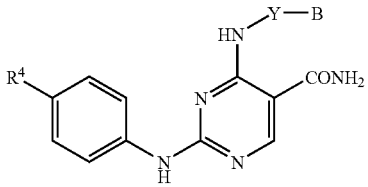

| Ex | Syn | R⁴ | —Y—B | Dat |
|---|---|---|---|---|
| 148 | Ex 3 | Me₂NCH₂CON-N(piperazine)-N-Me | Bn | F: 489; NMR1: 2.83(6H, s), 4.68(2H, d, J = 5.8 Hz), 8.60(1H, s)<br>Sal: 2HCl |
| 149 | Ex 3 | HO-CH₂CH₂-(piperidine)-N-Me | Bn | F: 447; NMR1: 1.18-1.30(2H, m), 4.66(2H, d, J = 5.9 Hz), 8.51(1H, s) |
| 150 | Ex 3 | EtO₂C-(piperidine)-N-Me | Bn | NMR1: 1.19(3H, t, J = 7.2 Hz), 4.66(2H, d, J = 6.0 Hz), 8.51(1H, s) |
| 151 | Ex 3 | morpholine-CH₂CH₂-(piperidine)-N-Me | Bn | F: 516; NMR1: 3.81-3.97(4H, m), 4.70(2H, d, J = 5.9 Hz), 8.63(1H, s)<br>Sal: 3HCl |
| 152 | Pre 4 | Me₂N-CH₂CH₂-NH-C(O)-(piperidine)-N-Me | Bn | F: 517; NMR1: 2.77(s, 3H), 3.13-3.17(2H, m), 4.70(2H, d, J = 6.4 Hz)<br>Sal: 3HCl |
| 153 | Ex 3 | Boc-HN-CH₂-(morpholine)-N-Me | Bn | F: 534; NMR1: 1.39(9H, s), 2.29(1H, t, J = 11.2 Hz), 8.51(1H, s) |
| 154 | Ex 5 | H₂N-CH₂-(morpholine)-N-Me | Bn | F: 434; NMR1: 2.70-2.75(1H, m), 4.68(2H, d, J = 5.8 Hz), 8.61(1H, s)<br>Sal: 2HCl |
| 155 | Ex 6 | Me₂N-CH₂-(morpholine)-N-Me | Bn | F: 462; NMR1: 2.68-2.74(1H, m), 4.67(2H, d, J = 5.9 Hz), 8.52(1H, s)<br>Sal: 2HCl |
| 156 | Ex 8 | AcHN-CH₂-(morpholine)-N-Me | Bn | F: 476; NMR1: 1.84(3H, s), 2.41(1H, t, J = 11.3 Hz), 8.53(1H, s)<br>Sal: HCl |
| 157 | Pre 4 | Me₂N-CH₂-C(O)-NH-CH₂-(morpholine)-N-Me | Bn | F: 519; NMR1: 4.69(2H, d, J = 5.9 Hz), 7.11(2H, brd, J = 6.8 Hz), 8.69(1H, s)<br>Sal: 2HCl |
| 158 | Ex 9 | HO₂C-CH₂-(piperazine)-N-Me | Bn | F: 462<br>Sal: HCl |

TABLE 9-continued

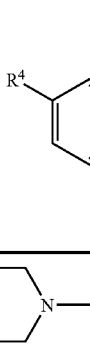

| Ex | Syn | R⁴ | —Y—B | Dat |
|---|---|---|---|---|
| 159 | Pre 4 | Me₂N(CH₂)₃CO-N(piperazinyl)-N-Me | Bn | MP: 218-223; NMR1: 2.73(3H, s), 4.69(2H, d, J = 5.8 Hz), 8.62(1H, s) Sal: 3HCl |
| 160 | Ex 3 | 2-methyl-5-oxomorpholin-3-yl (NH) | Bn | F: 419; NMR1: 4.51-4.58(1H, m), 4.78(2H, d, J = 5.8 Hz), 8.57(1H, s) |
| 161 | Ex 3 | 2-methyl-4-methyl-5-oxomorpholin-3-yl | Bn | F: 433; NMR1: 2.82(1.5H, s), 2.89 (1.5H, s), 4.70(2H, d, J = 5.9 Hz), 8.58 (0.5H, s), 8.60(0.5H, s) Sal: HCl |
| 162 | Ex 3 | 4-methyl-2-methylmorpholinyl | Bn | F: 419; NMR1: 2.74(3H, s), 4.75(2H, d, J = 6.4 Hz), 8.61(1H, s) Sal: 2HCl |
| 163 | Ex 3 | (S)-3-methyl-5-oxomorpholin-4-yl NH | Bn | F: 419; NMR1: 4.58-4.62(1H, m), 4.71(2H, d, J = 5.8 Hz), 8.61(1H, s) Sal: HCl |
| 164 | Ex 3 | (S)-3-methyl-4-methyl-5-oxomorpholine | Bn | F: 433; NMR1: 2.69(3H, s), 4.70(2H, d, J = 5.8 Hz), 8.61(1H, s) Sal: HCl |
| 165 | Ex 9 | HO₂C-CH₂-(1-methylpiperidin-4-yl) | Bn | F: 461 |
| 166 | Ex 3 | EtO₂C-CH₂-(1-methylpiperidin-4-yl) | Bn | NMR1: 1.78-1.22(3H, m), 4.66(2h, d, J = 6.0 Hz), 8.51(1H, s) |
| 167 | Ex 9 | HO₂C-CH₂CH₂-CO-(4-methylpiperazin-1-yl) | Bn | F: 504 |
| 168 | Ex 3 | MeO₂C-CH₂CH₂-CO-(4-methylpiperazin-1-yl) | Bn | NMR1: 3.58(3H, s), 4.67(2H, d, J = 4.0 Hz) 8.51(1H, s) |
| 169 | Ex 5 | (S)-3-methylmorpholinyl NH | Bn | F: 405; NMR1: 4.23-4.32(1H, m), 4.68-4.81(2H, m), 8.65(1H, s) Sal: 2HCl |

TABLE 9-continued

[Structure: 4-aminopyrimidine-5-carboxamide with R⁴-phenyl-NH at 2-position and HN-Y-B at 4-position, CONH₂ at 5-position]

| Ex | Syn | R⁴ | —Y—B | Dat |
|---|---|---|---|---|
| 170 | Ex 3 | (S)-3-methylmorpholine-N-Boc | Bn | F: 505 |
| 171 | Ex 6 | (S)-3-methyl-4-methylmorpholine | Bn | F: 419; NMR1: 4.35-4.45(1H, m), 4.71(2H, d, J = 5.9 Hz), 8.67(1H, s)<br>Sal: 2HCl |
| 172 | Ex 3 | (S)-3-methyl-morpholin-5-one | Bn | F: 419; NMR1: 4.58-4.62(1H, m), 4.71(2H, d, J = 5.8 Hz), 8.61(1H, s)<br>Sal: HCl |
| 173 | Ex 3 | (S)-3-methyl-4-methylmorpholin-5-one | Bn | F: 433; NMR1: 2.69(3H, s), 4.70(2H, d, J = 5.8 Hz), 8.61(1H, s)<br>Sal: HCl |
| 174 | Ex 5 | (S)-3-methylmorpholine | Bn | F: 405; NMR1: 4.23-4.32(1H, m), 4.68-4.81(2H, m), 8.65(1H, s)<br>Sal: 2HCl |
| 175 | Ex 3 | (R)-3-methylmorpholine-N-Boc | Bn | F: 505 |
| 176 | Ex 6 | (R)-3-methyl-4-methylmorpholine | Bn | F: 419; NMR1: 4.35-4.45(1H, m), 4.71(2H, d, J = 5.9 Hz), 8.67(1H, s)<br>Sal: 2HCl |
| 177 | Ex 3 | 2-(benzyloxymethyl)-4-methylmorpholine | Bn | F: 525; NMR1: 2.70(1H, br t, J = 10.3 Hz), 4.53(2H, s), 8.53 (1H, s)<br>Sal: HCl |
| 178 | Ex 7 | 2-(hydroxymethyl)-4-methylmorpholine | Bn | F: 435; NMR1: 2.54-2.60(1H, m), 4.68(2H, d, J = 5.9 Hz), 8.57(1H, s)<br>Sal: HCl |
| 179 | Ex 3 | 2-((N-methyl-N-trifluoroacetyl)aminomethyl)-4-methylmorpholine | Bn | F: 544 (ESI) |
| 180 | Ex 10 | 2-((N-methyl-N-methanesulfonyl)aminomethyl)-4-methylmorpholine | Bn | F: 526; NMR1: 2.86(3H, s), 2.92(3H, s), 8.55(1H, s)<br>Sal: HCl |

TABLE 9-continued

Structure: R⁴–C₆H₄–NH–[pyrimidine with CONH₂ at 5-position and HN-Y-B at 4-position]

| Ex | Syn | R⁴ | —Y—B | Dat |
|---|---|---|---|---|
| 181 | Ex 3 | Boc—HN—CH₂—[4-(1-methylpiperidinyl)] | Bn | F: 546 |
| 182 | Ex 13 | H₂N(CH₂)₃—[4-(1-methylpiperazinyl)] | Bn | F: 461; NMR1: 2.06-2.33(2H, m), 4.68 (2H, d, J = 5.9 Hz), 8.60(1H, s) Sal: 3HCl |
| 183 | Ex 3 | Boc—HN(CH₂)₃—[4-(1-methylpiperazinyl)] | Bn | F: 561 |
| 184 | Ex 3 | EtO₂C—CH₂—[4-(1-methylpiperidinyl)] | Bn | F: 543; NMR1: 1.19(3H, t, J = 7.1 Hz), 4.82(2H, d, J = 5.4 Hz), 8.51(1H, s) |
| 185 | Ex 9 | HO₂C—CH₂—[4-(1-methylpiperidinyl)] | Bn | F: 515; NMR1: 2.19(2H, d, J = 6.8 Hz), 4.82(2H, d, J = 5.9 Hz), 8.51(1H, s) |
| 186 | Ex 3 | Per-acetylated methyl glycopyranoside (AcO, AcO, OAc, OAc) | Bn | F: 666 |
| 187 | Ex 3 | 1-Methyl-3-methoxypiperidine | 2,5-difluoro-ethylphenyl | F: 469 |

TABLE 10
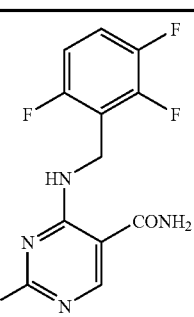
| Ex | Syn | R⁴ | Dat |
|----|-----|-----|-----|
| 15 | Ex 15 |  | F: 487; NMR1: 2.17(3H, s), 4.82(2H, d, J = 5.8 Hz), 8.52(1H, s) |
| 188 | Ex 3 | 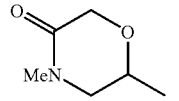 | F: 487; NMR1: 2.90(3H, s), 4.88(2H, d, J = 5.9 Hz), 8.63(1H, s)<br>Sal: HCl |
| 189 | Ex 3 | 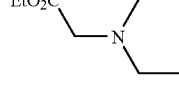 | F: 544; NMR1: 1.20(3H, t, J = 7.1 Hz), 4.83(2H, d, J = 5.4 Hz), 8.52(1H, s) |
| 190 | Ex 9 | 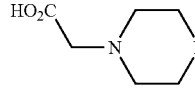 | F: 516; NMR1: 3.20(2H, s), 4.83(2H, d, J = 5.9 Hz), 8.52(1H, s) |
| 191 | Ex 3 | 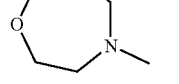 | F: 473; NMR1: 3.70-3.76(4H, m), 4.85(2H, d, J = 5.9 Hz), 8.52(1H, s)<br>Sal: HCl |
| 192 | Ex 3 | 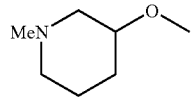 | F: 487; NMR1: 2.78(3H, d, J = 3.9 Hz), 4.81-4.89 (2H, m), 8.64(1H, s)<br>Sal: 2HCl |
| 193 | Ex 3 | 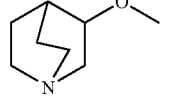 | F: 499; NMR1: 3.72-3.81(1H, m), 4.85(2H, d, J = 5.6 Hz), 8.69(1H, s)<br>Sal: 2HCl |
| 194 | Ex 5 | 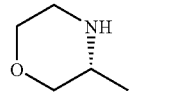 | F: 459; NMR1: 4.40-4.48(1H, m), 4.88(2H, d, J = 5.4 Hz), 8.69(1H, s)<br>Sal: 2HCl |
| 195 | Ex 3 | 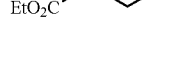 | F: 572 |
| 196 | Ex 9 |  | F: 544 |
| 197 | Ex 3 | 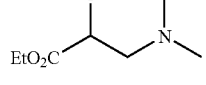 | F: 531 |

TABLE 10-continued

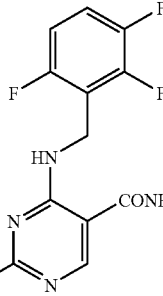

| Ex | Syn | R⁴ | Dat |
|---|---|---|---|
| 198 | Ex 9 | (morpholine-2-carboxylic acid, N-methyl) HO₂C, O, N—Me | F: 503 |
| 199 | Ex 3 | (morpholine-3-CO₂Et, N-methyl) | F: 531 NMR1: 4.59-4.64(1H, m), 4.84(2H, d, J = 5.8 Hz), 8.52(1H, s) Sal: HCl |
| 200 | Ex 3 | H₂NOC—(CH₂)₃—N(piperazine)N—Me | F: 543 NMR1: 1.63-1.70(2H, m), 4.83(2H, d, J = 5.9 Hz), 8.51(1H, s) |
| 201 | Ex 3 | H₂NOC—CH₂—N(piperazine)N—Me | F: 515 NMR1: 4.02(2H, s), 4.86(2H, d, J = 5.9 Hz), 8.67(1H, s) Sal: 2HCl |
| 202 | Ex 13 | HN(piperidine)—OMe (4-methoxy) | F: 473; NMR1: 4.25-4.32(1H, m), 4.83(2H, d, J = 5.9 Hz), 8.53(1H, s) |
| 203 | Ex 3 | Boc—N(piperidine)—OMe | F: 573 |
| 204 | Ex 3 | MeN(pyrrolidine)—OMe | F: 473; NMR1: 2.27(3H, s), 4.82(2H, d, J = 5.3 Hz), 8.52(1H, s) |
| 205 | Ex 13 | HN(piperidine)—OMe (3-methoxy) | F: 473; NMR1: 4.11-4.16(1H, m), 4.82(2H, d, J = 5.9 Hz), 8.53(1H, s) |
| 206 | Ex 3 | Boc—N(piperidine)—OMe (3-methoxy) | NMR2: 1.42(9H, s), 4.83(2H, d, J = 5.6 Hz), 8.24(1H, s) |
| 207 | Ex 11 | EtO₂C—CH₂—N(piperidine)—OMe | F: 559; NMR1: 1.17(3H, t, = 7.1 Hz), 4.82(2H, d, J = 5.8 Hz), 8.52(1H, s) |
| 208 | Ex 9 | HO₂C—CH₂—N(piperidine)—OMe | F: 531; NMR1: 1.17-1.98(4H, m), 4.83(2H, d, J = 5.9 Hz), 8.54(1H, S) |

TABLE 10-continued
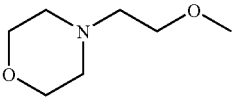
| Ex | Syn | R⁴ | Dat |
|---|---|---|---|
| 209 | Ex 3 | 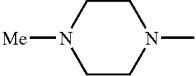 | F: 503; NMR1: 4.42-4.44(2H, m), 4.85(2H, d, J = 5.9 Hz), 8.58(1H, s)<br>Sal: 2HCl |
| 210 | Ex 3 | 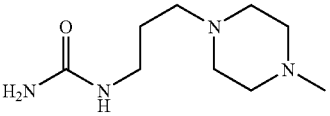 | F: 472; NMR1: 4.85(2H, d, J = 5.9 Hz) 7.01(2H, d, J = 9.2 Hz), 8.57(1H, s)<br>Sal: 2HCl |
| 211 | Ex 3 | 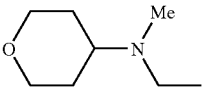 | F: 558; NMR1: 1.51-1.58(2H, m), 4.82(2H, d, J = 5.9 Hz), 8.51(1H, s) |
| 212 | Ex 3 | 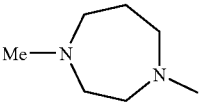 | F: 501; NMR1: 2.10(3H, s), 3.49(2H, s), 8.55 (1H, s) |
| 213 | Ex 3 | 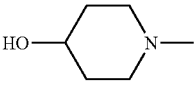 | F: 486; NMR1: 4.85(2H, d, J = 5.8 Hz), 6.78(2H, d, J = 8.3 Hz), 8.57(1H, br s)<br>Sal: 2HCl |
| 214 | Ex 3 | 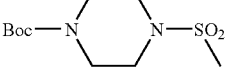 | F: 473<br>Sal: HCl |
| 215 | Ex 3 | 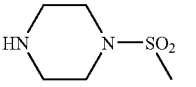 | ESI: 622 |
| 216 | Ex 5 | 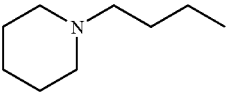 | F: 522 |
| 217 | Ex 3 | 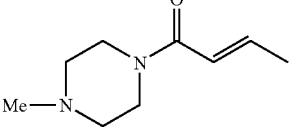 | F: 499; NMR1: 1.34-1.40(1H, m), 2.96-3.01 (2H, m), 4.88(2H, d, J = 5.8 Hz), 8.67(1H, s)<br>Sal: 2HCl |
| 218 | Ex 3 |  | F: 526<br>Sal: 2HCl |

TABLE 10-continued
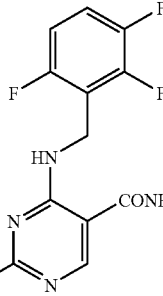
| Ex | Syn | R⁴ | Dat |
|---|---|---|---|
| 219 | Ex 3 | 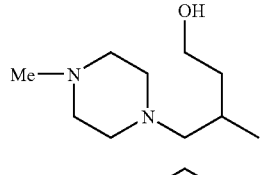 | F: 544<br>Sal:2.9HCl |
| 220 | Ex 3 | 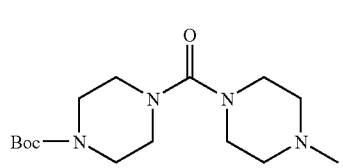 | F: 611<br>Sal:3.7HCl |
| 221 | Ex 3 | 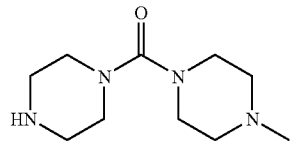 | ESI: 670 |
| 222 | Ex 5 | 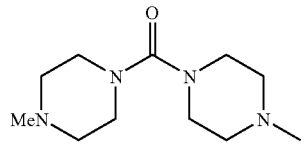 | F: 570; NMR1: 3.04-3.13(4H, m), 4.86(2H, d, J = 5.8 Hz), 7.44-7.56(4H, m), 8.65(1H, s)<br>Sal: 3HCl |
| 223 | Ex 6 | 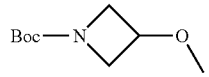 | F: 584; NMR1: 2.75(3H, d, J = 4.3 Hz), 2.95-3.07(2H, m), 4.86(2H, d, J = 5.9 Hz), 8.61(1H, s)<br>Sal:2HCl |
| 224 | Ex 3 | 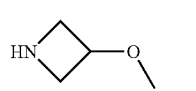 | F: 545 |
| 225 | Ex 5 |  | F: 445; NMR1: 3.93-4.03(2H, m), 4.83(2H, d, J = 5.8 Hz), 5.03-5.11(1H, m), 8.59(1H, s)<br>Sal: 2HCl |
| 226 | Ex 6 | | F: 459; NMR1: 3.98-4.07(1H, m), 4.83(2H, d, J = 5.9 Hz), 4.93-5.01(0.5H, m), 5.13-5.20(0.5H, m), 8.62(1H, s)<br>Sal: 2HCl |
| 227 | Ex 3 | 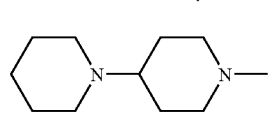 | F: 540; NMR1: 1.70-2.29(7H, m), 3.50(2H, d, J = 11.1 Hz), 4.86(2H, d, J = 5.8 Hz), 8.64(1H, s)<br>Sal: 3HCl |

TABLE 10-continued
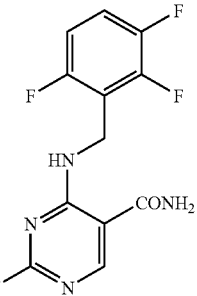
| Ex | Syn | R⁴ | Dat |
|---|---|---|---|
| 228 | Ex 3 | 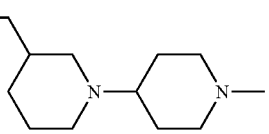 | F: 570<br>Sal: 2HCl |
| 229 | Ex 3 | 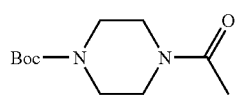 | ESI: 586 |
| 230 | Ex 5 | 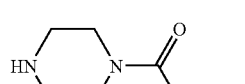 | F: 486<br>Sal: 2HCl |
| 231 | Ex 3 | 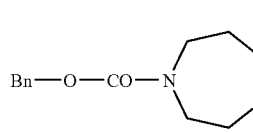 | ESI: 620 |
| 232 | Ex 7 | 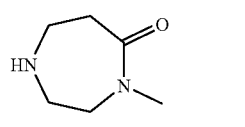 | F: 486; NMR1: 2.94-2.96 (2H, br d), 4.03(2H, br), 7.48-7.52 (1H, m), 8.60(1H, s)<br>Sal: 2HCl |
| 233 | Ex 14 | 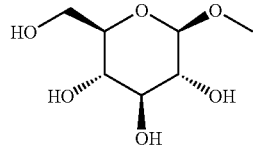 | F: 552; NMR1: 4.83(2H, d, J = 5.8 Hz), 5.25-5.30(1H, m), 8.53(1H, s) |
| 234 | Ex 14 | 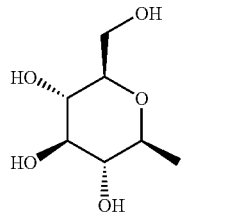 | F: 536 |
| 235 | Pre 15 | 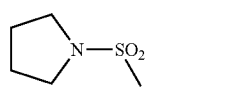 | ESI: 507 |
| 236 | Pre 15 | 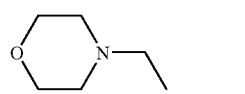 | ESI: 473 |

TABLE 10-continued

[Structure: pyrimidine core with 5-CONH₂, 4-NH-CH₂-(2,3,6-trifluorophenyl), 2-NH-(4-R⁴-phenyl)]

| Ex | Syn | R⁴ | Dat |
|---|---|---|---|
| 237 | Pre 15 | 4-ethyl-1-(N-methyl)piperazinyl (MeN-piperazine-N-ethyl) | ESI: 486 |
| 238 | Pre 15 | 4-hydroxy-1-methylpiperidinyl (HO-piperidine-N-Me) | ESI: 473 |

TABLE 11

[Structure: pyrimidine core with 5-CONH₂, 4-NH-Y-B, 2-NH-(3,4,5-trisubstituted phenyl with R³, R⁴, R⁵)]

| Ex | Syn | R³ | R⁴ | R⁵ | —Y—B | Dat |
|---|---|---|---|---|---|---|
| 239 | Ex 3 | H | morpholin-4-yl | F | Bn | F:423; NMR1: 4.69(2H, d, J = 6.4 Hz), 6.90(1H, t, J = 9.3 Hz), 8.55(1H, s) |
| 240 | Ex 3 | H | morpholin-4-yl | F₃C | Bn | F: 473 |
| 241 | Ex 3 | morpholin-4-yl | H | H | Bn | F: 405 |
| 242 | Ex 3 | morpholin-4-yl-(CH₂)₂— | H | H | Bn | F: 433; NMR1: 2.41-2.45 (2H, m), 4.72(2H, d, J = 5.9 Hz), 8.62(1H, s) |
| 243 | Ex 3 | morpholin-4-yl-CH₂— | H | H | Bn | F: 419 |
| 244 | Ex 3 | H | morpholin-4-yl | F | 2,6-difluoro-3-ethylbenzyl | F: 459; NMR1: 4.81(2H, d, J = 5.4 Hz), 6.95-7.00(1H, m), 8.55(1H, s) |

TABLE 11-continued

[Structure: R³, R⁴, R⁵ substituted phenyl-NH-pyrimidine-CONH₂ with HN-Y-B]

| Ex | Syn | R³ | R⁴ | R⁵ | —Y—B | Dat |
|---|---|---|---|---|---|---|
| 245 | Ex 3 | F | morpholin-4-yl-methyl | F | Bn | F: 441 |
| 246 | Ex 3 | F | morpholin-4-yl-methyl | H | 2-ethyl-6-fluorobenzyl | F: 441; NMR1 2.91-2.93(4H, m), 4.75(2H, d, J = 5.8 Hz), 8.57(1H, s,) |
| 247 | Ex 3 | F | morpholin-4-yl-methyl | H | 2-ethyl-4,6-difluorobenzyl | F: 459; NMR1: 4.72(2H, d, J = 6.1 Hz), 6.86-6.90(1H, m), 8.57(1H, s) |
| 248 | Ex 3 | 4-(2-methoxyethyl)morpholin-... | H | H | Bn | F: 449; NMR1 4.35-4.42(2H, m), 4.75(2H, d, J = 6.4 Hz), 8.69(1H, s) Sal: 2HCl |
| 249 | Ex 3 | 4-(2-(methylamino)ethyl)morpholin-... | H | H | Bn | F: 448; NMR1: 3.37-3.47 (4H, m), 4.73(2H, d, J = 5.8 Hz), 8.56(1H, s) Sal: 2HCl |
| 250 | Ex 3 | 4-(2-(dimethylamino)ethyl)morpholin-... | H | H | Bn | F: 462; NMR1: 2.85(3H, s), 4.74(2H, d, J = 5.8 Hz), 8.64 (1H, s) Sal: 2HCl |
| 251 | Ex 3 | 4-(2-methoxyethyl)morpholin-... | morpholin-4-yl-methyl | H | Bn | F: 534; NMR1: 3.67-3.71 (4H, s), 4.72(2H, d, J = 5.9 Hz), 8.54(1H, s) |
| 252 | Ex 3 | HOCH₂— | morpholin-4-yl-methyl | H | Bn | F: 435; NMR1: 4.53(2H, s), 4.71(2H, d, J = 5.9 Hz), 8.53 (1H, s) |
| 253 | Pre 15 | EtO₂C-piperidin-1-yl-ethyl | H | H | 2-ethyl-3,6-difluorobenzyl | ESI: 543 |

TABLE 11-continued

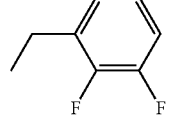

| Ex | Syn | R³ | R⁴ | R⁵ | —Y—B | Dat |
|---|---|---|---|---|---|---|
| 254 | Pre 15 | Et₂NCH₂— | H | H | 3-ethyl-2,4,6-trifluorophenyl | ESI: 459 |
| 255 | Pre 15 | HO₂C— | 2,6-dimethyl-4-methylmorpholinyl (at R⁴) | H | 3-ethyl-2,4,6-trifluorophenyl | ESI: 531 |
| 256 | Pre 15 | morpholin-4-yl | H | H | 3-ethyl-2,4,6-trifluorophenyl | ESI: 459 |
| 257 | Pre 15 | morpholin-4-ylmethyl | H | H | 3-ethyl-2,4,6-trifluorophenyl | ESI: 473 |
| 258 | Ex 3 | 2-(morpholin-4-yl)ethyl | H | H | 3-ethyl-2,4,6-trifluorophenyl | F: 487; NMR1: 3.09-3.14(4H, m), 3.81-3.87(2H, m), 4.89 (2H, d, J = 5.9 Hz), 8.68(1H, s) Sal: 2HCl |

TABLE 12

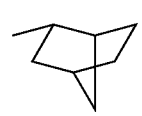

| Pre | Syn | —Y—B | Dat |
|---|---|---|---|
| 16 | — | 4-Me-cHex | F: 438 |
| 17 | — | cBu | F: 396 |
| 18 | — | cPen | F: 410 |
| 19 | — | bicycloheptyl | F: 436 |

TABLE 12-continued

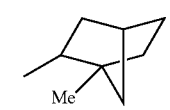

| Pre | Syn | —Y—B | Dat |
|---|---|---|---|
| 20 | — | methylbicycloheptyl | F: 478 |

TABLE 12-continued

Structure: 3,5-dichloro-4-hydroxyphenethylamine linked to pyrimidine-5-carboxamide with HN-Y-B substituent

| Pre | Syn | —Y—B | Dat |
|---|---|---|---|
| 21 | — | Ph-CH(Me)-CH2OH (2-phenylpropan-1-ol) | F: 462 |
| 22 | — | cHex-CH(Me) | F: 452 |
| 23 | — | cHep | F: 438 |
| 24 | — | cOct | F: 452 |
| 25 | — | 2Ad | F: 476 |
| 26 | — | CH2-(2-Cl—Ph) | F: 466 |
| 27 | — | CH2-(2-Br—Ph) | F: 510 |
| 28 | — | CH2-(2,6-F2—Ph) | F: 468 |
| 29 | — | CH2-(3-F—Ph) | F: 450 |
| 30 | — | CH2-(3-Cl—Ph) | F: 466 |
| 31 | — | CH2-(2,6-F2—Ph) | F: 468 |
| 32 | — | 2-ethylfuran | F: 422 |
| 33 | — | 2-ethylthiophene | F: 438 |
| 34 | — | 2-ethyltetrahydrofuran | F: 426 |
| 35 | — | CH2-tBu | F: 412 |
| 36 | — | (CH2)2CHMe2 | F: 412 |
| 37 | — | 5-methyl-1H-indole | F: 457 |
| 38 | — | 5-methyl-1H-indazole | F: 458 |
| 39 | — | 5-methyl-1,3-benzodioxole | F: 462 |
| 40 | — | 6-methyl-2,3-dihydro-1,4-benzodioxine | F: 476 |
| 41 | — | 6-methyl-1,2,3,4-tetrahydronaphthalene | F: 472 |
| 42 | — | 3-HO—Ph | F: 434 |
| 43 | — | 4-MeO—Ph | F: 448 |
| 44 | — | CH2-(2-F3C—Ph) | F: 500 |
| 45 | — | CH2-(2-MeO—Ph) | F: 462 |
| 94 | Ex 1 | cHex | F: 424 |
| 95 | Pre 3 | CH2CHMe2 | F: 398 |
| 96 | Pre 3 | CH(Me)Ph | F: 446 |
| 97 | Pre 3 | 2-ethyl-5-methylfuran | F: 436 |
| 98 | Pre 4 | 3-methyl-α-methylbenzyl alcohol (CH(Me)(OH)-(3-Me-Ph)) | F: 462 |

TABLE 13

| Pre | Syn | R³ | R⁴ | R⁵ | —Y—B | Dat |
|---|---|---|---|---|---|---|
| 1 | Pre 1 | Br | HO | H | 3-Me—Ph | F: 443; NMR1: 2.75(2H, t, J = 7.3 Hz), 8.55(0.8H, s), 8.61(0.2H, s), 9.99(1H, s) |
| 2 | Pre 2 | Cl | HO | H | 3-Et—Ph | F: 412 |
| 58 | — | Cl | HO | H | 3Qui | F: 435 |
| 59 | — | Cl | HO | H | 2-Me—Ph | F: 398 |
| 60 | — | Cl | HO | H | 3-iPr—Ph | F: 426 |

TABLE 13-continued

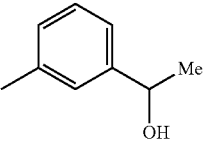

| Pre | Syn | R³ | R⁴ | R⁵ | —Y—B | Dat |
|---|---|---|---|---|---|---|
| 61 | — | Cl | HO | H | 3-HOCH₂—Ph | F: 414 |
| 62 | — | Cl | HO | H | 3-MeS—Ph | F: 430 |
| 63 | — | Cl | HO | H | 4-Me—Ph | F: 398 |
| 64 | — | Cl | HO | H | 3,5-Me₂—Ph | F: 412 |
| 65 | — | Cl | HO | H | 3,5-Cl₂—Ph | F: 453 |
| 66 | — | Cl | HO | H | 3-Ac—Ph | F: 426 |
| 67 | — | Cl | HO | H | 4-F-3-Me—Ph | F: 416 |
| 68 | — | Cl | HO | H | 2,4-F₂—Ph | F: 420 |
| 69 | — | Cl | HO | H | CH₂-(3-Me—Ph) | F: 412 |
| 99 | Pre 1 | Cl | HO | H | 3-Me—Ph | F: 398; NMR1: 2.75(2H, t, J = 6.9 Hz), 8.55(0.7H, s), 8.61(0.3H, s), 9.91(1H, s) |
| 100 | Pre 1 | H | AcNH | H | 3-Me—Ph | F: 405 |
| 101 | Pre 1 | HO | H | H | 3-Me—Ph | F: 364 |
| 102 | Pre 1 | H | MeSO₂NH | H | 3-Me—Ph | F: 441 |
| 103 | Pre 1 | H | HCOHN | H | 3-Me—Ph | F: 391 |
| 104 | Pre 1 | F | HO | H | 3-Me—Ph | F: 382; NMR1: 2.75(2H, t, J = 7.3 Hz), 8.55(0.7H, s), 8.61(0.3H, s), 9.58(1H, s) |
| 105 | Pre 1 | MeO | HO | H | 3-Me—Ph | F: 394 |
| 106 | Pre 1 | Me | HO | H | 3-Me—Ph | F: 378 |
| 107 | Pre 1 | MeO | HO | MeO | 3-Me—Ph | F: 424 |
| 108 | Pre 1 | Cl | HO | Cl | 3-Me—Ph | F: 432; NMR1: 2.77(2H, t, J = 7.3 Hz), 8.55(0.7H, s), 8.61(0.3H, s), 9.88(1H, s) |
| 109 | Pre 1 | Cl | HO | H | 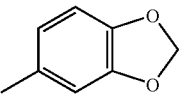 | F: 428; NMR1: 5.12(1H, d, J = 3.9 Hz), 8.54(0.7H, s), 8.61(0.3H, s), 9.90(1H, s) |
| 110 | Pre 2 | Cl | HO | H | 3-NC—Ph | F: 409 |
| 111 | Pre 2 | Cl | HO | H | 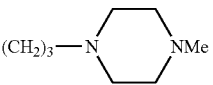 | F: 428 |
| 112 | Ex 1 | Cl | HO | H | cHex | F: 390 |

TABLE 14

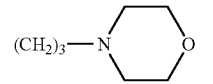

| Pre | Syn | R³ | R⁵ | R¹ | R² | —Y—B | Dat |
|---|---|---|---|---|---|---|---|
| 4 | Pre 4 | H | H | (CH₂)₂NMe₂ | H | 3-Me—Ph | F: 435 |
| 74 | — | H | H | (CH₂)₃-N(piperazine)NMe | H | 3-Me—Ph | F: 504 |
| 75 | — | H | H | (CH₂)₃-N(morpholine) | H | 3-Me—Ph | F: 491 |

TABLE 14-continued
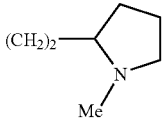
| Pre | Syn | R³ | R⁵ | R¹ | R² | —Y—B | Dat |
|---|---|---|---|---|---|---|---|
| 76 | — | H | H | (CH₂)₂OMe | H | 3-Me—Ph | F: 422 |
| 77 | — | H | H | 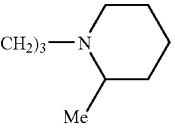 | H | 3-Me—Ph | F: 475 |
| 78 | — | H | H | (CH₂)₃NMe₂ | H | 3-Me—Ph | F: 449 |
| 79 | — | H | H | (CH₂)₃OMe | H | 3-Me—Ph | F: 436 |
| 80 | — | H | H | 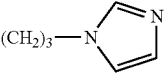 | H | 3-Me—Ph | F: 503 |
| 81 | — | H | H | 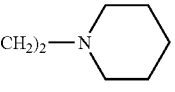 | H | 3-Me—Ph | F: 472 |
| 82 | — | H | H | OMe | H | 3-Me—Ph | F: 394 |
| 83 | — | H | H | (CH₂)₃NMe₂ | H | 3-Me—Ph | F: 463 |
| 84 | — | H | H | 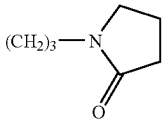 | H | 3-Me—Ph | F: 475 |
| 85 | — | H | H | (CH₂)₂—3Py | H | 3-Me—Ph | F: 469 |
| 86 | — | H | H | CH₂—3Py | H | 3-Me—Ph | F: 455 |
| 87 | — | H | H | 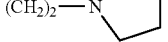 | H | 3-Me—Ph | F: 489 |
| 88 | — | H | H | 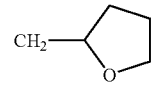 | H | 3-Me—Ph | F: 461 |
| 89 | — | H | H | 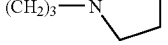 | H | 3-Me—Ph | F: 448 |
| 90 | — | H | H | (CH₂)₃—N pyrrolidine | H | 3-Me—Ph | F: 475 |
| 91 | — | H | H | 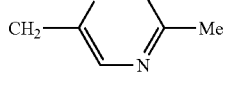 | H | 3-Me—Ph | F: 470 |
| 92 | — | H | H | (CH₂)₂SMe | H | 3-Me—Ph | F: 438 |
| 93 | — | H | H | CH₂—2Py | H | 3-Me—Ph | F: 455 |
| 113 | Ex 2 | H | H | Me | H | 3-Me—Ph | F: 378 |
| 114 | Ex 2 | H | H | Me | Me | 3-Me—Ph | F: 392 |

TABLE 14-continued

Structure: HO-phenyl(R3,R5)-CH2CH2-NH-pyrimidine(2-NH, 4-NH-Y-B, 5-CO-NR1R2)

| Pre | Syn | R³ | R⁵ | R¹ | R² | —Y—B | Dat |
|---|---|---|---|---|---|---|---|
| 115 | Ex 2 | H | H | Et | H | 3-Me—Ph | F: 392 |
| 116 | Ex 2 | H | H | ⁱPr | H | 3-Me—Ph | F: 406 |
| 117 | Ex 2 | H | H | (CH₂)₂-morpholino | H | 3-Me—Ph | F: 477 |
| 118 | Ex 2 | H | H | (CH₂)₂OH | H | 3-Me—Ph | F: 408 |
| 119 | Ex 2 | Cl | H | Me | H | 3-Me—Ph | F: 412 |
| 120 | Pre 4 | Cl | Cl | Me | H | 3-Me-Ph-CH(OH)Me | F: 476; NMR1: 1.30(3H, d, J = 6.3 Hz), 2.76-2.80(5H, m), 8.65(1H, s) Sal: HCl |
| 121 | Ex 2 | Cl | Cl | (CH₂)₂-morpholino | H | 3-Me—Ph | F: 511 Sal: 2HCl |
| 122 | Pre 4 | Cl | Cl | (CH₂)₂OH | H | 3-Me-Ph-CH(OH)Me | F: 506 Sal: HCl |

TABLE 15

Structure: HO-phenyl-CH2CH2-NH-pyrimidine(2-NH, 4-NH-Y-B, 5-CONH2)

| Pre | Syn | —Y—B | Dat |
|---|---|---|---|
| 3 | Pre 3 | -cHex | F: 356 |
| 46 | — | —CH₂-(2,6-F₂—Ph) | F: 400 |
| 47 | — | —CH₂-(2-MeO—Ph) | F: 394 |
| 48 | — | —CH₂-tBu | F: 344 |
| 49 | — | —(CH₂)₂—CHMe₂ | F: 344 |
| 50 | — | -cPen | F: 342 |
| 51 | — | —CH₂-2Py | F: 365 |
| 52 | — | —CH₂-(2-Cl—Ph) | F: 398 |
| 54 | — | —(CH₂)₃-(3-indolyl) | F: 417 |
| 53 | — | —CH₂-(3-Me—Ph) | F: 378 |
| 55 | — | —(CH₂)₂—SEt | F: 362 |
| 56 | — | —CH₂-(3,5-F₂—Ph) | F: 400 |
| 57 | — | —CH₂-(2,3-Cl₂—Ph) | F: 433 |
| 70 | — | -(2-Me—Ph) | F: 364 |
| 71 | — | -(3-MeS—Ph) | F: 396 |
| 72 | — | -(4-Me—Ph) | F: 364 |
| 73 | — | -(3,5-Me₂—Ph) | F: 378 |
| 123 | Pre 3 | —Ph | F: 350 |
| 124 | Pre 3 | -Bn | F: 364 |
| 125 | Pre 3 | —(CH₂)₂-N(morpholino)-(3-Me-Ph) | F: 463 Sal: 2HCl |
| 126 | Pre 3 | —CH₂-cHex | F: 370 |

TABLE 16

[Structure: morpholine-CH2-phenyl-NH-pyrimidine(CONH2)-NH-Y-B]

| Pre | Syn | —Y—B | Dat |
|-----|-----|------|-----|
| 13 | Pre 13 | iPr | F: 371; NMR1: 3.00-3.03 (6H, d, J = 6.8 Hz), 3.55-3.57(4H, m), 8.50(1H, s) |
| 14 | Pre 14 | cPr | F: 369 |
| 127 | Pre 13 | CH2-iPr | F: 385 |
| 128 | Pre 13 | tBu | F: 385 Sal: 2HCl |
| 129 | Ex 3 | 3-Me—Ph | F: 419 Sal: 2HCl |
| 130 | Pre 14 | cPen | F: 397 |
| 131 | Pre 14 | cHex | F: 411 |
| 132 | Pre 14 | cHep | F: 425 |
| 133 | Pre 14 | cOct | F: 439 |
| 134 | Pre 14 | (methylnorbornyl) | F: 423 |
| 135 | Pre 14 | (trans-4-hydroxycyclohexyl-methyl) | F: 427 |
| 136 | Pre 14 | (2-hydroxycyclohexyl-methyl) | F: 427 |
| 137 | Pre 14 | (1-Bn-4-methylpiperidin-4-yl) | F: 502 |
| 138 | Pre 14 | (1-Bn-pyrrolidin-3-ylmethyl) | F: 488 |
| 139 | Pre 14 | (1-Bn-pyrrolidin-3-ylmethyl) | F: 488 |
| 140 | Pre 14 | (1-methyl-1,2,3,4-tetrahydronaphthalenyl) | F: 459 |
| 141 | Pre 14 | (CH2)2OMe | F: 387 |
| 142 | Pre 14 | CH2—CN | F: 368 |
| 143 | Pre 14 | (1-ethylpyrrolidin-2-ylmethyl with Et) | F: 440 |
| 144 | Pre 14 | CH2—CH=CH2 | F: 369 |
| 145 | Pre 14 | CH2—C≡CH | F: 367 |
| 146 | Pre 14 | (tetrahydrofuran-2-ylmethyl) | F: 413 |
| 147 | Pre 14 | (neopentyl-OH, Me2C(CH2OH)CH2-) | F: 401 |
| 148 | Pre 14 | CH2CF3 | F: 411 |
| 149 | Pre 14 | CH2-cPr | F: 383 |
| 150 | Pre 14 | (CH2)2Ph | F: 433 |
| 151 | Pre 14 | C(Me)2Ph | F: 447 |
| 152 | Pre 14 | CH(Ph)(Me) CH2 | F: 433 |
| 153 | Pre 14 | CH(Ph)(Me) CH2 | F: 433 |
| 154 | Pre 14 | CH(Ph)CH2OH | F: 449 |
| 155 | Pre 14 | CH(Ph)CH2OH | F: 449 |
| 156 | Pre 14 | CH(cHex)(Me) | F: 439 |
| 157 | Pre 14 | CH(cHex)(Me) | F: 439 |
| 158 | Pre 14 | CH(Me)CH2OH (iBu-OH) | F: 387 |
| 159 | Pre 14 | CH(Me)CH2OH (sec-butanol) | F: 387 |

TABLE 17

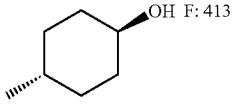

| Pre | Syn | —Y—B | Dat |
|---|---|---|---|
| 12 | Pre 12 | cHex | F: 397; NMR1: 1.95-1.98(2H, m), 3.02-3.04(4H, m), 8.47 (1H, s) |
| 160 | Pre 13 | 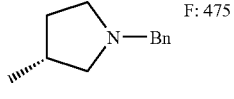 | F: 413 |
| 161 | Pre 13 | 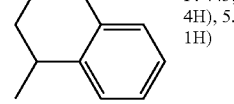 | F: 475 |
| 162 | Pre 13 | 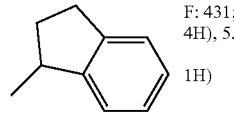 | F: 445; NMR1: 2.97-3.03(m, 4H), 5.36-5.44(m, 1H), 8.56(s, 1H) |
| 163 | Pre 13 | 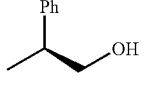 | F: 431; NMR1: 2.96-3.06(m, 4H), 5.60-5.70(m, 1H), 8.54(s, 1H) |

TABLE 17-continued

| Pre | Syn | —Y—B | Dat |
|---|---|---|---|
| 164 | Pre 13 | C(Me)$_2$—Ph | F: 433; NMR1: 1.67(6H, s), 2.94-3.02(4H, m), 8.49(1H, s) |
| 165 | Pre 13 | CH(Me)-(2-F—Ph) | F: 437; NMR1: 8.52(1H, s), 3.73-3.76(4H, m), 1.49(3H, d, J = 6.9 Hz) |
| 166 | Pre 13 | CH(2-F—Ph)-CH$_2$OH | F: 453; NMR1: 5.13-5.16(1H, m), 6.78(2H, d, J = 9.3 Hz), 8.51(1H, s) |
| 167 | Ex 3 | 3-Me—Ph | F: 405 Sal: HCl |
| 168 | Ex 3 | 3-F$_3$C—Ph | F: 459 |
| 169 | Ex 3 | CH$_2$CF$_3$ | F: 397 |
| 170 | Ex 3 | 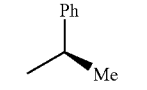 | F: 435 |
| 171 | Ex 3 | 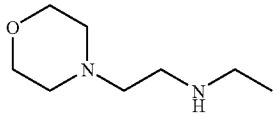 | F: 419 |
| 172 | Pre 13 | CH(Me)-(2-F—Ph) | F: 437; NMR1: 1.49(3H, d, J = 6.9 Hz), 6.79(2H, d, J = 9.1 HZ), 8.52(1H, s) |
| 173 | Pre 13 | (CH$_2$)$_2$—Ph | F: 419; NMR1: 3.62-3.70(2H, m), 3.72-3.76(4H, m), 8.48(1H, s) |

TABLE 18

| Pre | Syn | R$^4$ | —Y—B | Dat |
|---|---|---|---|---|
| 5 | Pre 5 | AcNHCH$_2$ | 3-Me—Ph | F: 391 |
| 6 | Pre 6 | H$_2$NCONHCH$_2$ | 3-Me—Ph | F: 392 |
| 7 | Pre 7 | MeNHCH$_2$ | 3-Me—Ph | F: 363 |
| 8 | Pre 8 | (morpholino-CH$_2$CH$_2$-NH-) | 3-Me—Ph | F: 462 Sal: 3HCl |
| 9 | Pre 9 | Me$_2$NCH$_2$ | 3-Me—Ph | F: 3.77 Sal: 2HCl |
| 10 | Pre 10 | HO(CH$_2$)$_2$ | 3-Me—Ph | F: 364 |
| 11 | Pre 11 | MeO | Bn | F: 350 |
| 15 | Pre 15 | H | Bn | F: 320 |

TABLE 18-continued

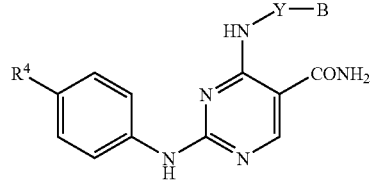

| Pre | Syn | R⁴ | —Y—B | Dat |
|---|---|---|---|---|
| 174 | Pre 4 | HO(CH₂)₂ | 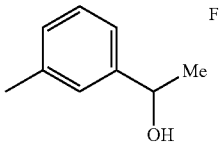 | F: 394 |
| 175 | Pre 4 | HO(CH₂)₂ | 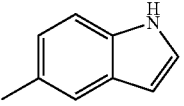 | F: 389 |
| 176 | Pre 4 | HO(CH₂)₂ | 3,5-F₂—Ph | F: 386 |
| 177 | Pre 4 | HO(CH₂)₂ | 2,5-F₂—Ph | F: 386; NMR1: 2.70(2H, t, J = 7.3 Hz), 6.84-6.90(1H, m), 8.77(1H, s) |
| 178 | Pre 4 | HO(CH₂)₂ | 2,6-F₂—Ph | F: 386 |
| 179 | Pre 4 | HO(CH₂)₂ | 3,4-F₂—Ph | F: 386 |
| 180 | Pre 4 | HO(CH₂)₂ | 2,4-F₂—Ph | F: 386; NMR1: 2.68(2H, t, J = 7.3 Hz), 7.03-7.07(1H, m), 8.72(1H, s) |
| 181 | Pre 5 | MeSO₂NHCH₂ | 3-Me—Ph | F: 427 |
| 182 | Pre 8 | 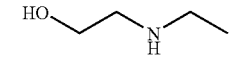 | 3-Me—Ph | F: 393<br>Sal: 2HCl |
| 183 | Pre 8 | 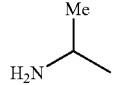 | 3-Me—Ph | F: 363; NMR1: 1.52(3H, d, J = 6.8 Hz); 2.32(3H, s), 8.86(1H, s)<br>Sal: 2HCl |
| 184 | Pre 10 | HOCH₂ | 3-Me—Ph | F: 350 |
| 185 | Pre 10 | HO | 3-Me—Ph | F: 336 |
| 186 | Pre 10 | 4-OH—Ph | 3-Me—Ph | F: 412 |
| 187 | Pre 10 | Et | 3-Me—Ph | F: 348 |
| 188 | Ex 3 | Et₂NCO | 3-Me—Ph | F: 419<br>Sal: HCl |
| 189 | Ex 3 | Me₂NCH₂ | Bn | F: 377 |
| 190 | Ex 3 | HO(CH₂)₂ | Bn | F: 364<br>Sal: HCl |
| 191 | Ex 3 | 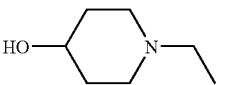 | 3-Me—Ph | F: 433<br>Sal: 2HCl |
| 192 | Ex 3 | 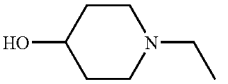 | 3-NC—Ph | F: 444 |
| 193 | Ex 3 | 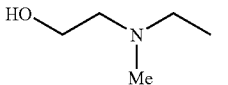 | Bn | F: 407<br>Sal: 2HCl |
| 194 | Ex 3 | 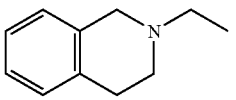 | Bn | F: 465 |
| 195 | Ex 3 | 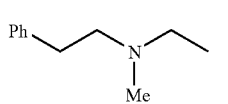 | Bn | F: 467 |

TABLE 18-continued

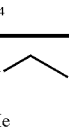

| Pre | Syn | R⁴ | —Y—B | Dat |
|---|---|---|---|---|
| 196 | Ex 3 | cHex-N(Me)-Et | Bn | F: 445; Sal: 2HCl |
| 197 | Ex 3 | (HOCH₂)₂CH | Bn | F: 394 |
| 198 | Ex 3 | HO(CH₂)₃ | Bn | F: 378 |
| 199 | Ex 3 | HO(CH₂)₂ | 3-Et—Ph | F: 378 |
| 200 | Ex 3 | HOC(CF₃)₂ | Bn | F: 486; Sal: HCl |
| 201 | Ex 3 | HO(CH₂)₂ | 3-NC—Ph | F: 375 |
| 202 | Ex 3 | HO(CH₂)₂ | 3-F₃C—Ph | F: 418 |
| 203 | Ex 3 | HO(CH₂)₂ | 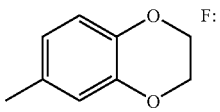 | F: 408 |
| 204 | Ex 3 | HOCH₂CMe₂ | 3-Me—Ph | F: 392; NMR1: 1.22(6H, s), 2.30(3H, s), 8.70(1H, s) |
| 205 | Ex 3 | MeO(CH₂)₂ | 3-Me—Ph | F: 378 |
| 206 | Ex 3 | HOCH₂C(Me)₂ | Bn | F: 392; NMR1: 1.19(6H, s), 4.69(2H, d, J = 5.8 Hz), 8.54(1H, s) |
| 207 | Ex 3 |  | CH₂-(2,3,6-F₃—Ph) | F: 487; NMR1: 4.04-4.12(1H, m), 4.52(1H, d, J = 4.4 Hz), 4.81(2H, d, J = 5.9 Hz), 8.48(1H, s) |
| 208 | Pre 15 | Me₂N | Bn | F: 363 |
| 209 | Pre 15 | Et₂N | Bn | F: 391 |
| 210 | Pre 15 | MeS | Bn | F: 366 |
| 211 | Pre 15 | AcHN | Bn | F: 377 |
| 212 | Pre 15 | EtO₂CCH₂ | Bn | F: 406 |
| 213 | Pre 15 | NCCH₂ | Bn | F: 359 |
| 214 | Pre 15 | 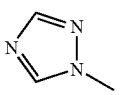 | Bn | F: 387 |
| 215 | Pre 15 | HO | Bn | F: 336 |
| 216 | Pre 15 | MeSO₂ | Bn | F: 398 |
| 217 | Pre 15 | Ac | CH₂-(2,3,6-F₃—Ph) | ESI: 416 |
| 218 | Pre 15 | CH₃(CH₂)₃O— | CH₂-(2,3,6-F₃—Ph) | ESI: 446 |
| 219 | Pre 15 | 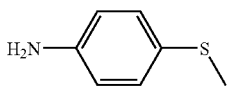 | CH₂-(2,3,6-F₃—Ph) | ESI: 497 |
| 220 | Pre 15 | 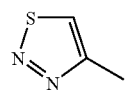 | CH₂-(2,3,6-F₃—Ph) | ESI: 458 |
| 221 | Pre 15 | Ph—HN— | CH₂-(2,3,6-F₃—Ph) | ESI: 465 |
| 222 | Pre 15 |  | CH₂-(2,3,6-F₃—Ph) | ESI: 459 |
| 223 | Pre 15 | BnO—CONH— | CH₂-(2,3,6-F₃—Ph) | ESI: 537 |

TABLE 18-continued

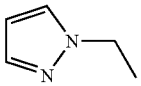

| Pre | Syn | R⁴ | —Y—B | Dat |
|---|---|---|---|---|
| 224 | Pre 15 | 1-ethyl-pyrazole | CH₂-(2,3,6-F₃—Ph) | ESI: 454 |
| 225 | Pre 15 | AcN(Me)— | CH₂-(2,3,6-F₃—Ph) | ESI: 445 |
| 226 | Pre 15 | EtO— | CH₂-(2,3,6-F₃—Ph) | ESI: 418 |

TABLE 19

| Pre | Syn | R³ | R⁴ | R⁵ | —Y—B | Dat |
|---|---|---|---|---|---|---|
| 227 | Ex 3 | morpholino-(CH₂)₂ | H | H | 3-Me—Ph | F: 433 |
| 228 | Ex 3 | morpholinomethyl | H | H | 3-Me—Ph | F: 405 |
| 229 | Ex 3 | H | HO(CH₂)₂ | F | Bn | F: 382 |
| 230 | Ex 3 | H | 5-methyl-oxazole | MeO | Bn | F: 417 |
| 231 | Ex 3 | F | morpholinomethyl | H | Ph | F: 437; NMR1: 1.50(3H, d, J = 6.9 Hz), 2.93-2.95(4H, m), 8.54(1H, s) |
| 232 | Ex 3 | F | morpholinomethyl | H | Ph | F: 453; NMR1: 2.93-2.95 (4H, m), 5.07-5.09(1H, m), 8.53(1H, s) |
| 233 | Pre 15 | MeO | H | H | Bn | F: 350 |
| 234 | Pre 15 | Ac | H | H | Bn | F: 362 |
| 235 | Pre 15 | HO | H | H | Bn | F: 336 |
| 236 | Pre 15 | HOCH₂ | H | H | Bn | F: 350 |
| 237 | Pre 15 | MeS | H | H | Bn | F: 366 |
| 238 | Pre 15 | MeO | MeO | H | Bn | F: 380 |
| 239 | Pre 15 | Cl | HO | H | Bn | F: 370 |
| 240 | Pre 15 | Et₂NCH₂— | HO— | H | 2-ethyl-3,6-difluoro-phenyl (F-substituted) | ESI: 475 |

TABLE 19-continued
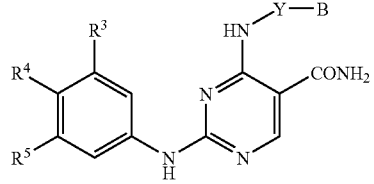
| Pre | Syn | R³ | R⁴ | R⁵ | —Y—B | Dat |
|---|---|---|---|---|---|---|
| 241 | Pre 15 | Cl | MeO— | H |  | ESI: 438 |
| 242 | Pre 15 | BuNH—SO₂— | H | H | 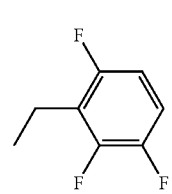 | ESI: 509 |
| 243 | Pre 15 | F | MeO— | H | 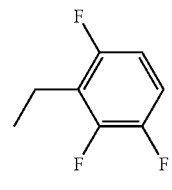 | ESI: 422 |
| 244 | Pre 15 | HO—CH(Me)— | H | H | 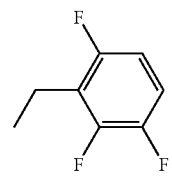 | ESI: 418 |
| 245 | Pre 15 | BnOCONH— | H | H | 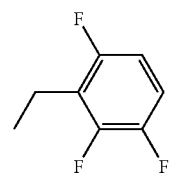 | ESI: 537 |
| 246 | Pre 15 | HOH₂C— | HO— | H | 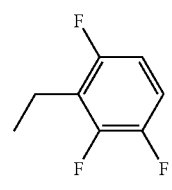 | ESI: 420 |

TABLE 20
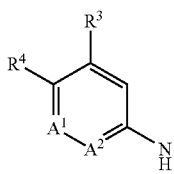
| Pre | Syn | R¹ | | —Y—B | Dat |
|---|---|---|---|---|---|
| 247 | Pre 9 | Me | 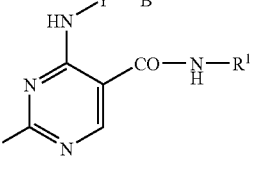 | 3-Me—Ph | F: 391 |
| 248 | Pre 11 | H | 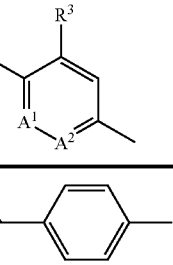 | Bn | F: 392 |
| 249 | Ex 3 | H | 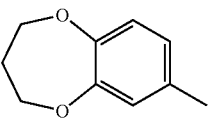 | Bn | F: 382 |
| 250 | Ex 3 | H | 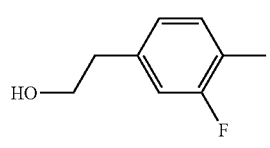 | 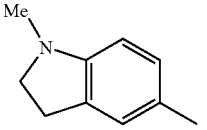 | FN: 417 |
| 251 | Ex 3 | H | 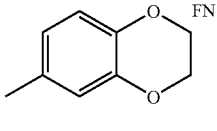 | CH$_2$-(2-F—Ph) | FN: 393; NMR1: 2.64(3H, s), 4.71(2H, d, J = 6.4 Hz), 8.50(1H, s) |
| 252 | Ex 3 | H | 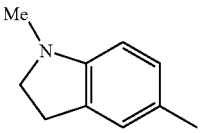 | Bn | F: 389 |
| 253 | Ex 3 | H | 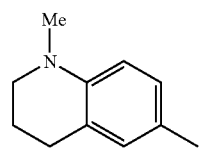 | Bn | F: 389; NMR1: 2.28(3H, s), 4.70(2H, d, J = 6.3 Hz), 8.55(1H, s) |
| 254 | Ex 3 | H | 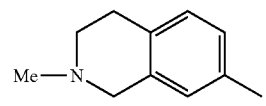 | Bn | F: 375; NMR1: 3.14-3.18(2H, m), 4.66(2H, d, J = 5.9 Hz), 8.49(1H, s) |
| 255 | Ex 3 | H | 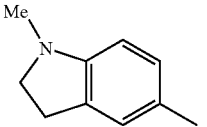 | Bn | F: 375 |

TABLE 20-continued
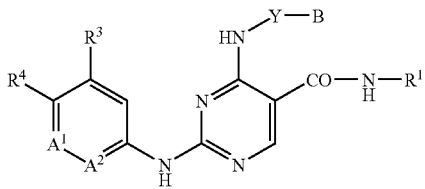
| Pre | Syn | R¹ | | —Y—B | Dat |
|---|---|---|---|---|---|
| 256 | Ex 3 | H | 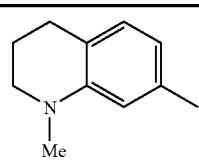 | Bn | F: 389 |
| 257 | Ex 3 | H | 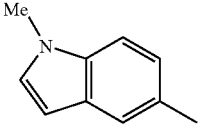 | Bn | F: 373 |
| 258 | Ex 3 | H | 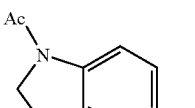 | Bn | F: 403; NMR1: 2.11(3H, s), 4.69 (2H, d, J = 5.9 Hz), 8.55(1H, s) |
| 259 | Pre 15 | H | 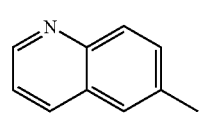 | Bn | F: 371 |
| 260 | Pre 15 | H | 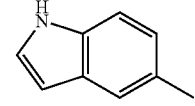 | Bn | F: 359 |
| 261 | Pre 15 | H | 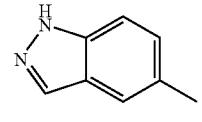 | Bn | F: 360 |
| 262 | Pre 15 | H | 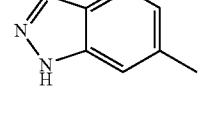 | Bn | F: 360 |
| 263 | Pre 15 | H | 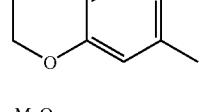 | Bn | F: 378 |
| 264 | Pre 15 | H | 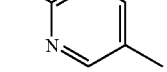 | Bn | F: 351 |

TABLE 20-continued
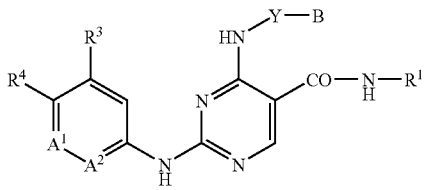
| Pre | Syn | R¹ | | —Y—B | Dat |
|---|---|---|---|---|---|
| 265 | Ex 3 | H | 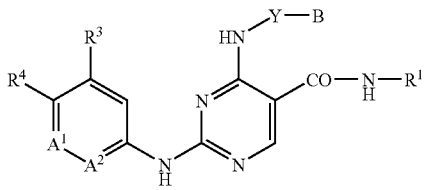 | Bn | F: 403; NMR1: 2.99(3H, s), 4.76 (2H, d, J = 5.8 Hz), 8.63(1H, s) Sal: 2HCl |
| 266 | Ex 3 | H | 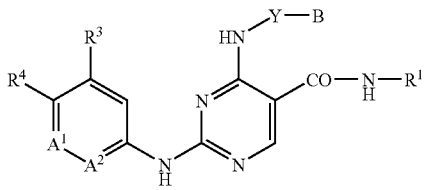 | Bn | F: 406 Sal: 2HCl |
| 267 | Ex 3 | H | 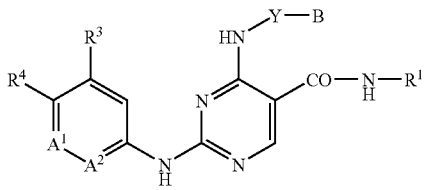 | Bn | F: 389; NMR1: 2.97(3H, s), 4.73 (2H, d, J = 5.9 Hz), 8.63(1H, s) Sal: 2HCl |
| 268 | Ex 3 | H | 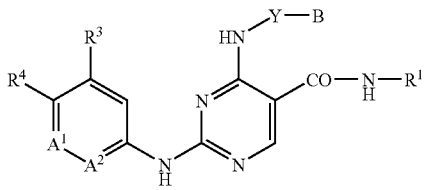 | Bn | F: 403 Sal: HCl |
| 269 | Ex 3 | H | 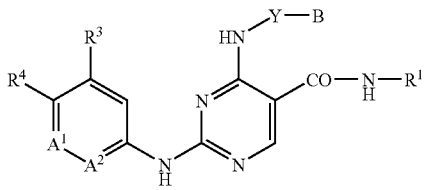 | 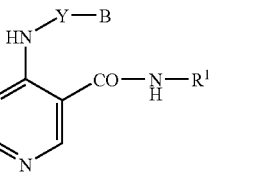 | F: 445; NMR1: 2.84(3H, s), 4.86 (2H, d, J = 5.9 Hz), 8.59(1H, s) Sal: HCl |
| 270 | Pre 15 | H | 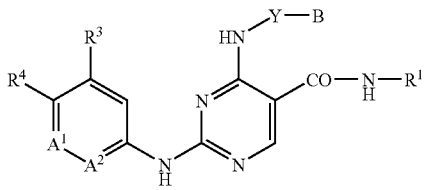 | 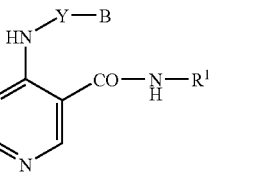 | ESI: 427 |
| 271 | Pre 15 | H | 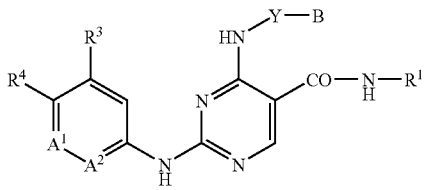 | 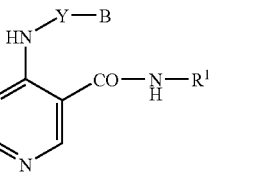 | ESI: 431 |

TABLE 20-continued
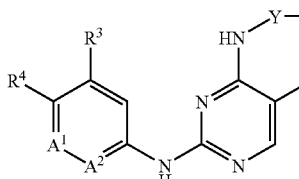
| Pre | Syn | R¹ | | —Y—B | Dat |
|---|---|---|---|---|---|
| 272 | Pre 15 | H | 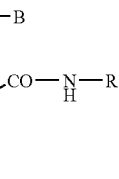 | 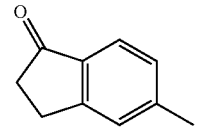 | ESI: 428 |
| 273 | Pre 15 | H | 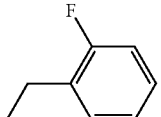 | 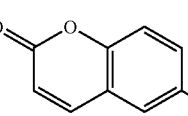 | ESI: 442 |
| 274 | Pre 15 | H | 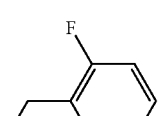 | 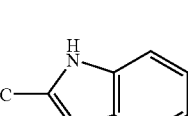 | ESI: 482 |
| 275 | Pre 15 | H | 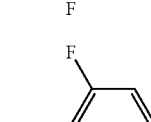 | 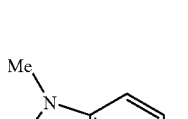 | ESI: 427 |
TABLE 21
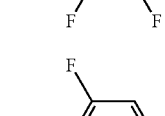
| Cmpd | —Y—B |
|---|---|
| 1 | (1-ethylnaphthalene) |
| 2 | (4-ethyl-1-methylindole) |

TABLE 21-continued
| Cmpd | —Y—B |
|---|---|
| 3 | 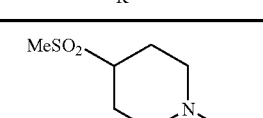 |
| 4 | 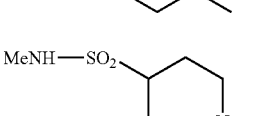 |
| 5 | 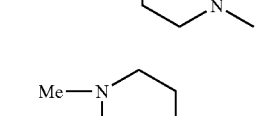 |
| 6 | 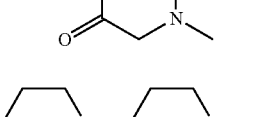 |
| 7 | 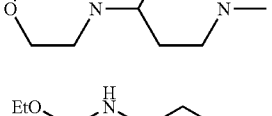 |
| 8 | 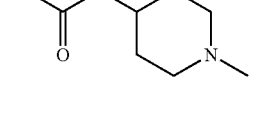 |
| 9 | 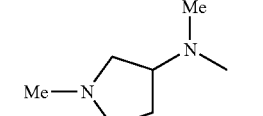 |
TABLE 22
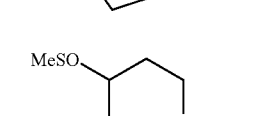
| Cmpd | R⁴ |
|---|---|
| 10 | 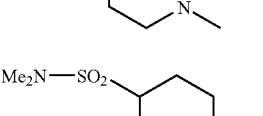 |
| 11 | 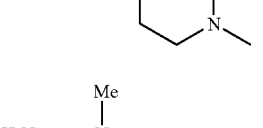 |
| 12 | Me-N piperazinone N-Me |
| 13 | morpholine-piperidine-N-Me |
| 14 | EtO-C(O)-NH-piperidine-N-Me |
| 15 | Me-N pyrrolidine NMe₂ |
| 16 | MeSO-piperidine-N-Me |
| 17 | Me₂N—SO₂-piperidine-N-Me |
| 18 | H₂N-C(O)-N(Me)-piperidine-N-Me |
| 19 | cHex—O-C(O)-NH-piperidine-N-Me |

TABLE 22-continued

| Cmpd | R⁴ |
|---|---|
| 20 | 3-(dimethylamino)-1-methylpyrrolidin-2-one |
| 21 | 1-methylpiperidin-4-yl sulfamoyl (H₂N-SO₂-) |
| 22 | N-(1-methylpiperidin-4-yl)methanesulfonamide |
| 23 | 1,3-dimethyl-1-(1-methylpiperidin-4-yl)urea (MeNH-C(O)-N(Me)-) |
| 24 | 1-methyl-3-(1-methylpiperidin-4-yl)urea (MeNH-C(O)-NH-) |

TABLE 23

| Cmpd | R⁴ | Y—B |
|---|---|---|
| 25 | N-cyano-N'-methyl-N''-(1-methylpiperidin-4-yl)guanidine | 2,6-difluoro-ethylphenyl |
| 26 | (1-methylpyrrolidin-2-yl)methyl methyl ether | 2-fluoro-ethylphenyl |

TABLE 23-continued

| Cmpd | R⁴ | Y—B |
|---|---|---|
| 27 | N-(1-hydroxypropan-2-yl)morpholine-4-carboxamide | 2,6-difluoro-ethylphenyl |
| 28 | methyl 3-(2-oxopyrrolidin-1-yl)butanoate | 2-fluoro-ethylphenyl |
| 29 | 2-(4-methylpiperazin-1-yl)-1,4,5,6-tetrahydropyrimidine | 2,6-difluoro-ethylphenyl |
| 30 | 1-(1-methylpiperidin-4-yl)ethan-1-one | 2,3-difluoro-ethylphenyl |
| 31 | N-methyl-1-methylpiperidine-4-carboxamide | 2,3,6-trifluoro-ethylphenyl |
| 32 | 2-acetyl-1,2,3,4-tetrahydroisoquinoline | 2,5-difluoro-ethylphenyl |
| 33 | N-methoxy-8-methyl-8-azabicyclo[3.2.1]octan-3-imine | 2,3-difluoro-ethylphenyl |
| 34 | 1-isopropyl-3-methoxypiperidine | 2-fluoro-ethylphenyl |

TABLE 23-continued

| Cmpd | R⁴ | Y—B |
|---|---|---|
| 35 | N-methylquinuclidin-3-yl(methyl)amine | 2-ethyl-3,6-difluorophenyl |
| 36 | 4-methyl-3-oxopiperazin-1-yl | 2-ethyl-6-fluorophenyl |
| 37 | methyl 3-(morpholine-4-carboxamido)butanoate | 2-ethyl-3,6-difluorophenyl |
| 38 | 3-(piperidin-1-yl)butan-1-ol | 2-ethyl-3,6-difluorophenyl |
| 39 | 1-(piperidin-1-yl)-2-(piperidin-1-yl)propane | 2-ethyl-5-fluorophenyl |
| 40 | 1-methyl-4-(methylsulfonyl)piperidine | 2-ethyl-6-fluorophenyl |
| 41 | 2-(methylthio)-6-(hydroxymethyl)tetrahydro-2H-pyran-3,4,5-triol | 2-ethyl-3,6-difluorophenyl |
| 42 | 2-amino-6-(hydroxymethyl)tetrahydro-2H-pyran-3,4,5-triol | 2-ethyl-3,6-difluorophenyl |
| 43 | 1-methylpiperidin-4-one oxime | 2-ethyl-6-fluorophenyl |
| 44 | 2-(3-methoxypiperidin-1-yl)ethanol | 2-ethyl-5-fluorophenyl |
| 45 | 1,4-dimethyl-1,4-diazepan-5-one | 2-ethyl-3,6-difluorophenyl |
| 46 | N-(1-methylpiperidin-3-yl)-N-methylacetamide | 2-ethyl-6-fluorophenyl |
| 47 | 2-methyl-2,8-diazaspiro[4.5]decan-3-one | 2-ethyl-6-fluorophenyl |
| 48 | 4-(4-methoxycyclohexyl)morpholine | 2-ethyl-5-fluorophenyl |
| 49 | 1-methyl-3-(1-methylpiperidin-4-yl)guanidine | 2-ethyl-3,6-difluorophenyl |

TABLE 23-continued

| Cmpd | R⁴ | Y—B |
|---|---|---|
| 50 | H₂N-CO-(1-methylpiperidin-3-yl) | 2,3-difluoro-6-ethylphenyl |
| 51 | MeN-piperazinyl-CH₂-CH(Me)-CH₂-morpholinyl | 2,3-difluoro-6-ethylphenyl |
| 52 | MeN-piperazinyl-C(O)-CH(Me)-CH₂-CO₂Me | 2,3-difluoro-6-ethylphenyl |
| 53 | methyl furanoside (HO, HO, HOCH₂) | 2,3-difluoro-6-ethylphenyl |
| 54 | 1-methyl-4-(methylthio)piperidine | 2,6-difluoro-3-ethylphenyl |
| 55 | 1,4-dimethyl-1,4-diazepan-5-one | 2-fluoro-6-ethylphenyl |
| 56 | 1-methyl-3-(methylamino)piperidine | 2,6-difluoro-3-ethylphenyl |
| 57 | 1-methyl-3-(N-methyl-N-mesylamino)piperidine | 2,5-difluoro-6-ethylphenyl |
| 58 | morpholinyl-CH₂-C(Me)₂- | 2-fluoro-6-ethylphenyl |
| 59 | morpholinyl-CH₂CH₂-C(cyclopentyl)-CH₂CH₂-OMe | 2,3-difluoro-6-ethylphenyl |
| 60 | N-methyl-N-methyl-glucopyranosylamine | 2,3-difluoro-6-ethylphenyl |
| 61 | 1-methyl-4-(ethoxycarbonyl)piperazine | 2,3-difluoro-6-ethylphenyl |
| 62 | 6-acetyl-2-methyl-1,2,3,4-tetrahydroisoquinoline | 2,3-difluoro-6-ethylphenyl |
| 63 | MeN-piperazinyl-C(O)-CH₂-CH(Me)-pyrrolidinyl | 2,3-difluoro-6-ethylphenyl |
| 64 | 1-methyl-3-(dimethylamino)piperidine | 2,3-difluoro-6-ethylphenyl |

TABLE 23-continued

![Structure: R4-phenyl-NH-pyrimidine(HN-Y-B)(CONH2)]

| Cmpd | R⁴ | Y—B |
|---|---|---|
| 65 | 4-(N-methyl-N-acetylamino)-cyclohexyl with HO | CH₂-(2,3-difluorophenyl) |
| 66 | AcO-CH₂-tetrahydropyran(OH,OH,OMe) sugar | CH₂-(2,3,4-trifluorophenyl) |

TABLE 24

![Structure: R3-phenyl-NH-pyrimidine(HN-Bn)(CONH2)]

| Cmpd | R³ |
|---|---|
| 67 | morpholino-N—CO—CH₂— |
| 68 | morpholino-N—(CH₂)₂S— |
| 69 | morpholino-N—(CH₂)₂—S(O)— |
| 70 | 1-Me-3-methoxy-piperidinyl |
| 71 | 1-Me-3-(methylamino)-piperidinyl |
| 72 | 1-Me-4-ethyl-piperazinyl |

TABLE 25

![Structure: HO-CH₂-C(Me)(Me)-phenyl-NH-pyrimidine(HN-CH₂-B)(CONH₂)]

| Cmpd | B |
|---|---|
| 73 | 2-F—Ph |
| 74 | 2,5-F₂—Ph |
| 75 | 3,5-F₂—Ph |
| 76 | 2,6-F₂—Ph |

EXAMPLE 259

Measurement of STAT 6-Dependent Reporter Activity

1) Construction of STAT 6 Reactive Reporter Plasmid

A STAT 6 reporter plasmid pGL2-CI was prepared by the following method. Synthetic DNA molecules (SEQ ID NOs:1 and 2) containing a C/EBP binding sequence contained in the germ line c promoter sequence and an IL-4 reactive sequence in tandem were annealed and inserted into XhoI and BglII sites of pGL2-Basic vector (Promega). Also, DATA box sequence DNA molecules (SEQ ID NOs:3 and 4) contained in the adenovirus major late promoter were annealed and inserted into BglII and HindIII sites of the same vector. Thereafter, pGL2-CI/bs was constructed by inserting the blasticidin resistance gene of pUCV-SD (Funakoshi) into BamHI site of the constructed pGL2-CI.

2) Construction of STAT 6 Reporter Cell

Gene transfer of pGV-CI/bs into a human IL-4 reactive cell FW4 cell (*Mol. Cell. Biol.,* 14: 5433-5440) was carried out by the electroporation method (320 V, 960 µF/0.4 cm cuvette (Nippon Bio-Rad Laboratories)), and 6 µg/ml of blasticidin (Funakoshi) was added 40 hours thereafter to select a resistant cell. Confirmation of constant transfer of the reporter plasmid was carried out by detecting Lucifer's induce by IL-4 stimulation. An STAT 6 reporter cell CI/FW4 was constructed by the above operation.

3) STAT Reporter Assay Using CI/FW4 Cell

Stimulation of the CI/FW4 cell ($1 \times 10^4$ cells/0.1 ml) with 10 ng/ml of human IL-4 (Genzyme Techne) was carried out using a white 96 well plate (Nunc). In the case of the evaluation of compounds, compound dilutions were added to the wells before inoculating the cells into the 96 well plate. Also, regarding the dilution of compounds, dilution was carried out using 10% FBS-containing RPMI 1640 such that the final concentration of DMSO in which each compound was dissolved became 0.1% or less. A 50 µl portion of a cell lysis buffer (10 mM Tris-HCl pH 7.8, 0.5 mM $MgCl_2$, 10 mM dithiothreitol and 0.1% (v/v) Triton X-100) was added 16 hours after the IL-4 stimulation, followed by stirring for 1 minute. Thereafter, 50 µl of a Lucifer's substrate solution (10 mM Tris-HCl pH 7.8, 5 mM Lucifer in, 2 mM coenzyme A, 2 mM ATP, 0.5 mM $MgCl_2$ and 2 mM $Mg(OH)_2$) was added, followed by stirring for 1 minute. Then, the Lucifer's activity was measured using ML3000 luminometer (Dynatech Laboratories, Inc). Inhibitory activities of tested compounds were evaluated in which the luminescence intensity (relative light unit: RLU) of measured value by ML3000 when DMSO was added instead of a compound was regarded as 100%, and the RLU when IL-4 stimulation was not carried out as 0%.

The results are shown in the following Table 26. Ex indicates Example compound number, Pre indicates Production Example compound number, Inh indicates inhibition ratio each compound is 1 µM or 0.1 µM, and NT indicates not tested. Also, ref 1 and ref 2 are compounds disclosed in WO 99/31073 as the most desirable compounds, and ref 1 is the compound described in Example 15 (2-(2-aminoethylamino)-4-(3-methylanilino)pyramiding-5-carboxamide) and ref 2 is the compound described in Example 35 (2-(cis-2-aminocyclohexylamino)-4-(3-methylanilino)pyramiding-5-carboxamide).

TABLE 26

| | Inh (%) | |
|---|---|---|
| | 1 µM | 0.1 µM |
| Ex | | |
| 1 | 100 | 89 |
| 2 | 96 | 48 |
| 3 | 100 | 100 |
| 35 | 100 | 95 |
| 37 | 100 | 100 |
| 38 | 100 | 100 |
| 39 | 100 | 100 |
| 62 | 100 | 99 |
| 63 | 100 | 100 |
| 64 | 100 | 100 |
| 125 | 100 | 100 |
| 127 | 100 | 96 |
| 128 | 100 | 94 |
| 148 | 100 | 94 |
| 180 | 100 | 91 |
| 189 | 100 | 100 |
| 190 | 100 | 100 |
| 191 | 100 | 100 |
| 192 | 100 | 100 |
| 193 | 10 | 100 |
| 201 | 100 | 100 |
| 209 | 100 | 100 |
| 233 | 100 | 25 |
| 244 | 100 | 97 |
| 258 | 100 | 98 |
| Pre | | |
| 1 | 100 | 67 |
| 9 | 91 | 33 |
| 12 | 100 | 91 |
| 127 | 100 | 60 |
| 178 | 100 | 69 |
| 253 | 100 | 94 |
| 269 | 100 | 96 |
| ref 1 | 19 | NT |
| ref 1 | 0 | NT |

In addition, the Example and Production Example compounds shown below also showed good activity similar to the compounds shown in the above Table 26: Examples 16, 43, 48, 58, 60, 72, 84, 96, 98, 117, 239 and 249, and Production Examples 99, 109, 204 and 265.

EXAMPLE 260

Measurement of STAT 6 Tyrosine Phosphorylation

The H292 cell (ATCC) ($5\times10^5$ cells/0.5 ml) was inoculated into a 12 well plate (IWAKI) and cultured overnight, and then stimulation with 10 ng/ml of human IL-4 (Genzyme techne) was carried out. In the case of the evaluation of compounds, compound dilutions were added to the wells 20 minutes before the IL-4 stimulation. Also, regarding the dilution of compounds, dilution was carried out using 10% FBS-containing RPMI 1640 such that the final concentration of DMSO in which each compound was dissolved became 0.1% or less. This was washed three times with ice-cooled physiological phosphate buffer 20 minutes after the IL-4 stimulation. After the washing, 100 µl/well of a cell lysis solution (TNE buffer: 10 mM Tris-HCl pH 7.8, 1% NP-40, 0.15 M NaCl, 1 mM EDTA, 10 µg/ml apportioning, 1 mM NaF and 1 mM $Na_3VO_4$) was added. The cell lysate was recovered, and 15 µl thereof was subjected to western blotting after SDS electrophoresis using an anti-tyrosine phosphorylated STAT 6 antibody (Cell Signaling). Whether or not the tyrosine phosphorylation band of about 110 kDa is disappeared, which is IL-4 stimulation-dependently detected, was judged. Also, uniform transference of the STAT 6 protein was confirmed using the same transfer membrane by western blotting which used an anti-STAT 6 antibody (Santa Cruz).

As a result of the above test, it was confirmed that tyrosine phosphorylation was inhibited by the compounds of the present invention. For example, it was completely inhibited by 1 µM of the compounds of Examples 3, 37, 35, 60, 72, 84, 96, 98, 148, 189, 190, 191, 192, 193, 201, 209 and 249 and Production Examples 99, 265 and 269.

EXAMPLE 261

Measurement of Th2 Differentiation

T cells were prepared by removing nylon wool (Wako Pure Chemical Industries)-adhering cells from C57BL/6 mouse (Charles River Japan) spleen cells. Using a 96 well plate to which an anti-CD3 ε antibody (10 µg/ml) (Sederlane) had been immobilized in advance, T cells ($2\times10^5$ cells/0.2 ml) were inoculated under stimulation with anti-CD28 antibody (1 µg/ml) (Pharmingen), IL-2 (10 ng/ml) (Peprotech) and IL-4 (10 ng/ml) (Peprotech). After 2 days of the culturing, total volume of the cell suspension was diluted to 2 ml with a medium containing IL-2 (10 ng/ml) and IL-4 (10 ng/ml). The differentiation was induced by further carrying out the culturing for 3 days. By counting the cell density, the cells after differentiation were adjusted to $1\times10^6$ cells/ml and inoculated into a 96 well plate immobilized with the anti-CD3 ε antibody, in order to induce IL-4 production. The supernatant after 24 hours of the stimulation was recovered, and the IL-4 production was determined by an ELISA method. The antibody used in the ELISA was purchased from Pharmingen. Also, an HRPO-labeled streptoavidin (Amersham Pharmacia) was used in the detection of biotinylated antibody, and a peroxides color developing reagent (Sumitomo Bakelite) was used in the HRPO color development. In the case of the evaluation of compounds, compound dilutions were added to the wells before the addition of T cells, at the time of the dilution 2 days later, compounds equivalent to the initial concentration were added. Also, regarding the dilution of compounds, dilution was carried out using 10% FBS-containing RPMI 1640 such that the final concentration of DMSO in which each compound was dissolved became 0.1% or less. Inhibitory activity of each tested compound was evaluated in which the IL-4 production when DMSO was added instead of the compound was regarded as 100%, and the IL-4 production when anti-CD28 antibody and IL-4 were not added as 0%. The inhibition ratio of each tested compound at a concentration of 10 nM is shown in the following Table 27.

TABLE 27

| Ex | Inh (%) |
|---|---|
| 1 | 88 |
| 3 | 98 |
| 16 | 82 |
| 35 | 94 |
| 37 | 93 |
| 48 | 92 |
| 60 | 99 |
| 63 | 96 |
| 64 | 93 |
| 117 | 85 |
| Pre | |
| 99 | 85 |
| ref 1 | 0 |
| ref 2 | 0 |

EXAMPLE 262

Evaluation Using Mouse Asthma Model

Active sensitization of female Balb/c mice were carried out by intraperitoneally administering ovalbumin (OA) and an adjuvant, aluminum hydroxide gel (alum), twice. Mice were exposed to OA by inhalation 12 days after the initial sensitization and sacrificed by bloodletting 72 hours after the exposure, and then alveolar lavage was carried out. A compound to be tested or a control, 0.5% methyl cellulose, was orally administered for 3 days from before the OA exposure to before the alveolar lavage. After the measurement of total white blood cell count in the alveolar lavage fluid, cell smear preparations were stained to calculate existing ratio of eosinophil based on its morphological characteristics. The total number of eosinophils was calculated from the total white blood cell count and existing ratio of respective kinds of cells. As a result, hydrochloride of the compound of Example 3 inhibited about 60% of the antigen-induced eosinophil infiltration by its oral administration at a dose of 1 mg/kg.

EXAMPLE 263

Evaluation using $SO_2$ gas-induced intra-alveolar neutrophil infiltration model Male C57BL/6 mice were exposed to $SO_2$ gas (600 ppm) for 3 hours and sacrificed by bloodletting 48 hours after the exposure, and then alveolar lavage was carried out. After the measurement of total white blood cell count in the alveolar lavage fluid, cell smear preparations were stained to calculate existing ratio of neutrophil based on its morphological characteristics. The number of neutrophils was calculated from the total white blood cell count and existing ratio of respective cells. A compound to be tested or a control, 0.5% methyl cellulose, was orally administered for 2 days from just before the exposure or just after the exposure to before the alveolar lavage. As a result, hydrochloride of the compound of Example 3 inhibited about 70% of the neutrophil infiltration by its oral administration at a dose of 10 mg/kg.

EXAMPLE 264

Evaluation Using Tobacco- and Ozone-Induced Intra-Alveolar Neutrophil Infiltration Model Male B6C3F1 mice were exposed to 3% tobacco smoke 3-hours per day for 3 consecutive days, from the 1st day to the 3rd day. On the 4th day, they were exposed to 0.5 ppm of ozone for 6 hours and sacrificed by bloodletting on the 5th day, and then alveolar lavage was carried out. After the measurement of total white blood cell count in the alveolar lavage fluid, cell smear preparations were stained to calculate existing ratio of Europhile based on its morphological characteristics. The total number of neutrophils was calculated from the total white blood cell count and existing ratio of respective cells. A compound to be tested or a control, 0.5% methyl cellulose, was administered just before the tobacco exposure or after completion of its exposure and before the ozone exposure.

It is evident that the compounds useful as the active ingredients of the present invention have excellent inhibitory activities for STAT 6 activation and Th2 differentiation from the results of the aforementioned Examples 259 to 261, and that they are useful as preventive or therapeutic agents for respiratory diseases and the like in which STAT 6 is concerned, such as asthma, COPD and the like from the results of the Examples 262 to 264.

The invention claimed is:

1. A compound represented by a formula (I) or salt thereof,

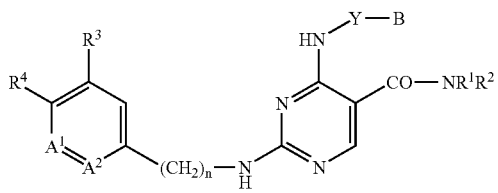

(I)

wherein $A^1$: $CR^5$ or N, $R^5$: —H, -lower alkyl, —O-lower alkyl or -halogen, $A^2$: $CR^6$ or N, $R^6$: —H or -halogen, $R^3$: —$R^0$, -lower alkyl substituted with halogen, -halogen, —$OR^0$, —S-lower alkyl, —CO-lower alkyl, —$CO_2$-lower alkyl, -lower alkylene-OH, -hetero ring, —O-hetero ring, —$N(R^0)$-hetero ring, -lower alkylene-hetero ring, —O-lower alkylene-hetero ring, —S-lower alkylene-hetero ring, —SO-lower alkylene-hetero ring, —$SO_2$-lower alkylene-hetero ring, —$N(R^0)$-lower alkylene-hetero ring, -lower alkylene-CO-hetero ring, -lower alkylene-$N(R^0)_2$, —$SO_2$—$N(R^0)$-lower alkyl or -lower alkylene-$N(R^0)$—$CO_2$-lower alkylene-phenyl, $R^0$: the same or different from one another, and each is H or a lower alkyl, n: 0 or 2, $R^4$: (i) when n=2, —$R^0$, -lower alkyl substituted with halogen, —$OR^0$, —$N(R^0)$—CHO, —$N(R^0)$—CO-lower alkyl or —$N(R^0)$—$SO_2$-lower alkyl, (ii) when n=0, —H, -lower alkyl substituted with halogen, —OH, —NH—CHO, —$CON(R^0)_2$, -lower alkylene substituted with halogen-OH, -lower alkylene-$NH_2$, -lower alkylene-$NHCONH_2$, -lower alkylene-$CO_2H$, -lower alkylene-$CO_2$-lower alkyl, -lower alkylene-CN, or —CH(lower alkylene-OH)$_2$, or a group represented by a formula —$X^a$—$R^{4a}$, $X^a$: single bond, —O—, —CO—, —S—, —$SO_2$—, —$N(R^0)$—, —$N(R^0)$CO—, —$N(R^0)SO_2$—, -lower alkylene-O—, -lower alkylene-$N(R^0)$—, -lower alkylene-$N(R^0)$CO—, -lower alkylene-$N(R^0)SO_2$—, -lower alkylene-$N(R^0)CO_2$—, —N(CO—$R^0$)—, —N($SO_2$-lower alkyl)-, —$CON(R^0)$—, -lower alkylene-O—CO—, -lower alkenylene-CO—, -lower alkenylene-$CON(R^0)$—, -lower alkenylene-$CO_2$—, —O—$(CH_2)_k$-cycloalkylene-$(CH_2)_m$—, —$N(R^0)$—$(CH_2)_k$-cycloalkylene-$(CH_2)_m$—, —CO—$(CH_2)_k$-cycloalkylene-$(CH_2)_m$—, —$CON(R^0)$—$(CH_2)_k$-cycloalkylene-$(CH_2)_m$— or —$N(R^0)CO$—$(CH_2)_k$-cycloalkylene-$(CH_2)_m$-, k and m, the same or different from each other, and each is 0, 1, 2, 3 or 4, $R^{4a}$: lower alkyl, phenyl, hetero ring, cycloalkyl, lower alkylene-phenyl, lower alkylene-hetero ring, lower alkylene-OH, lower alkenyl, lower alkenylene-phenyl or lower alkenylene-hetero ring, wherein the hetero rings in $R^3$ and $R^{4a}$ may be substituted with 1 to 5 of lower alkyl, halogen, —$OR^0$, —S-lower alkyl, —S(O)-lower alkyl, —$SO_2$-lower alkyl, lower alkylene-$OR^0$, —$N(R^0)_2$, —$CO_2R^0$, —$CON(R^0)_2$, —CN, —CHO, —$SO_2N(R^0)_2$, —$N(R^0)$—$SO_2$-lower alkyl, —N(R⁰)—CO—N(R⁰)₂, —N(R⁰)—CO₂-lower alkyl, —N(R⁰)—CO₂-cycloalkyl, —NH—C(=NH)—NH-lower alkyl, —NH—C(=N—CN)—NH-lower alkyl, hetero ring (said hetero ring may be substituted with 1 to 5 substituents selected from lower alkyl, OH and lower alkylene-OH), -lower alkylene-NH—C(=NN)—NH₂, —O-phenyl, —CO-phenyl, —N(R⁰)—CO-lower alkyl, —N(R⁰)—CO-lower alkylene—N(R⁰)₂, -lower alkylene-N(R⁰)—CO-lower alkylene-N(R⁰)₂, —CO—N(R⁰)-lower alkylene-N(R⁰)₂, —CO-lower alkylene-N(R⁰)₂, —CO-lower alkylene-CO₂R⁰, -lower alkylene-N(R⁰)₂, -lower alkylene-CO₂R⁰, -lower alkylene-CO—N(R⁰)₂, -lower alkylene-N(R⁰)—CO-lower alkyl, -lower alkylene-N(R⁰)—CO₂-lower alkyl, -lower alkylene-N(R⁰)—SO₂-lower alkyl, -lower alkylene-hetero ring (said hetero ring may be substituted with 1 to 5 substituents selected from lower alkyl, OH and lower alkylene-OH), -lower alkylene-O-lower alkylene-phenyl, =N—O—R⁰ or oxo, and phenyl and cycloalkyl may be substituted with 1 to 5 of lower alkyl, OH, O-lower alkyl or N(R⁰)₂, and wherein the lower alkylene in R³, R⁴, R⁴ᵃ and Xᵃ may be substituted with 1 to 5 of —OR⁰, —CO₂R⁰, —CON(R⁰)₂, —N(R⁰)₂, —N(R⁰)COR⁰ or hetero ring, or R³ and R⁴ may together form *—N(R⁷)—(CH₂)₂—, *—(CH₂)₂—N(R⁷)—, *—CH₂—N(R⁷)—CH₂—, *—N(R⁷)—(CH₂)₃—, *—(CH₂)₃—N(R⁷)—, *—CH₂—N(R⁷)—(CH₂)₂—, *—(CH₂)₂—N(R⁷)—CH₂—, *—C(O)—N(R⁷)—(CH₂)₂—, *—(CH₂)₂—N(R⁷)—C(O)—, *—N(R⁷)—CH=CH—, *—CH=CH—N(R⁷)—, *—N=CH—CH—, *—CH=N—CH=CH—, *—CH=CH—N=CH—, *—CH=CH—CH=N—, *—N=CH—CH=N—, *—CH=N—N=CH—, *—N(R⁷)—N=CH—, *—CH=N—N(R⁷)—, *—O—CH₂—O—, *—O—(CH₂)₂—O—, *—O—(CH₂)₃—O—, *—O—(CH₂)₂—N(R⁷)—, *—(CH₂)₂—C(O)—, *—CH=CH—C(O)—O— or *—N=C(CF₃)—NH—, wherein * indicates bonding to the position shown by R³, R⁷: —H, -lower alkyl or —CO-lower alkyl, B: cycloalkyl which may have a substituent(s), Y: single bond, and R¹ and R²: the same or different from each other, and each represents H, lower alkyl or O-lower alkyl which may have a substituent(s)).

2. A compound represented by a formula (Ia) or a salt thereof,

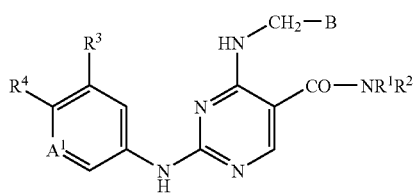

(Ia)

wherein

A¹: CR⁵ or N,

R⁵: —H, -lower alkyl, —O-lower alkyl or -halogen,

R³: —R⁰, -lower alkyl substituted with halogen, -halogen, —OR⁰, —S-lower alkyl, —CO-lower alkyl, —CO₂-lower alkyl, -lower alkylene-OH, -saturated hetero ring, -Xᵇ-heteroaryl, -Xᵇ-saturated hetero ring, —Xᵇ-heteroaryl, -lower alkylene-N(R⁰)₂, —SO₂—N(R⁰)-lower alkyl or -lower alkylene-N(R⁰)—CO₂-lower alkylene-phenyl, Xᵇ: -lower alkylene-, —O-lower alkylene-, —S-lower alkylene-, —SO-lower alkylene-, —SO₂-lower alkylene-, —N(R⁰)-lower alkylene- or -lower alkylene-CO—, R⁰: the same or different from one another, and each represents H or a lower alkyl, R⁴: —Xᵃ-saturated hetero ring, -lower alkylene-saturated hetero ring or -lower alkenylene-saturated hetero ring, Xᵃ: single bond, —O—, —CO—, —S—, —SO₂—, —N(R⁰)—, —N(R⁰)CO—, —N(R⁰)SO₂—, -lower alkylene -O—, -lower alkylene-N(R⁰)—, -lower alkylene-N(R⁰)CO— or -lower alkylene-N(R⁰)SO₂—, -lower alkylene-N(R⁰)CO₂—, —N(CO—R⁰)—, —N(SO₂-lower alkyl)-, —CON(R⁰)—, -lower alkylene-O—CO—, -lower alkenylene-CO—, -lower alkenylene-CON(R⁰)—, -lower alkenylene-CO₂—, —O—(CH₂)ₖ-cycloalkylene-(CH₂)ₘ—, —N(R⁰)—(CH₂)ₖ-cycloalkylene-(CH₂)ₘ—, —CO—(CH₂)ₖ-cycloalkylene (CH₂)ₘ—, —CON(R⁰)—(CH₂)ₖ-cycloalkylene-(CH₂)ₘ— or —N(R⁰)CO—(CH₂)ₖ-cycloalkylene-(CH₂)ₘ—, k and m: the same or different from each other, and each is 0, 1, 2, 3 or 4, wherein the saturated hetero rings in R³ and R⁴ᵃ may be substituted with 1 to 5 of lower alkyl, halogen, —OR⁰, —S-lower alkyl, —S(O)-lower alkyl, —SO₂-lower alkyl, lower alkylene-OR⁰, —N(R⁰)₂, —CO₂R⁰, —CON(R⁰)₂, —CN, —CHO, —SO₂N(R⁰)₂, —N(R⁰)—SO₂-lower alkyl, —N(R⁰)—CO—N(R⁰)₂, —N(R⁰)—CO₂-lower alkyl, —N(R⁰)—CO₂-cycloalkyl, —NH—C(=NH)—NH-lower alkyl, —NH—C(=N—CN)—NH-lower alkyl, saturated hetero ring (said hetero ring may be substituted with 1 to 5 substituents selected from lower alkyl, OH and lower alkylene-OH), heteroaryl, -lower alkylene NH—C(=NN)—NH₂, —O-phenyl, —CO-phenyl, —N(R⁰)—CO-lower alkyl, —N(R⁰)—CO-lower alkylene -N(R⁰)₂, -lower alkylene (R⁰)—CO-lower alkylene-N(R⁰)₂, —CO—N(R⁰)-lower alkylene-N(R⁰)₂, —CO-lower alkylene-N(R⁰)₂, —CO-lower alkylene-CO₂R⁰, -lower alkylene-N(R⁰)₂, -lower alkylene-CO₂R⁰, -lower alkylene-CO—N(R⁰)₂, -lower alkylene-N(R⁰)—CO-lower alkyl, -lower alkylene-N(R⁰)—CO₂-lower alkyl, -lower alkylene-N(R⁰)—SO₂-lower alkyl, -lower alkylene-hetero ring (said hetero ring may be substituted with 1 to 5 substituents selected from lower alkyl, OH and lower alkylene-OH), -lower alkylene-O-lower alkylene-phenyl, =N—O—R⁰ or oxo, and phenyl and cycloalkyl may be substituted with 1 to 5 of lower alkyl, OH, O-lower alkyl or N(R⁰)₂, and wherein the lower alkylene in R³, R⁴ and Xᵃ may be substituted with 1 to 5 of —OR⁰, —CO₂R⁰, —CON(R⁰)₂, —N(R⁰)₂, —N(R⁰)COR⁰ or hetero ring, or R³ and R⁴ may together form *—N(R⁷)—(CH₂)₂—, *—(CH₂)₂—N(R⁷)—, *—CH₂—N(R⁷)—CH₂—, *—N(R⁷)—(CH₂)₃—, *—(CH₂)₃—N(R⁷)—, *—CH₂—N(R⁷)—(CH₂)₂—, *—(CH₂)₂—N(R⁷)—CH₂—, *—C(O)—N(R⁷)—(CH₂)₂—, *—(CH₂)₂—N(R⁷)—C(O)—, *—N(R⁷)—CH=CH—, *—CH=CH—N(R⁷)—, *—N=CH—CH=CH—, *—CH=N—CH=CH—, *—CH=CH—N=CH—, *—CH=CH—CH=N—, *—N=CH—CH=N—, *—CH=N—N=CH—, *—N(R⁷)—N=CH—, *—CH=N—N(R⁷)—, *—O—CH₂—O—, *—O—

(CH₂)₂—O—, *—O—(CH₂)₃—O—, *—O—(CH₂)₂—N(R⁷)—, *—(CH₂)₂—C(O)—, *—CH═CH—C(O)—O— or *—N═C(CF₃)—NH—, wherein * indicates bonding to the position shown by R³, R⁷: —H, -lower alkyl or —CO-lower alkyl, B: aryl which may have a substituent(s) or heteroaryl which may have a substituent(s), and R¹ and R²: the same or different from each other, and each represents H, lower alkyl or O-lower alkyl which may have a substituent(s)).

3. A compound represented by a formula (Ib) or a salt thereof,

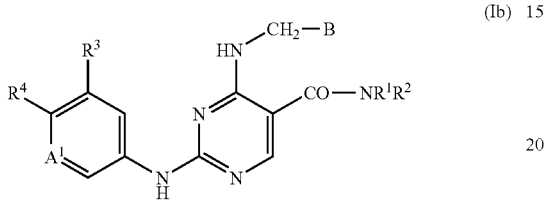

wherein
A¹: CR⁵ or N,
R⁵: —H, -lower alkyl, —O-lower alkyl or -halogen,
R³: -saturated hetero ring or —Xᵇ-saturated hetero ring,
Xᵇ: -lower alkylene-, —O—, —N(R⁰)—, —O-lower alkylene-, —S-lower alkylene-, —SO-lower alkylene-, —SO₂-lower alkylene-, —N(R⁰)-lower alkylene- or -lower alkylene-CO—,
R⁰: the same or different from one another, and each represents H or a lower alkyl,
R⁴: —H, -lower alkyl substituted with halogen, —OH, —NH—CHO, —CON(R⁰)₂, -lower alkylene substituted with halogen-OH, -lower alkylene-NH₂, -lower alkylene-NHCONH₂, -lower alkylene-CO₂H, -lower alkylene-CO₂-lower alkyl, -lower alkylene-CN, —CH(lower alkylene-OH)₂ or -Xa-R⁴ᵃ,
Xᵃ: single bond, —O—, —CO—, —S—, —SO₂—, —N(R⁰)—, —N(R⁰)CO—, —N(R⁰)SO₂—, -lower alkylene -O—, -lower alkylene-N(R⁰)—, -lower alkylene-N(R⁰)CO— or -lower alkylene-N(R⁰)SO₂—, -lower alkylene-N(R⁰)CO₂—, —N(CO—R⁰)—, —N(SO₂-lower alkyl)-, —CON(R⁰)—, -lower alkylene-O—CO—, -lower alkenylene-CO—, -lower alkenylene-CON(R⁰)—, -lower alkenylene-CO₂—, —O—(CH₂)ₖ-cycloalkylene-(CH₂)ₘ—, —N(R⁰)—(CH₂)ₖ-cycloalkylene-(CH₂)ₘ—, —CO—(CH₂)ₖ-cycloalkylene -(CH₂)ₘ—, —CON(R⁰)—(CH₂)ₖ-cycloalkylene-(CH₂)ₘ— or —N(R⁰)CO—(CH₂)ₖ-cycloalkylene-(CH₂)ₘ—,
k and m: the same or different from each other, and each is 0, 1, 2, 3 or 4,
R⁴ᵃ: lower alkyl, phenyl, heteroaryl, cycloalkyl, lower alkylene-phenyl, lower alkylene-heteroaryl, lower alkylene-OH, lower alkenyl, lower alkenylene-phenyl or lower alkenylene-heteroaryl,
wherein the saturated hetero ring and heteroaryl in R³ and R⁴ᵃ may be substituted with 1 to 5 of lower alkyl, halogen, —OR⁰, —S-lower alkyl, —S(O)-lower alkyl, —SO₂-lower alkyl, lower alkylene-OR⁰, —N(R⁰)₂, —CO₂R⁰, —CON(R⁰)₂, —CN, —CHO, —SO₂N(R⁰)₂, —N(R⁰)—SO₂-lower alkyl, —N(R⁰)—CO—N(R⁰)₂, —N(R⁰)—CO₂-lower alkyl, —N(R⁰)—CO₂-cycloalkyl, —NH—C(═NH)—NH-lower alkyl, —NH—C(═N—CN)—NH-lower alkyl, hetero ring (said hetero ring may be substituted with 1 to 5 substituents selected from lower alkyl, OH and lower alkylene-OH), -lower alkylene-NH—C(═NN)—NH₂, —O-phenyl, —CO-phenyl, —N(R⁰)—CO-lower alkyl, —N(R⁰)—CO-lower alkylene -N(R⁰)₂, -lower alkylene-NR)—CO-lower alkylene-N(R⁰)₂, —CO—N(R⁰)-lower alkylene-N(R⁰)₂, —CO-lower alkylene-N(R⁰)₂, —CO-lower alkylene-CO₂R⁰, -lower alkylene-N(R⁰)₂, -lower alkylene-CO₂R⁰, -lower alkylene-CO—N(R⁰)₂, -lower alkylene-N(R⁰)—CO-lower alkyl, -lower alkylene-N(R⁰)—CO₂-lower alkyl, -lower alkylene-N(R⁰)—SO₂-lower alkyl, -lower alkylene-hetero ring (said hetero ring may be substituted with 1 to 5 substituents selected from lower alkyl, OH and lower alkylene-OH), -lower alkylene-O-lower alkylene-phenyl, ═N—O—R⁰ or oxo, and phenyl and cycloalkyl may be substituted with 1 to 5 of lower alkyl, OH, O-lower alkyl or N(R⁰)₂, or the lower alkylene in R³, R⁴, R⁴ᵃ and Xᵃ may be substituted with 1 to 5 of —OR⁰, —CO₂R⁰, —CON(R⁰)₂, —N(R⁰)₂, —N(R⁰)COR⁰ or hetero ring, or R³ and R⁴ may together form *—N(R⁷)—(CH₂)₂—, *—(CH₂)₂—N(R⁷)—, *—CH₂—N(R⁷)—CH₂—, *—N(R⁷)—(CH₂)₃—, *—(CH₂)₃—N(R⁷)—, *—CH₂—N(R⁷)—(CH₂)₂—, *—(CH₂)₂—N(R⁷)—CH₂—, *—C(O)—N(R⁷)—(CH₂)₂—, *—(CH₂)₂—N(R⁷)—C(O)—, *—N(R⁷)—CH═CH—, *—CH═CH—N(R⁷)—, *—N═CH—CH═CH—, *—CH═N—CH═CH—, *—CH═CH—N═CH—, *—CH═CH—CH═N—, *—N═CH—CH═N—, *—CH═N—N═CH—, *—N(R⁷)—N═CH—, *—CH═N—N(R⁷)—, *—O—CH₂—O—, *—O—(CH₂)₂—O—, *—O—(CH₂)₃—O—, *—O—(CH₂)₂—N(R⁷)—, *—(CH₂)₂—C(O)—, *—CH═CH—C(O)—O— or *—N═C(CF₃)—NH—, wherein * indicates bonding to the position shown by R³, R⁷: —H, -lower alkyl or —CO-lower alkyl, B: aryl which may have a substituent(s) or heteroaryl which may have a substituent(s), and R¹ and R²: the same or different from each other, and each represents H, lower alkyl or O-lower alkyl which may have a substituent(s)).

4. A compound selected from the group consisting of 4-benzylamino-2-[(4-morpholin-4-ylphenyl)amino]pyrimidine-5 -carboxamide, 2-[(4-morpholin-4-ylphenyl )amino]-4-[(2,3 ,6-trifluorobenzyl)amino]pyrimidine-5 -carboxamide, 4-[(2,5 -difluorobenzyl) amino]-2-[(4-morpholin-4-ylphenyl)amino]pyrimidine-5 -carboxamide, 4-[(2,6-difluorobenzyl) amino]-2-[(4-morpholin-4-ylphenyl)amino] pyrimidine-5 -carboxamide, 4-[(2-methoxybenzyl) amino]-2-[(4-morpholin-4-ylphenyl)amino]pyrimidine-5 -carboxamide, 4-[(2-fluoro -6-methoxybenzyl)amino]-2-[(4-morpholin-4-ylphenyl)amino]pyrimidine-5 -carboxamide, 2-( {4-[(1 -methylpiperidin-3 -yl)oxy]phenyl}amino)-4-[(2,3 ,6-trifluorobenzyl)amino]pyrimidine-5-carboxamide, 2-{[4-( 1 -azabicyclo [2.2.2]oct-3-yloxy)phenyl]amino }-4-[(2,3 ,6-trifluorobenzyl) amino]pyrimidine-5 -carboxamide, 2- [(4-methyl-3 ,4-dihydro-2H- 1 ,4-benzoxazin-7-yl) amino]-4- [(2,3,6-trifluorobenzyl)amino]pyrimidine-5 -carboxamide, 2-( {4- [4-(2-amino-2-oxoethyl) piperazin- 1 -yl] phenyl}amino)-4- [(2,3 ,6-trifluorobenzyl)amino] pyrimidine-5 - carboxamide, 2- {[4-(2-morpholin-4-ylethoxy)phenyl]amino }-4- [(2,3,6-trifluorobenzyl) amino] pyrimidine-5 -carboxamide, 2- {[4-(β-D-glucopyranosyloxy) phenyl]amino }-4-[(2,3 ,6-trifluorobenzyl)amino]pyrimidine-5 -carboxamide, 4-benzylamino-2- {[2-(3 -chloro-4-hydroxyphenyl)ethyl]

amino}pyrimidine-5-carboxamide, 4-benzylamino-2-{[2-(3,5-dichioro-4-hydroxyphenyl)ethyl]amino}pyrimidine-5-carboxamide, 2-[(4-morpholin-4-ylphenyl)amino]-4-[(2-thienylmethyl)amino]pyrimidine-5-carboxamide, 4-{[(3-chloro-2-thienyl)methyl]amino}-2-[(4-morpholin-4-ylphenyl)amino]pyrimidine-5-carboxamide and 2-{[3-(2-morpholin-4-ylethyl)phenyl]amino}-4-[(2,3,6-trifluorobenzyl)amino]pyrimidine-5-carboxamide or salts thereof.

5. The compound of claim 1 wherein B is a cycloalkyl.

6. The compound of claim 5 wherein B is cyclopropyl or cyclobutyl which may have substituent(s).

7. The compound of claim 6 wherein B is cyclopropyl or cyclobutyl.

8. The compound of claim 5 wherein $R^1$ and $R^2$ are both H.

9. The compound of claim 5 wherein $A^1$ is $CR^5$ and $A^2$ is $CR^6$, and wherein $R^5$ and $R^6$ are both H.

10. The compound of claim 5 wherein $R^3$ is —$R^0$,-halogen or -hetero ring, and wherein $R^0$ is H or lower alkyl.

11. The compound of claim 10 wherein $R^3$ is -hetero ring substituted with 1 to 5 of lower alkyl, —OH, —$SO_2$-lower alkyl, lower alkylene-$OR^0$, —$CO_2R^0$, —$CON(R^0)_2$ or —$N(R^0)$—CO-lower alkyl.

12. The compound of claim 5 wherein n is 0.

13. The compound of claim 12 wherein $R^4$ is —$X^a$—$R^{4a}$, and wherein $X^a$ is a single bond, —CO—, —$SO_2$—, —$N(R^0)$CO— or —$N(R^0)SO_2$—, and $R^{4a}$ is lower alkyl, phenyl, hetero ring, cycloalkyl or lower alkylene-OH.

14. The compound of claim 13 wherein $R^{4a}$ is hetero ring substituted with 1 to 5 of lower alkyl, —OH, —$SO_2$-lower alkyl, lower alkylene-$OR^0$, —$CO_2R^0$, —$CON(R^0)_2$ or —$N(R^0)$—CO-lower alkyl.

15. The compound of claim 5 wherein $R^3$ and $R^4$ taken together form *—$N(R^7)$—CH=CH—, *—$N(R^7)$—N=CH— or *—CH=N—$N(R^7)$—, wherein * indicates bonding to the position shown by $R^3$.

16. A composition comprises a compound of any one of claims 1, 2 or 3, or a salt thereof and pharmaceutically acceptable carrier.

17. A method for treating asthma comprising administering an effective amount of a compound or a salt thereof, according to any one of claims 1, 2 or 3, to the subject, wherein the subject is a mammal.

18. A method for treating a chronic obstructive pulmonary disease (COPD) comprising administering an effective amount of a compound or a salt thereof, according to any one of claim 1, 2 or 3, to the subject wherein the subject is a mammal.

* * * * *

SEQUENCE LISTING

<160> NUMBER OF SEQ ID NOS: 4

<210> SEQ ID NO 1
<211> LENGTH: 71
<212> TYPE: DNA
<213> ORGANISM: Artificial Sequence
<220> FEATURE:
<223> OTHER INFORMATION: enhancer

<400> SEQUENCE: 1
tcgagcgctg ttgctcaatc gacttcccaa gaacagagct gttgctcaat cgacttccca    60
agaacagaga a    71

<210> SEQ ID NO 2
<211> LENGTH: 71

```
<212> TYPE: DNA
<213> ORGANISM: Artificial Sequence
<220> FEATURE:
<223> OTHER INFORMATION: enhancer

<400> SEQUENCE: 2
gatcttctct gttcttggga agtcgattga gcaacagctc tgttcttggg aagtcgattg    60
agcaacagcg c                                                          71

<210> SEQ ID NO 3
<211> LENGTH: 26
<212> TYPE: DNA
<213> ORGANISM: Artificial Sequence
<220> FEATURE:
<223> OTHER INFORMATION: TATA box

<400> SEQUENCE: 3
gatctggggg gctataaaag ggggta                                          26

<210> SEQ ID NO 4
<211> LENGTH: 26
<212> TYPE: DNA
<213> ORGANISM: Artificial Sequence
<220> FEATURE:
<223> OTHER INFORMATION: TATA box

<400> SEQUENCE: 4
agcttacccc cttttatagc ccccca                                          26
```